(12) United States Patent
Evoy et al.

(10) Patent No.: US 9,885,713 B2
(45) Date of Patent: Feb. 6, 2018

(54) DIAGNOSIS AND TREATMENT OF MYCOBACTERIA INFECTIONS

(71) Applicant: The Governors of the University of Alberta, Edmonton (CA)

(72) Inventors: Stephane Evoy, St. Albert (CA); Denis Arutyunov, Edmonton (CA); Upasana Singh, Edmonton (CA); Christine Szymanski, Edmonton (CA)

(73) Assignee: The Governors of the University of Alberta, Alberta (CA)

( * ) Notice: Subject to any disclaimer, the term of this patent is extended or adjusted under 35 U.S.C. 154(b) by 0 days.

(21) Appl. No.: 14/909,430

(22) PCT Filed: Aug. 1, 2014

(86) PCT No.: PCT/IB2014/063636
§ 371 (c)(1),
(2) Date: Feb. 1, 2016

(87) PCT Pub. No.: WO2015/015472
PCT Pub. Date: Feb. 5, 2015

(65) Prior Publication Data
US 2016/0195525 A1    Jul. 7, 2016

Related U.S. Application Data

(60) Provisional application No. 61/861,866, filed on Aug. 2, 2013.

(51) Int. Cl.
| | |
|---|---|
| A61K 39/04 | (2006.01) |
| A61K 39/02 | (2006.01) |
| A61K 39/00 | (2006.01) |
| G01N 33/569 | (2006.01) |
| C07K 14/005 | (2006.01) |
| G01N 33/543 | (2006.01) |
| C12N 7/00 | (2006.01) |
| C12Q 1/68 | (2006.01) |

(52) U.S. Cl.
CPC ....... G01N 33/5695 (2013.01); C07K 14/005 (2013.01); C12N 7/00 (2013.01); C12Q 1/689 (2013.01); G01N 33/54393 (2013.01); *C12N 2795/10322* (2013.01)

(58) Field of Classification Search
CPC ................. A61K 39/00; A61K 39/04

USPC ...... 424/9.1, 9.2, 184.1, 185.1, 234.1, 248.1
See application file for complete search history.

(56) References Cited

FOREIGN PATENT DOCUMENTS

| | | | |
|---|---|---|---|
| WO | 2004008938 A2 | 1/2004 | |
| WO | WO2008/121830 | * 10/2008 | ............. A61K 38/16 |
| WO | 2008121830 | 7/2009 | |

OTHER PUBLICATIONS

Fan, Xiangyu et al., "Biology of a Novel Mycobacteriophage, SWU1, Isolated from Chinese Soil as Revealed by Genomic Characteristics," Journal of Virology, vol. 86, No. 18, Sep. 2012, p. 10230-10231.

Hatfull, Grahma F. et al., "DNA Sequence, Structure and Gene Expression of Mycobacteriophage L5: a Phage System for Micobacterial Genetics," Molecular Micorbiology, vol. 7, No. 3, 1993, p. 395-405.

International Search Report corresponding to related PCT Application No. PCT/IB2014/063636 published with PCT Publication No. WO2015/015472 dated Feb. 2, 2015.

* cited by examiner

*Primary Examiner* — Rodney P Swartz

(74) *Attorney, Agent, or Firm* — Mark F. Vickers; Borden Ladner Gervais LLP

(57) ABSTRACT

The invention provides isolated, purified, recombinant receptor binding proteins Gp-6, Gp-10 and Gp-31 from *mycobacterium* phage L5, and methods for producing these recombinant receptor binding proteins. The invention also provides the use of recombinant receptor binding proteins, including Gp-6, Gp-10 and Gp-31, as probes for the identification and diagnosis of *mycobacterium* infections and conditions caused by *mycobacterium*. Further provided by the invention are methods of targeting mycobacteria using recombinant receptor binding proteins, including Gp-6, Gp-10 and Gp-31. Other methods provided by the invention include the use of recombinant receptor binding proteins, such as Gp-10, in diagnostic assays for diseases, such as Johne's disease, in animals, including ruminants.

18 Claims, 29 Drawing Sheets

| Confidence | % i.d. | Template Information |
|---|---|---|
| 96.8 | 26 | Fold: Cysteine proteinases<br>Superfamily: Cysteine proteinases<br>Family: NlpC/P60 |
| 96.6 | 32 | PDB header: hydrolase<br>Chain: A: PDB Molecule: putative uncharacterized protein;<br>PDBTitle: crystal structure of the p60 domain from m. avium subspecies2 paratuberculosis antigen map1204 |
| 96.6 | 17 | PDB header: unknown function<br>Chain: A: PDB Molecule: putative uncharacterized protein;<br>PDBTitle: crystal structure of the p60 domain from m. avium2 paratuberculosis antigen map1272c |
| 96.4 | 24 | PDB header: structural protein<br>Chain: A: PDB Molecule: hypothetical invasion protein;<br>PDBTitle: structure of rv1477, hypothetical invasion protein of2 mycobacterium tuberculosis |
| 96.6 | 38 | PDB header: hydrolase<br>Chain: A: PDB Molecule: invasion protein;<br>PDBTitle: structure of the peptidoglycan hydrolase ripb (rv1478) from2 mycobacterium tuberculosis at 1.6 resolution |
| 96.4 | 23 | PDB header: hydrolase<br>Chain: B: PDB Molecule: cog0791: cell wall-associated hydrolases (invasion-<br>PDBTitle: crystal structure of a putative gamma-d-glutamyl-l-diamino acid2 endopeptidase (npun_r0659) from nostoc punctiforme pcc 73102 at 1.793 a resolution |
| 96.2 | 20 | PDB header: hydrolase<br>Chain: B: PDB Molecule: putative gamma-d-glutamyl-l-diamino acid endopeptidase;<br>PDBTitle: crystal structure of a putative gamma-d-glutamyl-l-diamino acid2 endopeptidase (dvu_0896) from desulfovibrio vulgaris hildenborough at3 1.75 a resolution |

*Figure 1B*

| | | PDB header: lipoprotein<br>Chain: A; PDB Molecule: lipoprotein spr;<br>PDBTitle: solution nmr structure of lipoprotein spr from escherichia coli k12.2 northeast structural genomics target er541-37-162 |
|---|---|---|
| 95.0 | 32 | |
| 95.0 | 20 | PDB header: hydrolase<br>Chain: B; PDB Molecule: putative dipeptidyl-peptidase vi;<br>PDBTitle: crystal structure of a putative dipeptidyl-peptidase vi (bacova_00612)2 from bacteroides ovatus at 1.72 a resolution |
| 91.0 | 19 | PDB header: hydrolase<br>Chain: A; PDB Molecule: nlp/p60 family protein;<br>PDBTitle: crystal structure of a nlpc/p60 family protein (bce_2878) from2 bacillus cereus atcc 10987 at 1.79 a resolution |

B) ii i ii iii iv v.

SEM

FM

*SEM*

*FM*

SEM

FM

SEM

FM

SEM

FM

*SEM*

*FM*

SEM

FM

SEM

FM

DIAGNOSIS AND TREATMENT OF MYCOBACTERIA INFECTIONS

CROSS-REFERENCE TO RELATED APPLICATIONS

This application is a National Stage filing under 35 U.S.C. § 371 of International Application No. PCT/IB2014/063636, filed 1 Aug. 2014, which claims the benefit of U.S. Provisional Patent Application No. 61/861,866 filed on 2 Aug. 2013, the contents of which are incorporated herein by reference. A claim of priority is made.

SEQUENCE LISTING

The instant application contains a Sequence Listing which has been submitted electronically in ASCII format and is hereby incorporated by reference in its entirety. Said ASCII copy, created on Jul. 31, 2014, is named 5015.004PCT1_SL.txt and is 20,474 bytes in size.

BACKGROUND OF THE INVENTION

Johne's disease is a potentially deadly condition in cattle usually caused by *Mycobacterium avium* subsp. *paratuberculosis*, which is abbreviated as MAP. Due to the deficiency of a practical diagnostic test for MAP, the estimation of actual prevalence and economic losses caused by Johne's remained in darkness, despite the significant impact of this disease in all domestic ruminant industries worldwide. The infection happens in the first few months of an animal's life but the symptoms usually develop after a couple of years.

Two major problems are associated with control of Johne's disease. First, for every clinically affected animal in a herd, there are usually dozens of animals which are infected but not showing any symptoms. Consequently, these subclinical carriers are the major source of further transmission of the disease. The second problem is that there is no rapid, reliable, inexpensive test for the identification of these carriers. Currently, the method of choice is the bacterial culture of feces on specialized media. Unfortunately, growing MAP on artificial media is difficult. Further reducing the ability to easily identify carriers of the disease is that the fecal microbial population in an animal varies with time, and thus, repeated culturing attempts are necessary before an infected individual can be identified. Techniques such as Enzyme-Linked Immunosorbent Assay (ELISA), biochemical tests and/or polymerase chain reaction (PCR) have been considered but there are limitations with each technique. ELISA is impeded by antibody degradation. PCR-based strategies are more reliable, but their reliability is still greatly limited by inhibition issues caused by interfering agents, such as fatty acids and calcium ions. Therefore, a need exists for improved techniques and methods for the diagnosis of Johne's disease.

SUMMARY OF THE INVENTION

The present invention relates to the invention of a novel recombinant receptor binding protein and its use as a probe or detection tool for Mycobacteria. The present invention further relates to the use of a novel recombinant receptor binding protein to capture of *Mycobacterium* species, including but not limited to *M. avium* and *M. avium* subspecies *paratuberculosis*. More particularly, the present invention relates to the novel recombinant receptor binding protein Gp-10 and the use of Gp-10 with *Mycobacterium avium* subsp. *paratuberculosis* to develop mycobacteriophage-based technologies for the diagnosis of diseases in animals. Animals that may be in need of such treatment include mammals, such as ruminants Methods of diagnosing diseases are provided herein, where the diseases include, but are not limited to Johne's disease.

One embodiment of the invention is an isolated, purified recombinant polypeptide, comprising an amino acid sequence defined by SEQ ID NO:3 or which is at least 95%, 90%, 85%, 80%, 75%, 70%, 65%, 60%, 55%, or 50% identical thereto. In some embodiments of the invention, the polypeptide is a receptor binding protein. In other embodiments of the invention, the receptor binding protein is from a *mycobacterium* phage. In certain other embodiments of the invention, the receptor binding protein is from the tail region of a *mycobacterium* phage, including but not limited to phage L5.

The invention also provides methods for producing a recombinant receptor binding protein, comprising identifying a gene encoding a receptor binding protein from a *mycobacterium* phage, amplifying said gene, cloning the amplified gene into an expression vector, inserting the vector into a bacterium, where the bacterium expresses the recombinant receptor binding protein. The invention further provides methods for producing a recombinant receptor binding protein, comprising identifying a gene encoding a receptor binding protein from among the putative carbohydrate binding proteins of a phage, amplifying said gene, cloning the amplified gene into an expression vector, inserting the vector into a bacterium, where the bacterium expresses the recombinant receptor binding protein. In some embodiments of the methods of the invention, the recombinant receptor binding protein is Gp-6, Gp-10 or Gp-31. In other embodiments of the methods of the invention, the recombinant receptor binding protein is purified.

Further provided by the invention are methods for the capture of mycobacteria cells in a sample, comprising immobilizing a recombinant receptor binding protein from a *mycobacterium* phage to the surface of a solid support, and contacting the solid support with an amount of a sample containing mycobacteria cells and other components, wherein the recombinant receptor binding protein binds mycobacteria cells in the sample and does not bind the other components of the sample. In certain embodiments of the methods of the invention, the recombinant receptor binding protein is Gp-6, Gp-10 or Gp-31. In other embodiments of the methods of the invention, the mycobacteria in the sample are *M. avium, M. avium* subspecies *paratuberculosis*, or *M. smegmatis*, or a mixture thereof.

Also provided by the invention are methods of diagnosing a condition caused by mycobacteria, comprising obtaining a biological sample from an animal suspected of having a condition caused by mycobacteria, contacting the sample with a recombinant receptor binding protein from a *mycobacterium* phage, detecting the formation of a complex between the mycobacteria cell surface from the mycobacteria in the sample and the receptor binding protein, and comparing said formation of a complex in the sample relative to a control sample, wherein the formation of a complex in the sample relative to the control sample is indicative of the animal having a condition caused by *mycobacterium*. In other embodiments of the methods of the invention, the recombinant receptor binding protein is Gp-6, Gp-10 or Gp-31. Also, in an embodiment of the invention, the mycobacteria in the sample are *M. avium* or *M. avium* subspecies *paratuberculosis*. In still other embodiments of the methods of the invention, the mycobacteria have cell surfaces, and cell walls. In some embodiments of the methods of the invention, the animal is a mammal, including humans, ruminants, or other animals. In certain other embodiments of the methods of the invention, the condition is Johne's disease.

The invention further provides methods of enhancing the sensitivity of a diagnostic assay for mycobacteria, comprising obtaining a sample containing mycobacteria from a subject, performing the method for the capture of mycobacteria cells as provided herein, where the capture method provided herein concentrates the mycobacteria in the sample; and then performing a diagnostic assay on the concentrated sample, wherein the sensitivity of the diagnostic assay is increased using the concentrated sample, as compared to the sensitivity of the diagnostic assay when using a corresponding unconcentrated sample.

In some embodiments of the methods of the invention, the subject is an animal, including a human. In some embodiments of the methods of the invention provided herein above, the sample is milk from an animal or other dairy product. In some embodiments of any of the methods of the invention, the receptor binding protein is from the tail region of a *mycobacterium* phage, including but not limited to phage L5.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION OF THE INVENTION

Definitions

Figure 1A:
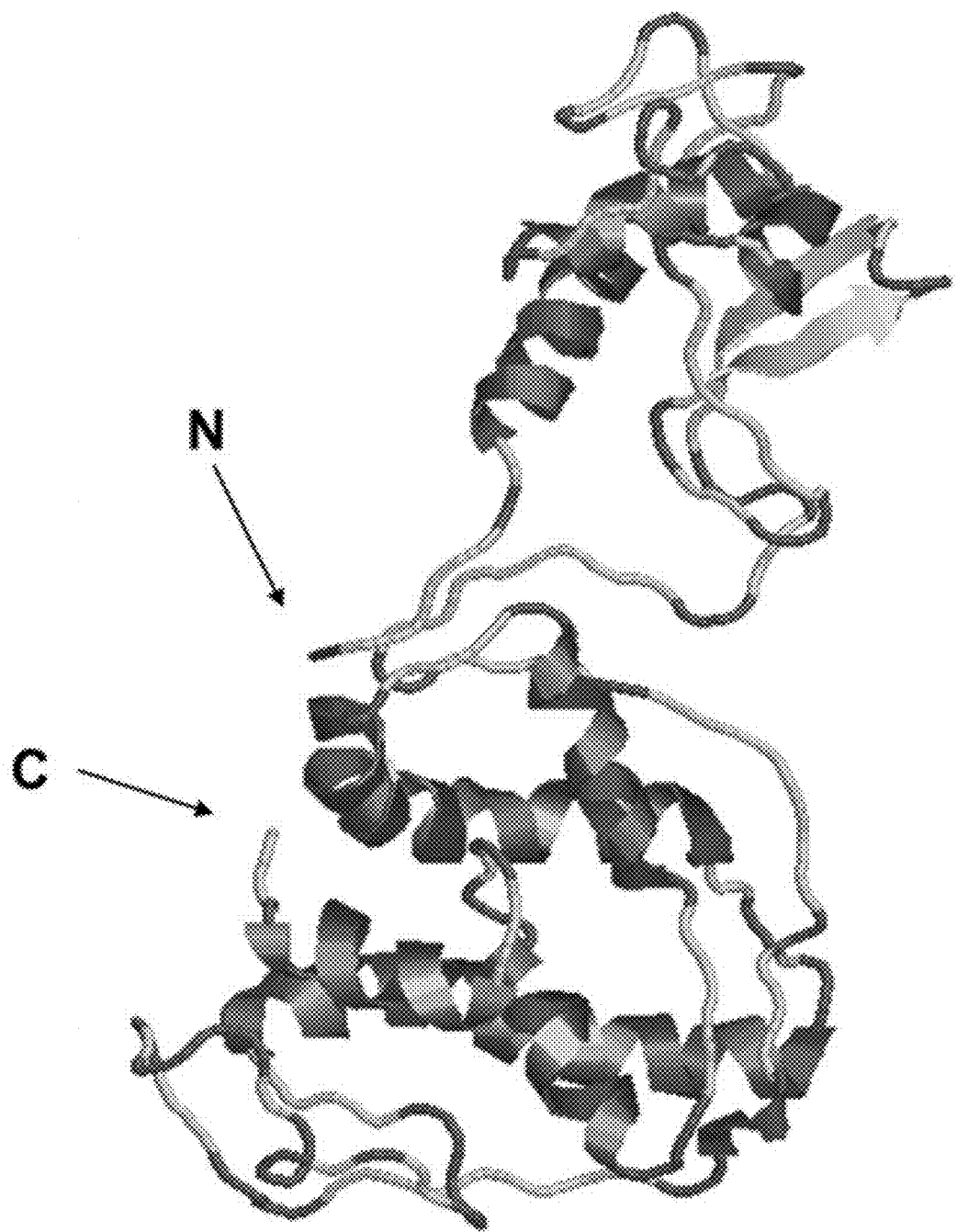
FIG. 1: Results of amino acid sequence analysis of L5 phage protein Gp-10 using Protein Homology/analogY Recognition Engine v. 2.0 (Phyre2) software (Structural Bioinformatics Group, Imperial College, UK). A) Phyre 2-generated model of Gp-10; B) Gp-10 under Phyre 2 analysis (blue frame indicates high scoring templates with the cell wall binding properties).

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described.

The singular forms "a," "an," and "the" include plural reference unless the context clearly dictates otherwise. Thus, for example, a reference to "a plant" includes a plurality of such plants. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by the skilled artisan, all numbers, including those expressing quantities of reagents or ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The phrases "genetic information" and "genetic material", as used herein, refer to materials found in the nucleus and/or cytoplasm of a cell, which play a fundamental role in determining the structure and nature of cell substances, and capable of self-propagating and variation. The phrase "genetic material" as used herein may be a gene, a part of a gene, a group of genes, DNA, RNA, nucleic acid, a nucleic acid fragment, a nucleotide sequence, a polynucleotide, a DNA sequence, a group of DNA molecules, double-stranded RNA (dsRNA), small interfering RNA or small inhibitory RNA (siRNA), or microRNA (miRNA) or the entire genome of an organism.

As used herein, the term "nucleic acid" and "polynucleotide" refers deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucl. Acids Res., 19:508 (1991); Ohtsuka et al., J. Biol. Chem., 260: 2605 (1985); Rossolini et al., Mol. Cell. Probes, 8:91 (1994).

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

"Polypeptide" as used herein refers to a polymer of amino acids and does not refer to a specific length of a polymer of amino acids. Thus, for example, the terms peptide, oligopeptide, protein, and enzyme are included within the definition of polypeptide, whether naturally occurring or synthetically derived, for instance, by recombinant techniques or chemically or enzymatically synthesized. This term also includes post-expression modifications of the polypeptide, for example, glycosylations, acetylations, phosphorylations, and the like.

Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. A "nucleic acid fragment" is a fraction of a given nucleic acid molecule. The terms "nucleic acid", "nucleic acid molecule", "nucleic acid fragment", "nucleic acid sequence or segment", or "polynucleotide" may also be used interchangeably with gene, cDNA, DNA and RNA encoded by a gene.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Naturally occurring" is used to describe an object that can be found in nature as distinct from being artificially produced. For example, nucleotide sequence present in an organism (including a virus), which can be isolated from a source in nature and which has not been intentionally modified by man in the laboratory, is naturally occurring.

In the context of the present invention, an "isolated" or "purified" DNA molecule or an "isolated" or "purified" polypeptide or protein is a DNA molecule, or a polypeptide, or a protein, that exists apart from its native environment and is therefore not a product of nature. An isolated DNA molecule, polypeptide or protein may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. Alternatively, an isolated" nucleic acid is free of sequences that naturally flank the nucleic acid (i.e., sequences located at the 5' and 3' ends of the nucleic acid) in the genomic DNA of the organism from which the nucleic acid is derived.

A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

"Recombinant polypeptide," as used herein, refers to a polymer of amino acids joined together by peptide bonds which have been joined together using recombinant techniques and procedures as described in, for example, Sambrook and Russell, Molecular Cloning: A Laboratory Manual, Cold Spring Harbor, N.Y.: Cold Spring Harbor Laboratory Press (3rd edition, 2001).

"Recombinant DNA molecule" is a combination of DNA sequences that are joined together using recombinant DNA technology and procedures used to join together DNA sequences as described, for example, in Sambrook and Russell, Molecular Cloning: A Laboratory Manual, Cold Spring Harbor, N.Y.: Cold Spring Harbor Laboratory Press (3.sup.rd edition, 2001). "Recombinant protein," as used herein, refers to a protein derived from recombinant DNA.

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced. "Wild-type" refers to the normal gene, or organism found in nature without any known mutation. "Genome" refers to the complete genetic material of an organism.

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. The term "suitable regulatory sequences" is not limited to promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., Mol. Biotech., 3:225 (1995). "3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

The terms "transfection" and "transformation", as used herein, refer to the introduction of foreign DNA into eukaryotic or prokaryotic cells, or the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art and are disclosed in Sambrook et al., Molecular Cloning: A Laboratory Manual (2d ed., Cold Spring Harbor Laboratory Press, Plainview, N.Y.) (1989). See also Innis et al., PCR Protocols, Academic Press (1995); and Gelfand, PCR Strategies, Academic Press (1995); and Innis and Gelfand, PCR Methods Manual, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome.

"Capture," as used herein, refers to a procedure in which the RBP is used as part of a surface moiety in order to allow said surface to specifically bind to the targeted cell. Such surfaces could consist, but are not limited to any flat surface, nanoparticles, microparticles, nanowires, or any other structure that would otherwise not feature such affinity to the cell wall. Capture refers to the binding of the bacteria to the particular surface which nature is described in this application.

The polymerase chain reaction, or PCR is biochemical technology in molecular biology to amplify a single or a few copies of a piece of DNA across several orders of magnitude, generating thousands to millions of copies of a particular DNA sequence.

Real time PCR (RT-PCR) quantitative real time polymerase chain reaction (qPCR) or kinetic polymerase chain reaction is a laboratory technique based on the polymerase chain reaction, which is used to amplify and simultaneously quantify a targeted DNA molecule. For one or more specific sequences in a DNA sample, real time-PCR provides the ability to detect and quantify. The quantity can be an absolute number of copies or a relative amount when normalized to DNA input or additional normalizing genes. RT-PCR is based on the principle of the polymerase chain reaction, however, its distinguishing feature is that the amplified DNA is detected as the reaction progresses in real time. In standard PCR, the product of the reaction is detected at the end of the reaction. Currently, two exemplary methods for the detection of products in real-time PCR are: (1) non-specific fluorescent dyes that intercalate with any double-stranded DNA, and (2) sequence-specific DNA probes consisting of oligonucleotides that are labelled with a fluorescent reporter which provides detection only after hybridization of the probe with its complementary sequence to quantify messenger RNA (mRNA) and non-coding RNA in cells or tissues.

The phrase "solid support," as used herein refers to any structure of any size and any shape made from a material in its solid state. These include, but are not limited to, beads, particles, fibers, tubes, wafers, chips, filters, and membranes, of any solid material including but not limited to metals, polymers, dielectrics semiconductors and cellulose. For examples of solid supports suitable for use in the methods, techniques, systems, and technologies of the invention, see U.S. Pat. No. 8,163,567, which is incorporated by reference in its entirety.

As used herein, the phrase "biological sample" refers to any sample derived from a human, animal, plant, bacteria, fungus, virus, or yeast cell, or from any living or dead carbon-based organism, including but not limited to tissue, blood, bodily fluids, serum, sputum, mucus, bone marrow, stem cells, lymph fluid, secretions, and the like.

As used herein, "biological material" refers to the object to be sensed or detected or diagnosed by the techniques, methods, systems, and technologies provided herein. Biological material, thus, can be proteins, DNA, RNA, any genetic material, small molecules, proteins, protein fragments, bacteria or fragments of bacteria, viruses or viral particles, or any moiety to be detected by the techniques, methods, systems, and technologies provided herein.

The term "environmental sample," as used herein, includes, but is not limited to water, ballast water, drinking water, tap water, water from aquifers, industrial water, industrial discharge, industrial runoff, agricultural runoff, recreational water, recreational aquatic samples, recreational environmental samples, swimming pool water, process water, water treatment containers or facilities, as well as water or liquids from holding tanks, septic tanks, wells, beaches, lakes, rivers, ponds, pools, inland bodies of water, basins, creeks, inland seas, lagoons, lakelets, lochs, millponds, mouth, reservoirs, sluices, springs, tarns, any sort of fluid discharge that can include microorganisms, and the like.

As used herein, "recombinant RBP" refers to the recombinant receptor binding protein. As used herein, "MAP" refers to *Mycobacterium avium* subspecies *paratuberculosis*.

Foodborne diseases continue to cause a high level of morbidity and mortality, specifically for infants, young children, elderly and the immunocompromised individuals. The magnitude of the problem remains underrated due to inaccurate reporting in many parts of the world. Contaminants can occur in food at any stage of processing. It may result from environmental contamination, pollution from water, soil or air and from production to consumption. Development of innovative strategies for food and livestock monitoring are thus necessary.

It is estimated that one out of 10 cattle sold in auction facilities is infected by Johne's disease. This gastrointestinal disease leads to the dramatic loss of the productivity and the eventual death of the animal resulting in the significant economic losses. Johne's disease causes a loss between $200 million to $250 million annually to the American dairy industry. In 2007, a National Animal Health Monitoring Systems (NAHMS) study showed that 68.1% of U.S. dairy cattle are infected with *Mycobacterium avium* subsp. *paratuberculosis* (MAP), the causative organism of Johne's disease. About one out of four U.S. cattle operations includes a relatively high percentage of MAP-infected cows in its herds. This pathogen possesses a unique persistence in the intestine and the infected animal may not display symptoms of the disease of years. One subject is thus sufficient to infect 50% of the herd before any symptom is observed. The infected animals shed MAP in their milk and feces contributing to the rapid dissemination of infection among the industrial herds and in the environment. Thus, human population may also be exposed to MAP through consumption of the contaminated retail milk and ground water. Apparent survivability of this pathogen in retail pasteurized milk remains a matter of particular concern taking into account that almost every patient diagnosed with Crohn's disease was infected with MAP. A relationship between a chronic inflammatory bowel disease in humans and MAP seems to exist. In 2002, it was estimated that between 400,000 to 600,000 patients in North America suffered from this disease and were intensively but not always successfully treated with corticosteroids, 5-aminosalicylate products and surgery.

The detection of MAP in human and animal tissues remains challenging. The pathogen has developed extraordinary resistance to the chemical and enzymatic lysis in the infected tissues. Lack of an optimized mechanical disruption step in sample processing hinders early diagnostics of MAP infections. *M. avium* subsp. *paratuberculosis* has primarily been detected through culturing of fecal samples. Culturing of MAP cells from fecal samples followed by the polymerase chain reaction based analysis (PCR) has recently emerged as the new golden standard for the diagnostics of this pathogen. It however takes 25 days to obtain a positive test result due to the extremely slow growth rate of this *mycobacterium*. Furthermore, a conclusively negative test result can require more than two months of incubation. PCR is also somewhat strenuous in complex samples such as fecal material and dairy food due to the presence of the natural inhibiting agents. Alternative immunological assays are impeded by the antibody degradation, cross reactivity and variability during different stages of infection and are often incapable of detecting subclinical MAP infection. FASTPlaque TB bacteriophage propagation based assay in combination with PCR was also suggested for the detection of MAP. Yet, this approach remains indirect and will inevitably be dependent on the quality of the live phage preparations used in the assay—a parameter which was always hard to standardize. Robotization of this assay may be problematic, too.

Bacteriophages are viruses that bind to receptors on the cell surface of their host bacteria, initiate infection. This results in amplification of phage DNA and, if the lytic pathway is initiated, kill the host cells and produce new phage particles. This recognition is highly specific and is useful for bacterial typing, i.e., the identification of bacterial cultures on the basis of their ability to be lysed by particular phage sets. This high specificity also makes immobilized bacteriophage particles potential platforms for culture-independent diagnosis of bacterial infections. This approach may be promising for the diagnosis of slow growing and/or fastidious bacteria.

In addition, bacteriophages are highly resilient to the agents responsible for antibody degradation, e.g., the presence of proteases in the natural samples. A recent review suggests that phage-based *mycobacterium* assays have high specificity, but the use of such assays is limited due to their modest sensitivity.

Phage-host specificity is mediated by the unique proteins located at their tails called receptor binding proteins (RBPs). The use of the actual RBPs responsible for phage specificity presents additional advantages over use of whole phage as probes of bacterial infections. More specifically, the substantially smaller size of RBPs insures a more uniform surface coverage of the biosensor elements used in different diagnostic platforms. RBPs can be engineered for increased affinity, specificity and binding properties, as compared to cumbersome phage genomic engineering. This provides for RBPs to have superior performance characteristics when used as probes. Moreover, RBPs recognize and bind to the host bacteria without inducing lytic cycle, which may preclude the effective detection of a pathogen because of the destruction of bacterial DNA and/or antigens.

As used herein, "mycobacteria" refers to a genus of gram-positive, rod shaped, acid-fast, aerobic, non-motile bacteria of the family Mycobacteriaceae. The genus includes both parasitic and saprophytic species, including *M. avium-intracellulare*, a complex that causes opportunistic infections in patients with HIV infection, *M. balnei* (*M. marinum*), the cause of swimming pool granuloma, *M. bovis*, the cause of cattle tuberculosis, transmitted to humans through milk, *M. kansasii*, the cause of a tuberculosis-like disease, *M. leprae*, the cause of leprosy, *M. tuberculosis* (the tubercle bacillus), the cause of tuberculosis, usually of the lungs, and *M. smegmatis*. While mycobacteria do not retain the crystal violet stain well, they are classified as acid-fast Gram-positive because they lack an outer cell membrane. *Mycobacterium* species members share a characteristic cell wall, which is thicker than in many other bacteria, and is hydrophobic, waxy, and rich in mycolic acids/mycolates. The cell wall consists of the outer surface, as well as a hydrophobic mycolate layer and a peptidoglycan layer held together by a polysaccharide, arabinogalactan. The cell wall makes a substantial contribution to the hardiness of this genus. In fact, the mycobacterial cell envelope or surface or wall surface contains a significant number of unique glycolypids that are essential for the growth and survival of these unusual bacteria and may also act as the phage receptors. *Mycobacterium* may be found in dairy products, including but not limited to milk, cheese, yogurt, and ice cream, as well as in other animal products, including but not limited to beef, and ground beef.

Applicants sought to provide efficient phage-based biomarkers for the use in diagnosing *Mycobacterium*-related diseases and conditions. The phage-based biomarkers of the invention retain their characteristic high specificity and resilience. Additionally, in certain embodiments, the invention leverages the high specificity of phage-host interactions as part of a pre-concentration strategy that significantly enhances the reliability of existing platforms, including but not limited to platforms such as real time PCR.

Bioinformatic analysis of the mycobacterial phage genomes was completed for the purpose of searching the genes encoding putative carbohydrate binding proteins. Genes encoding L5 phage tail proteins and genes adjacent to the genes of the tail proteins were chosen as the candidate RBP genes. RBP Gp-10 (herein referred to as "Gp-10") was selected as one of the best candidates with the highest model confidence score and is similar to the peptidoglican hydrolase (96% confidence).

Applicants have demonstrated the use of the immobilized bacteriophage particles for the detection of *Escherichia coli*. A recent review article has also indicated an enormous potential of bacteriophages for the rapid detection of the pathogenic bacteria. This being said, Applicants concluded that the use of the recombinant phage receptor binding proteins (RBPs) responsible for the phage-host specificity as biological probes presents numerous advantages over the use of the whole phage particles. Applicants have reported the use of RBPs as novel probes for the capture of several food borne pathogenic bacteria. Phage RBP immobilized onto magnetic particles was successfully used for the rapid isolation (in less than 3 hours) of the bacterial cells from the food samples spiked with *Campylobacter jejuni* cells.

Genetically engineered RBP Gp-10 was used for the sensitive and selective detection of MAP. Accordingly the present invention relates to the construction and production of recombinant receptor binding protein Gp-10 from bacteriophage L5. Further, the invention provides the use of Gp-10, having specific capturing activity for *Mycobacterium avium* subsp. *paratuberculosis*, for the development of highly specific platform for the diagnosis of *Mycobacterium avium* subsp. *paratuberculosis*, a slow growing bacterium, in minimal time. One embodiment of the invention provides for the use of mycobacteriophage-based technologies in the diagnosis of MAP.

The invention further provides for the use of the recognition bacteria by the protein Gp-10 as part of a pre-concentration step involving the highly specific capture and extraction of the mycobacteria from samples. This use relies on the inherent advantages of bacteriophage technologies—superior reliability and resilience to inhibiting agents—as compared to antibodies.

The present invention includes polypeptides having the amino acid sequence shown in SEQ ID NO 1, SEQ ID NO:3, or SEQ ID NO:5, and truncations and fragments thereof.

Truncations include, but are not limited to, amino acid sequences in which one, two, three, four, five, six, or more amino acids are removed from the amino terminus of the amino acid sequence and/or one, two, three, four, five, six, or more amino acids are removed from the carboxy terminus of the amino acid sequence.

The present invention includes polypeptides having an amino acid sequence with one, two, three, four, five, six, seven, eight, nine, ten, eleven, twelve, thirteen, fourteen, fifteen, sixteen, seventeen, eighteen, nineteen, twenty, or more amino acid changes from the amino acid sequence of SEQ ID NO:1, SEQ ID NO:3, or SEQ ID NO:5. Such amino acid changes include, but are not limited to, conservative amino acid changes. As used herein, the term "conservative substitution" refers to the replacement of an amino acid residue by a structurally similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

As used herein, "structural similarity" refers to the identity between two polypeptides. Structural similarity is generally determined by aligning the residues of the two polypeptides to optimize the number of identical amino acids along the lengths of their sequences; gaps in either or both sequences are permitted in making the alignment in order to optimize the number of identical amino acids, although the amino acids in each sequence must nonetheless remain in their proper order. For example, polypeptides may be compared using the Blastp program of the BLAST 2 search algorithm, as described by Tatusova et al. (FEMS Microbiol. Lett., 174; 247-250, 1999). In the comparison of two amino acid sequences using the BLAST search algorithm, structural similarity may be referred to by percent "identity" or may be referred to by percent "similarity." "Identity" refers to the presence of identical amino acids and "similarity" refers to the presence of not only identical amino acids but also the presence of conservative substitutions.

The present invention provides methods as described herein, including but not limited to methods for the detection of Mycobacteria species. In certain embodiments, the methods may employ determining that an antisera sample includes antibodies that specifically bind to a polypeptide of the present invention. In certain embodiments, the methods may employ detecting the hybridization of a polynucleotide of the present invention to a sample, preferably under high stringency conditions. In certain embodiments, the methods may employ producing a polymerase chain reaction (PCR) amplification, where the resultant amplicon demonstrates a sequence similar to a nucleotide sequence of the present invention. In certain embodiments, the methods may employ producing a polymerase chain reaction (PCR) amplification utilizing a primer pair described herein. The polypeptides, polynucleotides, and/or antibodies may be labeled with one or more of the detectable markers known to the skilled artisan. In some aspects, the polypeptides, polynucleotides, and/or antibodies may be bound to a solid substrate.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1: Identification and Production of Mycophage Receptor Binding Proteins

The search for the *mycobacterium* phage receptor binding protein (RBP) was performed on the basis of the known genome sequence of bacteriophage L5 that was the first genome sequence obtained for the temperate non *Escherichia coli* phage (Hatfull G F, Sarkis G J. *Mol. Microbiol.* (1993) 7(3):395-405). L5 phage has a broad host range and can infect not only benign *Mycobacterium smegmatis*, but also *M. tuberculosis* and *Mycobacterium avium* subsp. *paratuberculosis* cells. The nature of the L5 mycophage receptor(s) is still unknown.

Genes encoding L5 phage tail proteins and genes adjacent to the genes of the tail proteins were selected as candidate RBP genes. Recently released Protein Homology/analogY Recognition Engine v. 2.0 (Phyre2) software (Structural Bioinformatics Group, Imperial College, UK) was used to analyze the amino acid sequence of these proteins to choose the RBP candidates. Gp-6, Gp-10 and Gp-31 were chosen as the best candidates with the highest model confidence scores. Minor tail protein Gp-6 appeared to have similarity to the galactose binding domain (45% confidence), Gp-10 was similar to the peptidoglycan hydrolase (96% confidence) whereas Gp-31 resembled a concanavalin A lectin (77% confidence) (FIGS. 1A & B). The detection of the putative carbohydrate binding sites provided a good indication that Gp-6, Gp-10 and Gp-31 may be RBPs, taking into account that the mycobacterial cell envelope contains a number of complex polysaccharides that may serve as phage receptor(s).

All three corresponding genes were directly PCR amplified from the phage L5 suspension obtained from the Felix D'Herelle Phage Centre (Laval University) and cloned into pET-30a(+) vector (Novagen).

Gene 6 from mycobacterial phage L5 (phage genome was sequenced by Hatfull G F and Sarkis G J (1993) Mol. Microbiol. 7(3): 395-405). The gene was cloned in between EcoRI and HindIII sites into pET-30a(+) plasmid (Novagen). Therefore, the produced recombinant Gp-6 protein has additional N-terminal amino acid residues (see SEQ ID NO: 1).

Gene 10 from mycobacterial phage L5 (phage genome was sequenced by Hatfull G F and Sarkis G J (1993) Mol. Microbiol. 7(3): 395-405). The gene was cloned in between EcoRI and HindIII sites into pET-30a(+) plasmid (Novagen). The produced recombinant Gp-10 protein has additional N-terminal amino acid residues (SEQ ID NO: 3).

Gene 31 from mycobacterial phage L5 (phage genome was sequenced by Hatfull G F and Sarkis G J (1993) Mol. Microbiol. 7(3): 395-405). The gene was cloned in between EcoRI and HindIII sites into pET-30a(+) plasmid (Novagen). The produced recombinant Gp-31 protein has additional N-terminal amino acid residues (see SEQ ID NO: 5).

Recombinant proteins were produced in *E. coli* BL21 (DE3) cells as His-tagged polypeptides and purified using immobilized metal affinity chromatography. All three purified recombinant proteins (Gp-6, Gp-10 and Gp-31) were immobilized onto gold coated chips activated with cysteamine/gluteraldehyde.

Example 2: Assessment of Mycophage and Mycophage RBPs as Probes of MAP Infection In order to assess mycophage and mycophage RBPs for their use as probes of MAP infection, Gp-10 and Gp-6 were immobilized using an established protocol (Singh et. al. Biosens. Bioelect. 26 131 (2010) and used for the specific bacterial capture. Gold Surfaces were modified by cysteamine hydrochloride followed by activation using 2% gluteraldehyde. The recombinant proteins Gp-10, Gp-6 and Gp-31 were immobilized over the surfaces in order to capture the host bacteria *Mycobacterium avium* subsp. *paratuberculosis* ATCC 19851 and *Mycobacterium smegmatis* mc$^2$155. Bacterial capture was confirmed by fluorescence microscopy and Scanning Electron Microscopy (SEM). Nonspecific attachment was prevented by using bovine serum albumin (BSA) as the blocking layer. A negative control was run in parallel where a similar gold surface was treated with all reagents, but they were not exposed to the recombinant phage proteins. No significant bacterial capture was observed in the absence of phage proteins.

Figure 2:
FIG. 2: SEM images of *M. smegmatis* capture by Gp-6 on the gold surface and the corresponding fluorescence microscopy images (labeled i and ii, respectively). A) i,ii—Gold Surface was modified with cysteamine hydrochloride, activated with 2% gluteraldehyde and incubated with 20 µg/ml of recombinant protein Gp-6 followed by wash with buffer B) i,ii—The surface was treated in a same way as indicated above except that it was not exposed to the recombinant protein.
Figure 2:
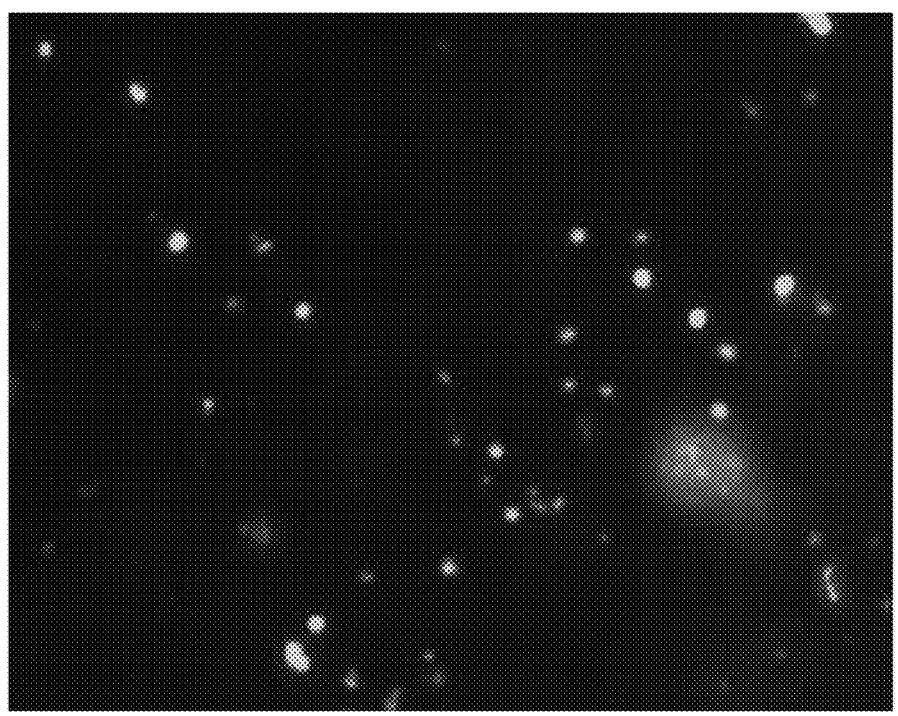
Figure 2:
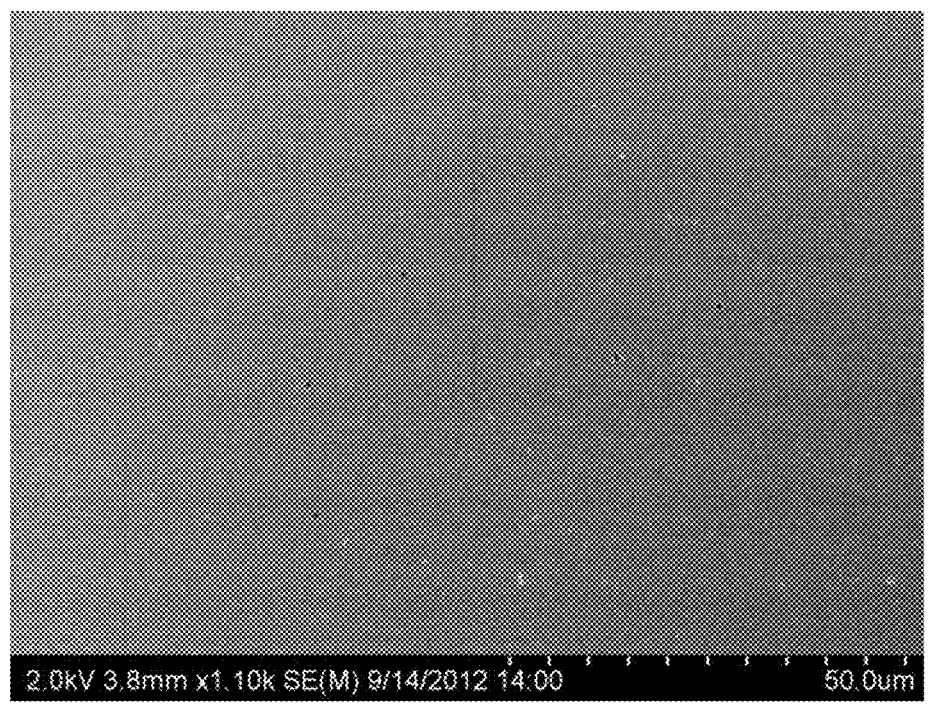
Figure 2:
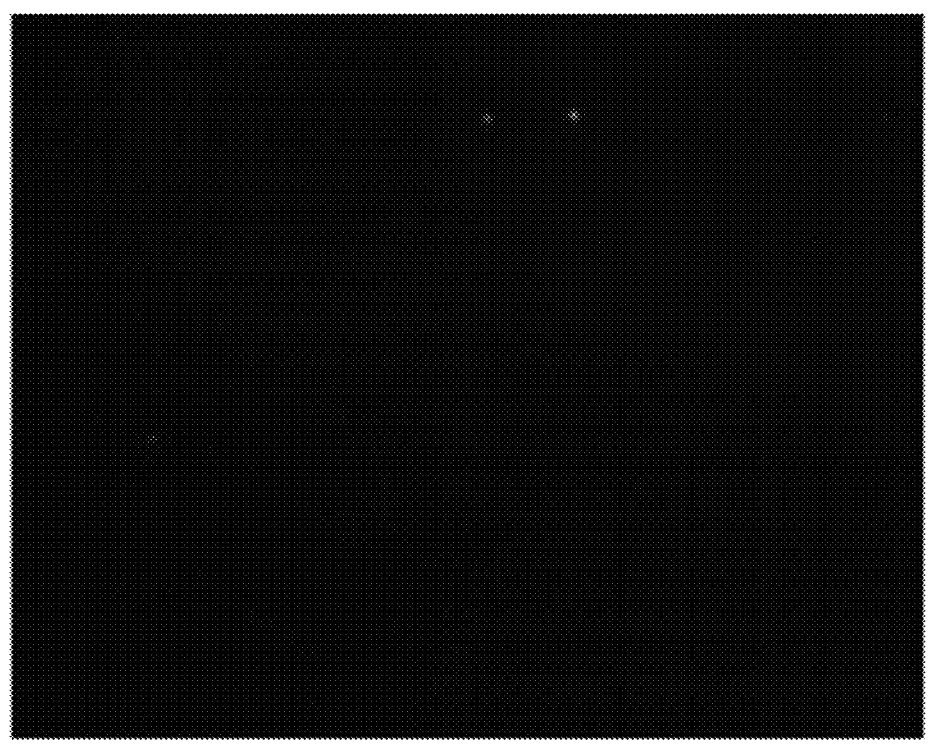
Figure 4:
FIG. 4: SEM images of *Mycobacterium avium* subsp. *paratuberculosis* ATCC 19851capture by Gp-6 on the gold surface and the corresponding fluorescence microscopy images (labeled i and ii, respectively). A) i,ii—Gold Surface was modified with cysteamine hydrochloride, activated with 2% gluteraldehyde and incubated with 20 g/ml of recombinant protein Gp-6 followed by wash with buffer B) i,ii—The surface was treated in a same way as indicated above except that it was not exposed to the recombinant protein.
Figure 4:
Figure 4:
Figure 4:
Figure 5:
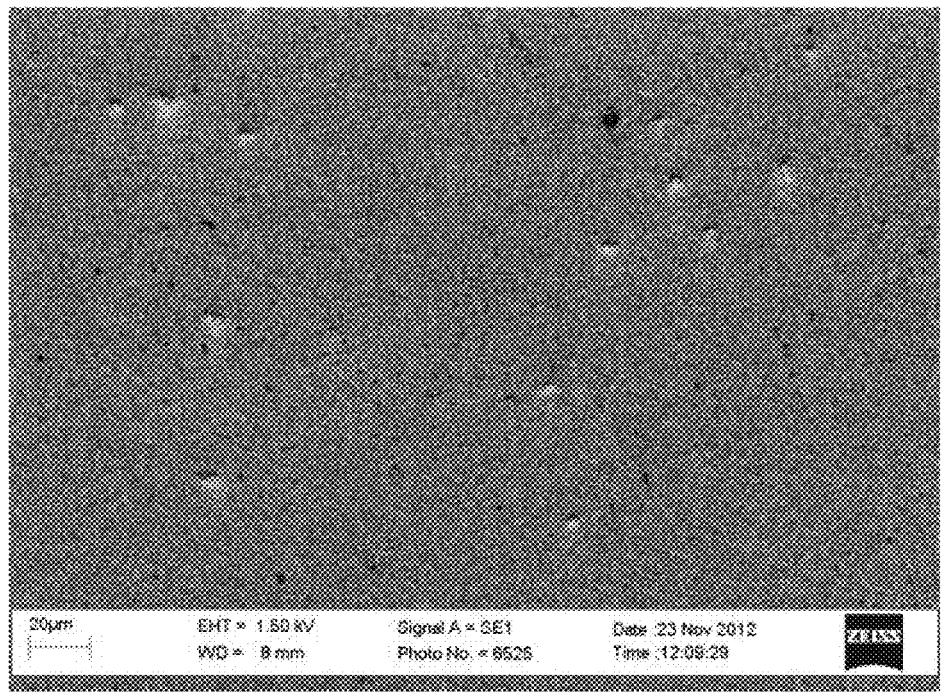
FIG. 5: SEM images of *Mycobacterium avium* subsp. *paratuberculosis* ATCC 19851capture Gp-10 on the gold surface and the corresponding fluorescence microscopy images (labeled i and ii, respectively). A) i,ii—Gold Surface was modified with cysteamine hydrochloride, activated with 2% gluteraldehyde and incubated with 20 g/ml of recombinant protein Gp-10 followed by wash with buffer B) i,ii—The surface was treated in a same way as indicated above except that it was not exposed to the recombinant protein.
Figure 5:
Figure 5:
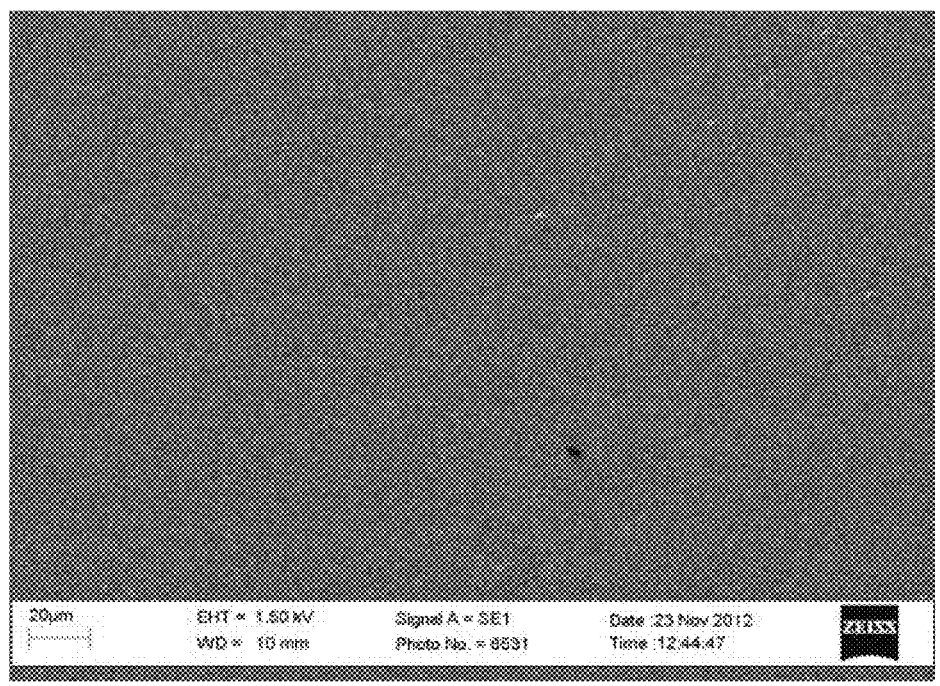
Figure 5:
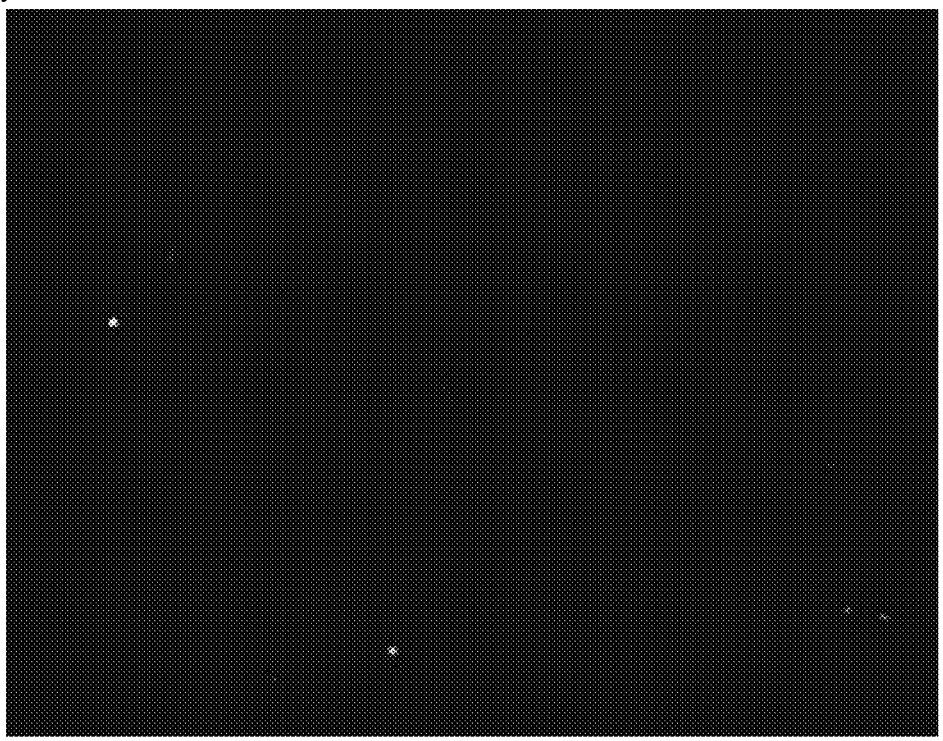

The concentrations of the two RBPs of Gp6, Gp-10 and Gp31 were optimized for immobilization. Twenty µg/ml of RBPs Gp-6 and Gp-10 showed bacterial capture of $31.3 \times 10^{-3}/\mu m^2$ (FIG. 2) and $28.7 \times 10^{-3}/\mu m^2$ (FIG. 3) for *Mycobacterium smegmatis* mc$^2$155. Whereas 20 and 40 µg/ml of RBP Gp-6 was not showing any bacterial capture for *Mycobacterium avium* subsp. *paratuberculosis* ATCC 19851 (FIG. 4) but 20 µg/ml concentration of Gp-10 was showing $12.3 \times 10^{-3}/\mu m^2$ capture of bacteria (FIG. 5). However, 20 µg/ml of immobilized Gp-31 has no significant bacterial capture for any of the mycobacterial species. The specificity of recognition by the RBPs was confirmed by exposing similar surfaces to *E. coli* EC12 and *Campylobacter jejuni* 11168H strains of non-host bacteria. These negative control experiments showed no bacterial capture.

Example 3: Assessment of Mycophage RBPs as Probes for Detection and Isolation MAP Contamination in Milk In another embodiment of the invention, immobilization of GP-10 was achieved by commercially available magnetic beads Dynabeads® M-280 Tosylactivated (AsSE Invirtogen, USA) and those functionalized beads were applied for specific bacterial capture. 20 µl of 100 mg/ml Tosylactivated beads were suspended in 1 ml of 0.1 M Na-phosphate buffer (pH 7.4) (PBS) and washed twice in sterile PBS. The beads were separated from any liquid suspension by using magnet. The cleaned beads were incubated with 100 µg/ml Gp-10 and GP-6 for 1 hour at 37° C. followed by overnight incubation at room temperature. The functionalized beads were further incubated in 1 mg/ml BSA for 30 min to block the free surface and prevent nonspecific binding. The beads are washed twice in PBS to remove the unbounded BSA.

1, 2 and 3% of Difco skimmed milk (BD Company MD, USA) in 0.1 M Na-phosphate buffer (pH 7.4) (PBS) was artificially spiked by using $10^7$ cfu/ml *Mycobacterium avium* subsp. *paratuberculosis* ATCC 19851, respectively. 3% of skimmed milk in PBS was artificially spiked with a mixture of $10^7$ cfu/ml *Mycobacterium avium* subsp. *paratuberculosis* ATCC 19851 and $10^7$ cfu/ml *E. coli*. The *Mycobacterium avium* subsp. *paratuberculosis* ATCC 19851 used in these experiments were prestained with fluorescent dye prior to their addition to the milk. The Gp-10 functionalized beads were suspended in the artificially spiked milk (described in preceding sentences), as well as in clean PBS buffer, and were incubated for 1 hour at room temperature. The beads were separated by using a magnet and washed twice in sterile PBS. The beads were washed for a final time, in 0.5 ml of sterile water, and then re-suspended in 50 µl Quick-Extract Bacterial DNA solution (Epicenter Biotechnologies, USA). 2 µl of Ready Lyse Lysozyme solution (Epicenter Biotechnologies, USA) was added in each sample. The solutions were mixed gently with the beads and incubated overnight at room temperature. The samples were then heated at 80° C. for 5 minutes to kill any viable bacteria. The bacterial capture was confirmed by fluorescence microscopy (see FIG. 6).

Example 4: Increasing the Sensitivity of Real Time PCR Analysis

Primers and TaqMan probe (Applied Biosystems, USA) were designed using Primer Express 3.0 software (Applied Biosystems, USA) to amplify a fragment of gene IS900 found in all *M. avium* subspecies *paratuberculosis* cells. From such area, forward primer 5'-TGACGGTTACGGAG-GTGGTT-3' (SEQ ID NO: 7), and reverse primer 5'-AT-GCAGTAATGGTCGGCCTTA-'3 (SEQ ID NO: 9) containing the Taqman probe 5'-TGGCACAACCTGTCTG-3' (SEQ ID NO: 11), were selected.

The probe was labeled with reporter dye 6-carboxylflurescein (FAM) at 5'end and with non fluorescent Black hole Quencher Dye (BHQ) at the 3' end. The primers and probes were procured from Integrated DNA Technologies, Canada). The Real time PCR amplification was performed using StepOnePlus Real Time PCR System (Applied Biosystems, USA) in 10 µl volume. Each reaction mixture comprised of 5 µl of TaqMan® Universal Master Mix II with UNG(Life Technologies, Canada), 200 nM of each primers and 250 nM of Fluorogenic probe. 4 ml of each unknown sample was added in the reaction mixture. The real time PCR cycling conditions were: 50° C. for two min for UNG enzyme activity, 95° C. for 10 min to denature the UNG enzymeand activate DNA polymerase, 40 cycles of 15 seconds at 95° C. and 1 min at 60° C. Each data point was run in triplicates and with negative and positive controls. Data obtained was analyzed in the form of threshold cycle (Ct) values (see Table 1).

TABLE 1

| Serial number | Sample type | Real time PCR (Ct) |
|---|---|---|
| 1. | *Mycobacterium avium* subsp. *paratuberculosis* ATCC 19851 Preconcentrated from PBS | 15.5 ± 0.18 |
| 2. | *Mycobacterium avium* subsp. *paratuberculosis* ATCC 19851 Preconcentrated from 1% milk | 15.9 ± 0.012 |
| 3. | *Mycobacterium avium* subsp. *paratuberculosis* ATCC 19851 Preconcentrated from 2% milk | 16.7 ± 0.14 |
| 4. | *Mycobacterium avium* subsp. *paratuberculosis* ATCC 19851 Preconcentrated from 3% milk | 16.5 ± 0.083 |
| 5. | Mixture of *E.coli* and *Mycobacterium avium* subsp. *paratuberculosis* ATCC 19851 Preconcentrated from 3% milk | 17.3 ± 0.049 |
| 6. | *Mycobacterium avium* subsp. *paratuberculosis* ATCC 19851 in 3% milk (not concentrated) | 23.5 ± 0.29 |
| 7. | *Mycobacterium smegmatis* mc$^2$155 Preconcentrated from 3% milk | 23.3 ± 0.059 |

Real time PCR amplification was conducted for all preconcentrated *Mycobacterium avium* subsp. *paratuberculosis* ATCC 19851 samples isolated from 1, 2 and 3 percent of milk using Gp-10 functionalized Tosylactivated beads (FIG.

7). A certain volume of extracted DNA of unknown sample was added in the reaction mixture.

The beads were washed for a final time, in 0.5 ml of sterile water, and then re-suspended in 50 µl QuickExtract Bacterial DNA solution (Epicenter Biotechnologies, USA). 2 µl of Ready Lyse Lysozyme solution (Epicenter Biotechnologies, USA) was added in each sample. The solutions were mixed gently with the beads and incubated overnight at room temperature. The samples were then heated at 80° C. for 5 minutes to kill any viable bacteria.

The Ct values demonstrated by all pre-concentrated and isolated *Mycobacterium avium* subsp. *paratuberculosis* ATCC 19851 cells range between 15.5 and 17.3. The Ct values are very close to each other between the cells isolated from clean buffer as well as the highest percentage of milk. The Ct value for the non pre-concentrated cells is 23.5, which is very close to the Ct value (23.3) of concentrated *Mycobacterium smegmatis* mc2155 cells. This data shows that pre-concentration of the cells from a milk sample increases the sensitivity of the real time PCR analysis. A difference between the Ct values of *Mycobacterium avium* subsp. *paratuberculosis cells* and *Mycobacterium smegmatis* cells demonstrates the specificity of the technique towards the particular species.

Example 5: Mycobacteriophage Lysin-Mediated Capture of Cells for PCR Detection of *Mycobacterium avium* Subspecies *Paratuberculosis*

Lysins represent another class of the cell envelope binding phage proteins. Lysins are peptidoglycan hydrolases that degrade the host bacterial cell wall, facilitating the release of the newly formed phage particles or virions. Lysins have been proposed to act as a new class of antimicrobials capable of targeting antibiotic resistant pathogens. Engineered lysins, such as catalytically inactive recombinant lysins, have been suggested as reagents for the rapid detection of *listeria* and staphylococci.

We demonstrated that the immobilized recombinant lysin Gp10 from the mycobacteriophage L5 was able to capture MAP cells from the buffered saline (manuscript in the preparation). We are currently reporting the use of recombinant Gp10 for the capture of MAPs from the complex natural matrices. The recognition of cells by the Gp10 was leveraged as a pre-concentration step for the rapid and specific extraction of the mycobacteria followed by a validated real time PCR technique. In contrast to prior reports involving other pathogens, a comparative assessment of capture involving different subspecies has been performed. The present study is also innovative in its use of two target sequences (IS900 and F57) for the PCR analysis. Indeed, a number of PCR based assays have been reported for the detection of MAP in milk and the IS900 insertion element is an established standard marker for the detection of MAP. Specificity of the PCR assays based on this target sequence is however impeded by the presence of the highly homologous sequences in other mycobacteria. A few alternative target elements such as F57, IS Mav2 and HspX have been evaluated. While the F57 element is more specific for MAP, it is also known to show lower levels of amplification than IS900. For that reason, two target sequences were used in Applicants' study and the effectiveness of the Gp10 mediated capture of MAP cells was conclusively established.

Materials and Methods

Bovine serum albumin (BSA), dimethyl sulfoxide (DMSO), monosodium phosphate, sodium phosphate dibasic, and ammonium sulfate were purchased from Sigma-Aldrich. Phosphate buffered saline (PBS) solution was prepared by mixing one BupH phosphate buffered saline pack (Pierce) with 500 ml of MilliQ-grade water (Millipore) yielding a solution of 0.1 M sodium phosphate and 0.15 M NaCl (pH 7.2).

The procedure for Gp10 production was as follows. Briefly, gene 10 was amplified using the suspension of mycobacteriophage L5 (HER-386) obtained from Felix D'Herelle Reference Centre for Bacterial Viruses (Laval University, Quebec, Canada) and cloned into pET30a vector (Novagen). His-tagged recombinant protein (about 40 kDa polypeptide) was produced in *E. coli* BL21(DE3) cells and purified using immobilized metal affinity chromatography. The obtained Gp10 solution was dialyzed against PBS and used in the experiments. The protein concentration was determined by measuring the absorbance at 280 nm and assuming A0.1% of 1.402 for the His-tagged Gp10. ProtParam Tool was used to calculate the extinction coefficient ($53400$ $M^{-1}$ $cm^{-1}$). A280/A260 ratio was about 1.8 for the preparation of Gp10.

Bacterial Strains and Culture Media

The bacterial cultures used are *Mycobacterium avium* subsp. *paratuberculosis* ATCC 19851, *Mycobacterium avium* subsp. *paratuberculosis* ATCC 19698, *Mycobacterium marinum* ATCC 927, *Mycobacterium smegmatis* mc$^2$155 and *Escherichia coli* BL21(DE3). The mycobacteria strains used in this study were cultured in Middlebrook 7H9 broth (BD Biosciences) supplemented with the oleic acid-albumin-dextrose-catalase mixture (BD Biosciences) and mycobactin J (Allied Monitor, USA). All these cultures were incubated at 37° C. and with constant shaking at 200 rpm for 10 days. *M. smegmatis* cells were grown at the same conditions but without mycobactin and were incubated for only 48 hours. The *Mycobacterium marinum* ATCC 927 was also grown without mycobactin but incubated for 12 days in the same growth conditions as described above. All mycobacterial cells were sonicated for 5 min using sonicator (Branson Ultrasonics 1510, 40 kHz frequency) to make a homogeneous cell suspension prior to any subsequent manipulations. *E. coli* BL21(DE3) was cultured in Luria-Bertani broth for overnight at 37° C. with the shaking.

Immobilization of Gp10 onto Tosylactivated Dynabeads® M-280

M-280 Tosyl-activated Dynabeads were purchased from Life Technologies Inc. These beads are uniform magnetic round particles having a diameter of 2.8 µm, coated with a polyurethane layer and activated by p-toluensulfonyl chloride. The primary amino groups of the proteins react covalently with the sulfonyl ester group present on the beads. 20 µL of 100 mg/ml Dynabeads® M-280 were washed twice with sterile PBS for 10 min. The tubes containing washed beads were placed on a magnet for 1 min, and the supernatant was removed. The beads were resuspended in 1 ml of sterile PBS. The cleaned beads were incubated with 100 µg/ml Gp10 for 1 hour at 37° C. followed by overnight incubation at room temperature. The functionalized beads were further incubated with 1 mg/ml BSA for 30 min to block the free surface and prevent the nonspecific binding. Finally, the beads were washed twice with the sterile PBS to remove the unbound BSA.

Capture of Bacterial Cells from Milk and Other Media

Skim milk powder (BD Biosciences) was suspended in PBS to 1-3% (w/v) concentration and artificially spiked with $2.4 \times 10^7$ cfu/ml (0.25 $OD_{600}$) *M. avium* subsp. *paratuberculosis paratuberculosis* ATCC 19851 or *M. avium* subsp. *paratuberculosis* ATCC 19698. In another experiment, suspension of skimmed milk in PBS was artificially spiked with 2.4×10⁷ cfu/ml of MAP cells and 2.4×10⁷ cfu/ml of *E. coli* BL21(DE3) cells. *M. marinum* ATCC 927 and *M. smegmatis* mc²155 were also used to spike the milk in a same way. The Gp10 functionalized beads were suspended in the spiked milk), or in of sterile PBS buffer spiked with the MAP cells and were incubated for 1 hour at room. The beads were separated by incubating the samples on a magnetic separator for 5 min and washed twice with the sterile PBS. The Gp10 functionalized beads were also used to capture bacteria directly from Middlebrook 7H9 broth supplemented with the oleic acid-albumin-dextrose-catalase and mycobactin J. Fully grown cultures of *M. avium* subsp. *paratuberculosis* ATCC 19851 and *M. avium* subsp. *paratuberculosis* ATCC 19698 were diluted to 0.25 $OD_{600}$ (2.4×10⁷ cfu/ml) and exposed to Gp10 functionalized beads for 1 hour at room temperature in the same way as described above. The beads were then separated from the medium, washed and analyzed.

Fluorescence Microscopy

Once exposed to bacteria, the beads were washed with PBS and exposed to 50 μM resazurin (Sigma) in DMSO for 20 min. The stained beads were then washed twice in PBS to remove the excess of dye. An Olympus IX81 microscope equipped with a FITC filter and a Roper Scientific Cool-Snaps HQ CCD camera was used to record the fluorescence images.

Extraction of Genomic DNA

Genomic DNA was extracted from mycobacteria using the QuickExtract DNA extraction kit (Epicenter Biotechnologies) according to the manufacturer's instructions with some modifications. The samples were incubated for 1 hour with 50 μl of QuickExtract DNA extraction solution and 2 μl of Ready—Lyse lysozyme solution. This process was followed by incubation at 80° C. for 1 hour in a water bath for complete lysis of the cells. The concentration of the isolated DNA was determined by measuring sample absorbance at 260 nm using a NanoDrop ND-1000 spectrophotometer (NanoDrop Technologies Inc.).

Primers and Probes for the Target Sequences IS900 and F57

The primers and probes were purchased from Integrated DNA Technologies. Primers and TaqMan probe (Applied Biosystems) were designed using Primer Express 3.0 software to amplify the fragments of the sequences IS900 and F57 found in all *M. avium* subsp. *paratuberculosis* cells (Table 2). Forward primer and reverse primers containing the TaqMan probe were selected. The probe was labeled with the reporter dye 6-carboxyl-flurescein (FAM) at 5'end and with the non-fluorescent Black Hole Quencher Dye (BHQ) at the 3' end.

TaqMan Real Time PCR Assay

The real time PCR amplification was performed using StepOnePlus Real Time PCR System (Applied Biosystems) in 10 μl volume. Each reaction mixture comprised of 5 μl of TaqMan® Universal Master Mix II (Applied Biosystems) with the uracil-N-glycosylase (UNG), 200 nM of each primers and 250 nM of fluorogenic probe. 4 ul of each template sample was added in the reaction mixture. The real time PCR cycling conditions were as following: 50° C. for two min for UNG treatment, 95° C. for 10 minutes to denature the UNG and activate the DNA polymerase, 40 cycles of 15 seconds at 95° C. and 1 minute at 60° C. Each data point was run in triplicate with negative and positive controls. The obtained data was analyzed in the form of threshold cycle (Ct) values (Tables 3 and 4).

Preparation of the Standard Amplification Curves

The standard amplification curves were generated for the DNA extracted from the mycobacterial cells. The DNA concentration was determined by measuring the sample absorbance at 260 nm using the NanoDrop ND 1000 spectrophotometer (NanoDrop Technologies Inc.). Serial 10 fold dilutions of the cell suspension were made starting from $OD_{600}$ of 0.25 (2.4×10⁷ cfu/ml). The cells were sonicated for 5 min (Branson Ultrasonics 1510, 40 kHz frequency) before measuring the optical density.

Calculation of the Recovery Rate

The recovery rate (RR) was calculated using the following equation:

$$RR(\%) = 100 \cdot \frac{Ct_0}{Ct_c}$$

$Ct_0$ is the maximal theoretical Ct value corresponding to the total amount of DNA in the aliquot of the spiked sample. This value was calculated on the basis of the standard curve obtained for the pure DNA samples in PBS. $Ct_c$ is the Ct value obtained for the DNA preparation obtained from the washed beads used to pre-concentrate the cells from the aliquot of the spiked sample. Standard curves were made for each experiment and the recovery rates were calculated from the respective standard curves.

Results

Capture of Mycobacterial Cells by the Gp10 Functionalized Dynabeads

Cells of *M. avium* subsp. *paratuberculosis* ATCC 19851, *M. avium* subsp. *paratuberculosis* ATCC 19698, *M. marinum* ATCC 927, *M. smegmatis* mc²155 and *E. coli* BL21 (DE3) were used. A homogeneous suspension (2.4×10⁷ cfu/ml) was prepared for the each type of cells. Mycobacterial cells aggregate into the clumps of different size because the surface of these cells is hydrophobic. To get a homogeneous suspension, mycobacterial cells were sonicated for 5 min prior to the incubation with the magnetic beads. Sonication step prevented the non-specific deposition of the aggregated mass of mycobacterial cells onto the surface of the beads. Cells were incubated with the Gp10 functionalized beads. A magnet was used to quickly pull down the beads to the tube wall. This procedure allowed an easy removal of the supernatant by pipette.

Figure 6:
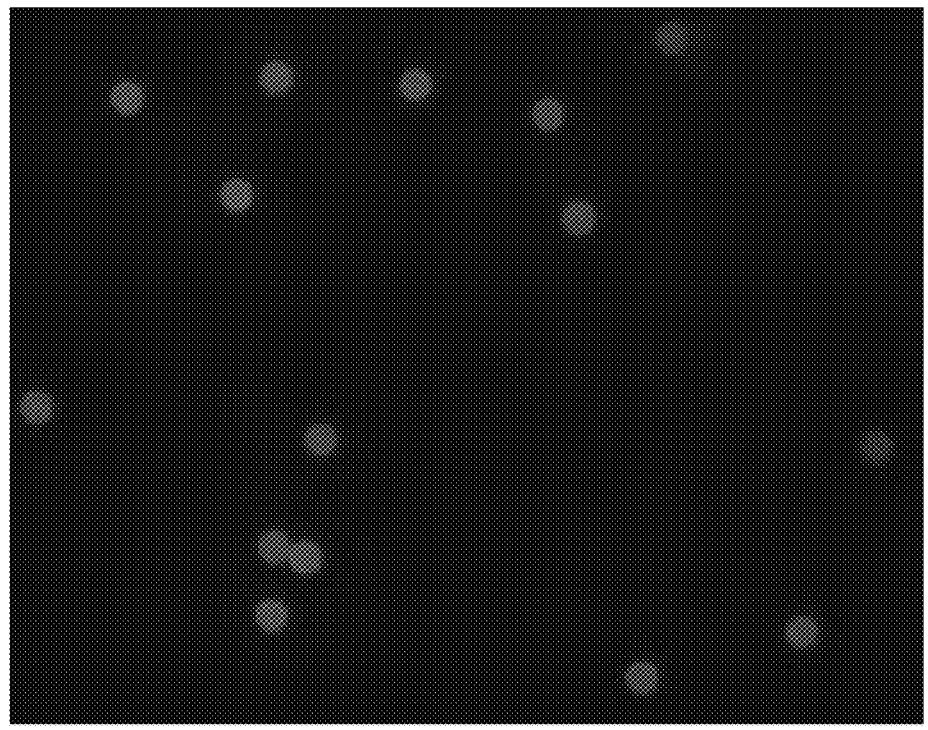
FIG. 6: Fluorescence microscopy images of *Mycobacterium* species capture by the Dynabeads M-280 bearing immobilized Gp-10. i) The tosylactivated DynabeadsM-280 were not functionalized with RBP. Only the background autofluorescence of the beads is detected; ii) *Mycobacterium avium* subsp. *paratuberculosis* ATCC 19851 capture by the Dynabeads M-280 bearing immobilized Gp-10. The tosylactivated Dynabeads were activated with Gp-10 RBP prior to incubation with MAP; iii) *M. avium* subsp. *paratuberculosis* ATCC 19698 capture by the Dynabeads M-280 bearing immobilized Gp-10. The tosylactivated Dynabeads were activated with Gp-10 RBP prior to incubation with MAP; iv) *M. smegmatis* mc$^2$155 capture by the Dynabeads M-280 bearing immobilized Gp-10. The tosylactivated Dynabeads were activated with Gp-10 RBP prior to incubation with MAP; v) *E. coli* BL21(DE3) cells served as a negative control. No capture of *E. coli* BL21(DE3) cells was observed.
Figure 6:
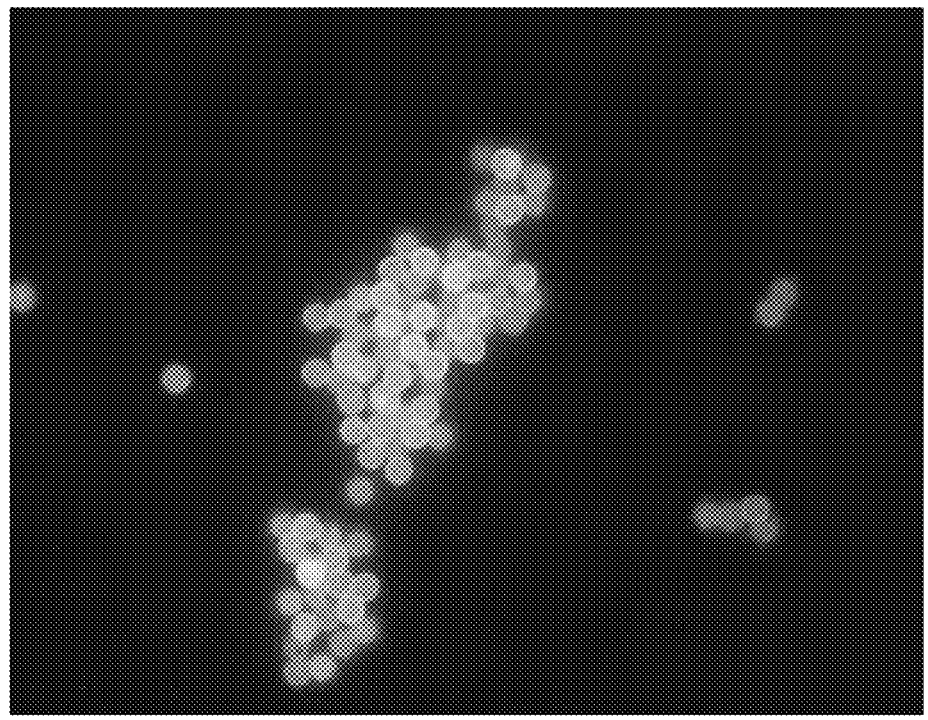
Figure 6:
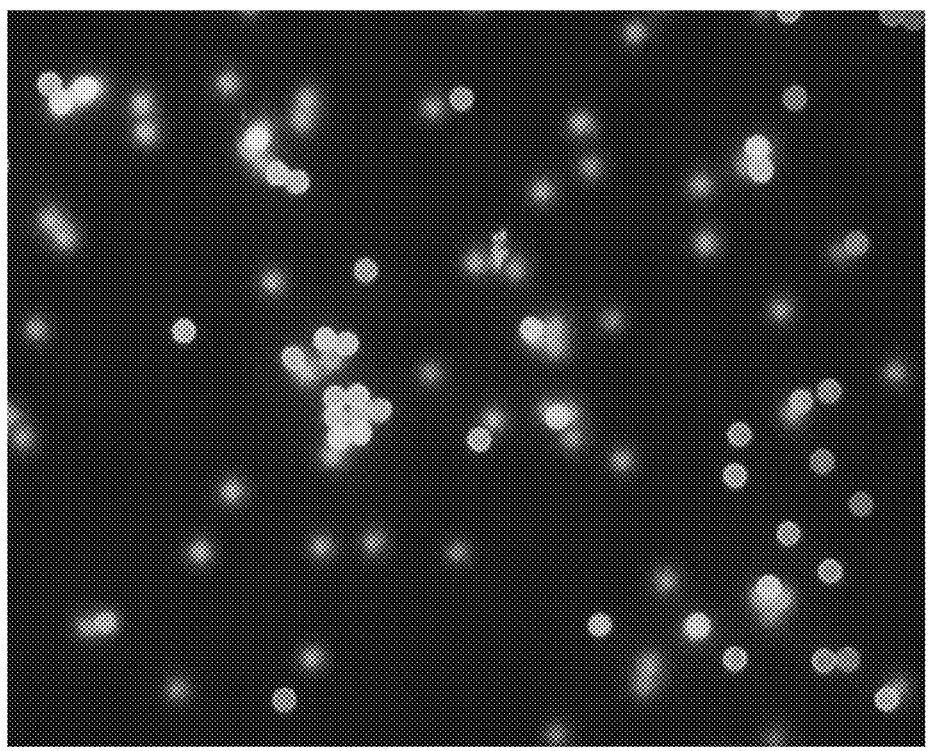
Figure 6:
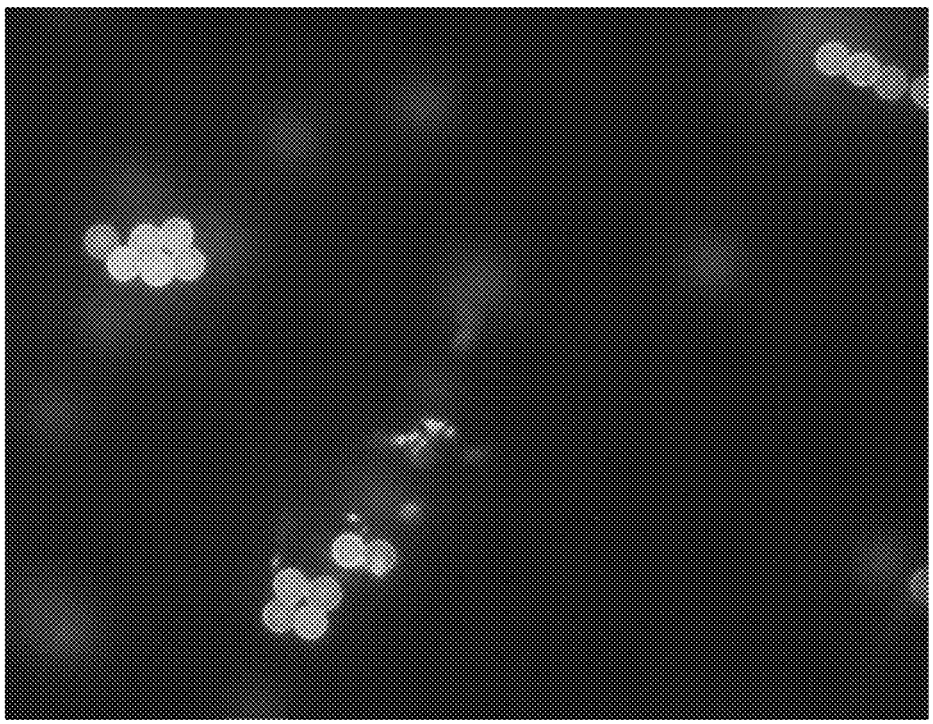
Figure 6:
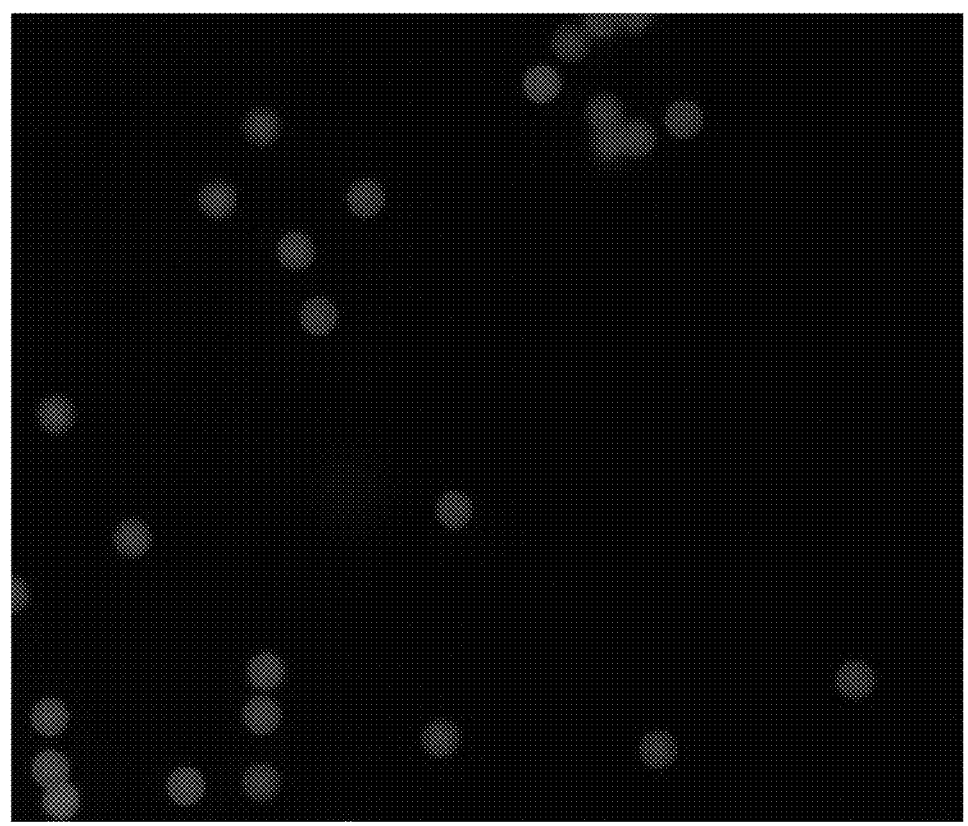
Figure 7:
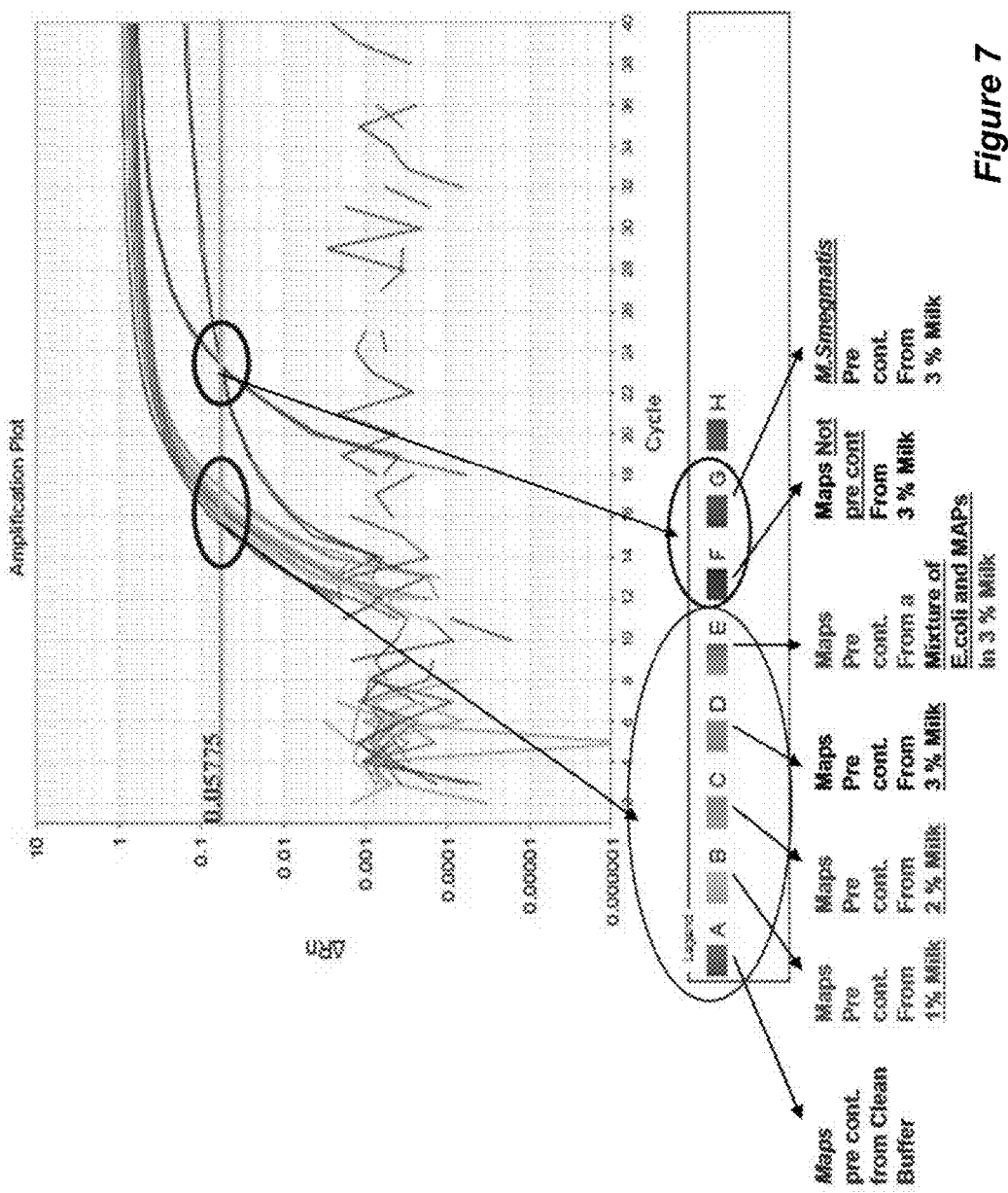
FIG. 7: Results of RT-PCR analysis of liquid samples containing mycobacteria. Amplification plots of different samples are shown in different colours: pre-concentrated *Mycobacterium avium* subsp. *paratuberculosis* ATCC 19851 sample from clean buffer, pre-concentrated *Mycobacterium avium* subsp. *paratuberculosis* ATCC 19851 samples isolated from 1, 2 and 3 percent of milk, a pre-concentrated sample of a mixture of *Mycobacterium avium* subsp. *paratuberculosis* ATCC 19851 and *E. coli* isolated from 3 percent milk, a non-preconcentrated *Mycobacterium avium* subsp. *paratuberculosis* ATCC 19851 sample isolated from 3 percent milk, and a pre-concentrated *Mycobacterium*

The fluorescence microscopy showed that, *M. avium* subsp. *paratuberculosis* ATCC 19851, *M. avium* subsp. *paratuberculosis* ATCC 19698 and *M. smegmatis* mc²155 (FIG. 6 ii-iv, respectively) cells were captured by the Gp10 functionalized magnetic beads. *E. coli* BL21(DE3) cells served as a negative control. No capture of *E. coli* BL21 (DE3) cells was observed (FIG. 6v). Additional negative control experiments were performed using *M. marinum*. It was concluded that the immobilized Gp10 can be efficiently used to capture the mycobacterial cells from suspension. Yet, an additional step was needed to distinguish between MAP and *M. smegmatis* cells extracted by the functionalized beads.

Specific Detection of MAP in the Artificially Contaminated Milk

Figure 8A:
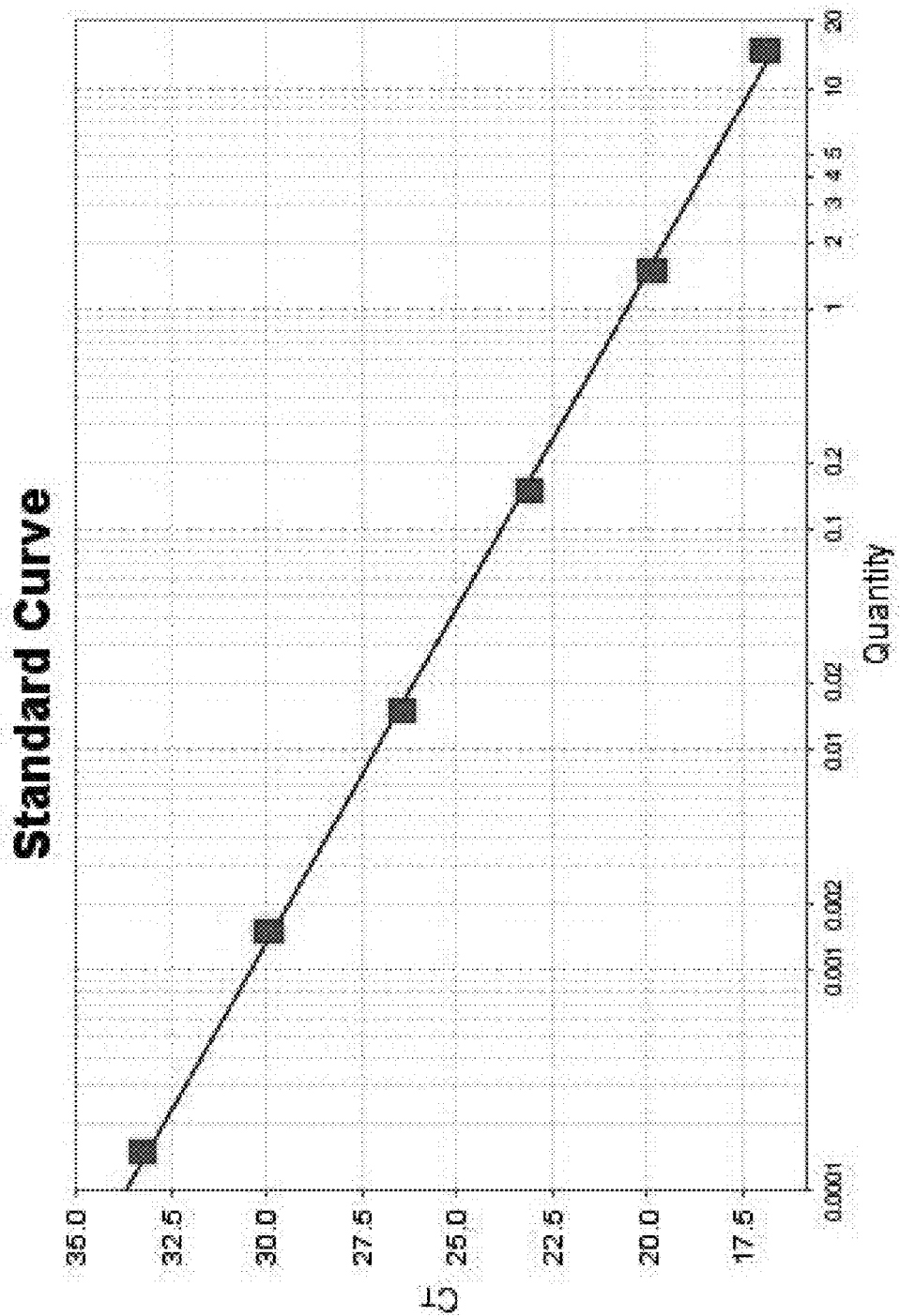
FIG. 8: Real time PCR based detection of the mycobacterial target sequence F57. A) Standard DNA amplification curve for the 10-fold dilution series of *M. avium* subsp. *paratuberculosis* ATCC 19851. Genomic DNA was obtained from $2.4 \times 10^1$ to $2.4 \times 10^7$ cells per reaction. Each dot represents the results of four data point amplifications for each dilution. The slope of the regression curve is −3.295 and the $R^2$=0.99. B) Amplification plot for the standard curve shown on panel A.
Figure 8B:
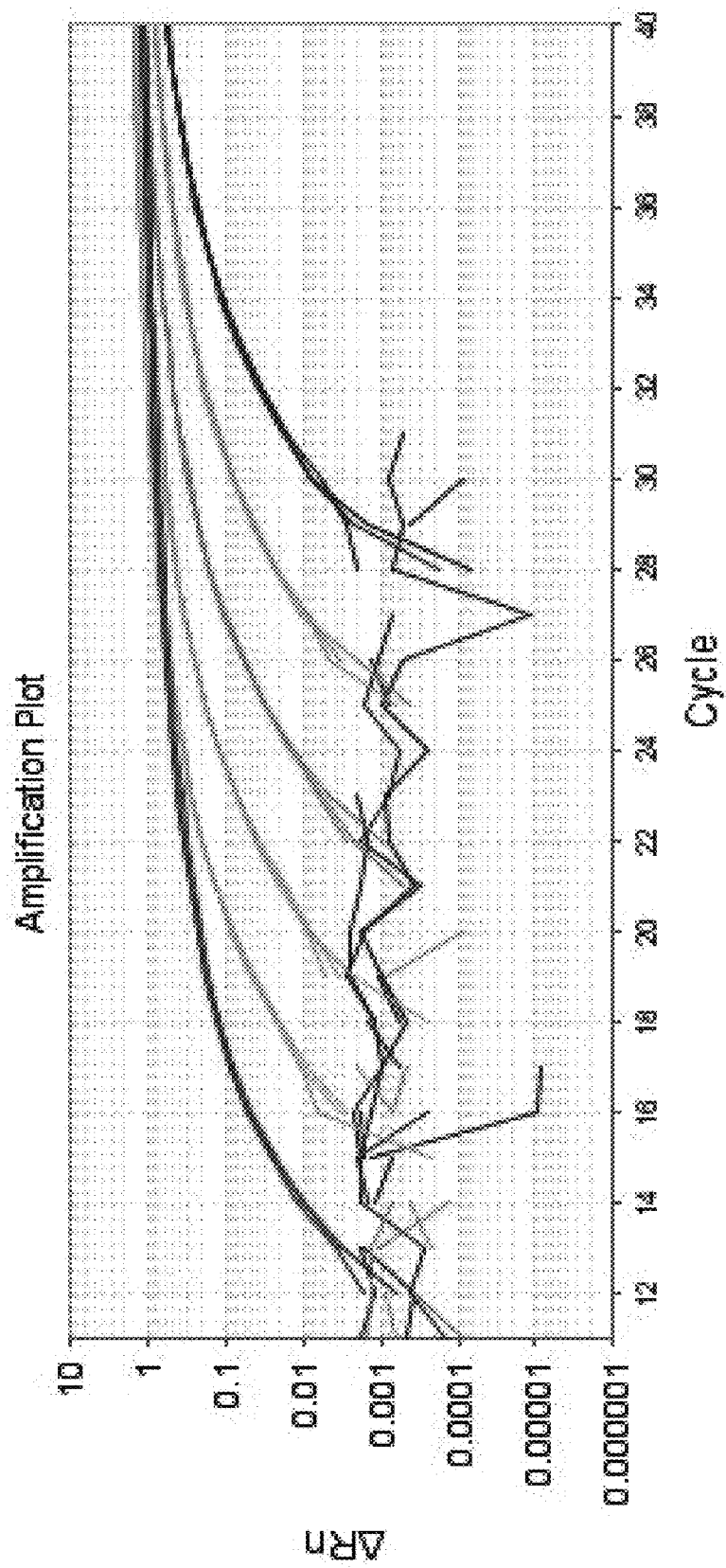
Figure 9A:
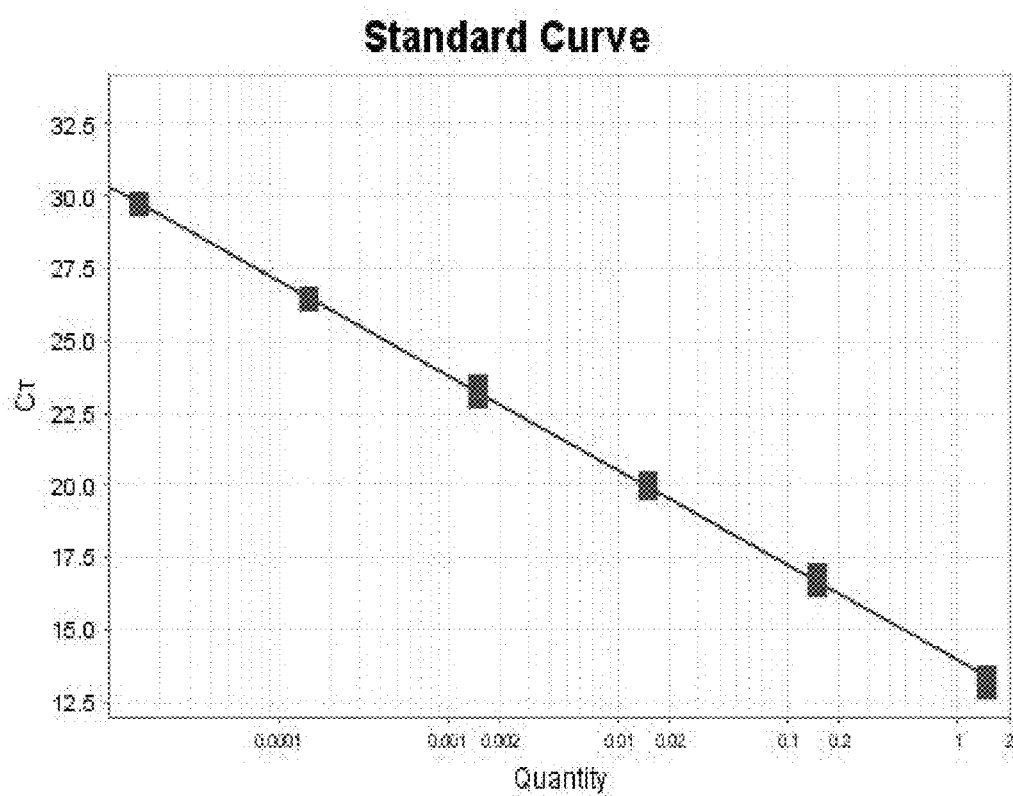
FIG. 9: Real time PCR based detection of the mycobacterial target sequence IS900. A) Standard DNA amplification curve for the 10-fold dilution series of *M. avium* subsp. *paratuberculosis* ATCC 19851. Genomic DNA was obtained from $2.4 \times 10^1$ to $2.4 \times 10^7$ cells per reaction. Each dot represents the results of four data point amplifications for each dilution. The slope of the regression curve is −3.282 and the $R^2$=0.99. B) Amplification plot for the standard curve shown on panel A.
Figure 9B:
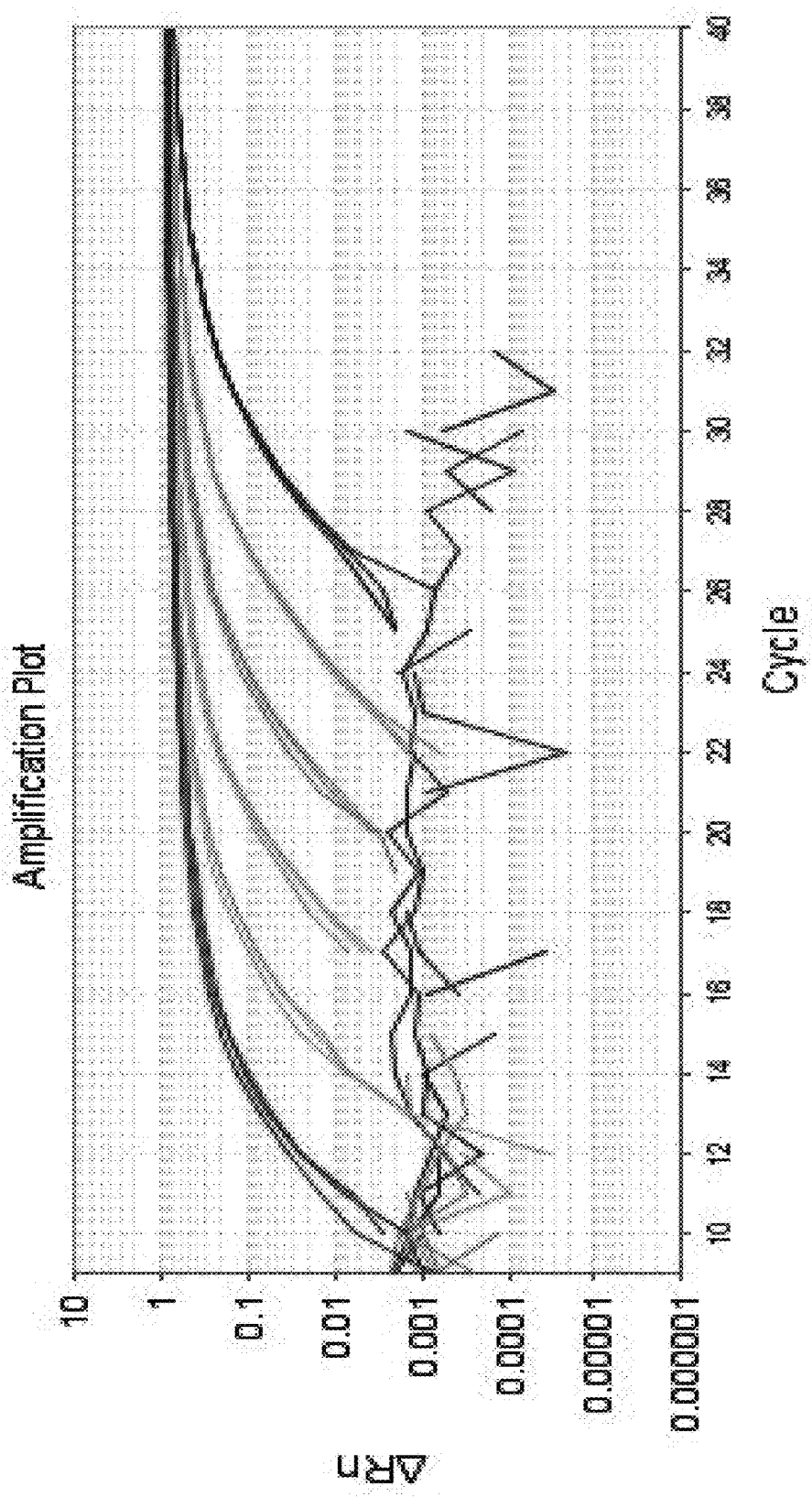

The real time PCR assay was evaluated using a known concentration of MAP cells. Two types of target sequences, F57 and IS900, were used to validate the specificity as well as the sensitivity of the assay. The standard curves of the real time PCR analysis maintained a linear character for up to six orders of magnitude of the cellular concentration, i.e. from 2.4×10¹ cfu/ml to 2.4×10⁷ cfu/ml. These standard curves showed a $R^2$ value of 0.99 and slope of −3.295 for the F57 sequence (FIG. 8A,B). For the IS900 target, the standard curve has shown similar characteristics with $R^2$ value of 0.99 and a slope of −3.282 (FIG. 9A,B). No increase in fluorescence was observed above the base level in the reagent control (no template) samples.

Lysin-Dynabeads based cell pre-concentration method was coupled with the real time PCR to quantify MAP in the milk spiked with the MAP cells. The Ct values turned out to be the lowest for the pre-concentrated samples (Tables 3 and 4). *M. marinum* ATCC 927, *M. smegmatis* mc$^2$155 and *E. coli* BL21(DE3) were used as reference to check the specificity of the method (data not shown). One can conclude that MAP cells can be easily pulled out from a complex environment contaminated with other bacteria. Also, MAP cells can be easily discriminated from the other mycobacteria when the suggested two-step protocol is used. Notably, in all cases the recovery rates of the samples pre-concentrated from the milk were close to those of the PBS-based samples whereas the recovery rates of the non-concentrated milk samples were considerably lower. This result indicates that the described protocol increases the sensitivity of the PCR based detection of MAP cells in milk.

Comparison Between the Ct Values of the Two Target Sequences

There are 14-20 copies of IS900 per MAP genome, which allows a high level of sensitivity for the PCR based detection. However, specificity of the IS900 became questionable when a DNA sample of slow growing non-pathogenic environmental *Mycobacterium cookii* has shown strong amplification. Considering this limitation of IS900, other target sequences have been suggested. We tested one of them, a F57 sequence, in combination with our pre-concentration protocol. The highest recovery rate was 85% when MAP cells were pre-concentrated and 55% when the cells were not pre-concentrated and the target sequence IS900 was used (Table 3). The highest recovery rate was 80% for the pre-concentrated MAP cells and 44% when the cells were not pre-concentrated and the target sequence F57 was used (Table 3). Similar experiments were done for the other strain of MAP (Table 4). Again, the highest recovery rate was 95% for the pre-concentrated cells and 58% for the non pre-concentrated cells hen the IS900 sequence was used. The highest recovery rate was 93% when the cells were pre-concentrated and 53% for the non pre-concentrated cells when the F57 sequence was targeted. Thus, our pre-concentration protocol can be successfully applied for the PCR analysis where several target sequences are used as the additional safeguard to ensure a reliable discrimination between MAP and other mycobacteria.

The traditional and most reliable method for MAP detection is cell culture combined with PCR. However, MAP is a slow growing bacterium: it takes 25 days and the special expensive medium to grow. It is demonstrated in the present work that the pre-concentration of the MAP cells using the immobilized phage lysin followed by PCR based analysis is a rapid, highly specific, sensitive and robust process of MAP cell detection. MAP cells were effectively extracted from the artificially contaminated milk and were successfully discriminated from the other species of mycobacteria. Remarkably, long culturing step was eliminated and a validated real time PCR approach could still be used to achieve the clinically approved golden standard of detection. The developed protocol can be transformed into a robotized high throughput format. Also, the described method can be applied for the detection of the other *M. avium* subspecies. Indeed, *M. avium* is a serious human pathogen causing extensive lung damage and disseminated infections in immunocompromised individuals and cystic fibrosis patients.

Summary of Example 5

Recombinant lysin Gp10 from the mycobacteriophage L5 was coupled to the magnetic Dynabeads 280 and these beads were used to capture *Mycobacterium avium* subsp. *paratuberculosis* (MAP) cells from the complex media. Skim cow milk spiked with MAP cells, skim milk spiked with both MAP and *Escherichia coli* cells and Middlebrook 7H9 medium spiked with MAP cells were used to model the contaminated food matrices. The beads bearing the immobilized Gp10 were incubated with the samples, separated, washed, subjected to the DNA extraction procedure and the obtained solution was analyzed by the real time PCR. The entire process was completed within 24 hours, demonstrated high specificity towards the MAP cells and increased the sensitivity of detection. The recovery rates for the samples pre-concentrated from the complex media were close to those of the buffer-based samples whereas the recovery rates for the non-concentrated milk samples were considerably lower. The protocol was successfully tested with two MAP strains (ATCC 19698 and 19851) and two target sequences (IS900 and F57). The methods provided herein eliminate the need for the 25 day long culturing step used in traditional protocols and allows the pre-concentration of the MAP cells to get rid of the various PCR inhibitors that may be present in the food matrices. The developed protocols and methods are instrumental for the prevention, diagnostics and monitoring of gastric diseases such as Johne's and Crohn's diseases in cattle and humans, respectively.

TABLE 2

Primers and probes used in Example 5.

| Primers/Probes | Target sequence IS900 | Target sequence F57 |
|---|---|---|
| Forward Primer | 5'-TGACGGTTACGGAGGTGGTT-3' (SEQ ID NO: 7) | 5'-CGGTCCAGTTCGCTGTCAT-3' (SEQ ID NO: 8) |
| Reverse Primer | 5'-ATGCAGTAATGGTCGGCCTTA-3' (SEQ ID NO: 9) | 5'-CACGCAGGCATTCCAAGTC-3' (SEQ ID NO: 10) |
| Taqman Probe | 5'-TGGCACAACCTGTCTG-3' (SEQ ID NO: 11) | 5'-ACGGGAAGGGTGGTC-3' (SEQ I NO: 12) |

Table 3. Recovery rates of *M. avium* subsp. *paratuberculosis* ATCC 19851 by the Gp10 functionalized magnetic beads and the Ct values of the different samples. "ND"—not determined.

| Serial number | Sample type | Real time PCR (Ct) Target gene IS900 | % Recovery | Real time PCR (Ct) Target gene F57 | % Recovery |
|---|---|---|---|---|---|
| 1. | Mycobacterium avium subsp. paratuberculosis ATCC 19851 Preconcentrated from PBS | 15.5 ± 0.18 | 85.5% | 19.9 ± 0.27 | 80.4% |
| 2. | Mycobacterium avium subsp. paratuberculosis ATCC 19851 Preconcentrated from 1% milk | 15.9 ± 0.012 | 81.76% | 20.6 ± 0.15 | 77.6% |
| 3. | Mycobacterium avium subsp. paratuberculosis ATCC 19851 Preconcentrated from 2% milk | 16.7 ± 0.14 | 77.8% | 21.5 ± 0.22 | 74.41% |
| 4. | Mycobacterium avium subsp. paratuberculosis ATCC 19851 Preconcentrated from 3% milk | 16.5 ± 0.083 | 78.78% | 21.3 ± 0.31 | 75.11% |
| 5. | Mixture of E. coli and Mycobacterium avium subsp. paratuberculosis ATCC 19851 Preconcentrated from 3% milk | 17.3 ± 0.049 | 75.14% | 22.15 ± 0.1 | 72.22% |
| 6. | Mycobacterium avium subsp. paratuberculosis ATCC 19851 in 3% milk (not concentrated) | 23.5 ± 0.29 | 55.3% | 35.7 ± 0.27 | 44.81% |
| 7. | Mycobacterium smegmatis mc2155 Preconcentrated from 3% milk | 23.3 ± 0.059 | ND | 28.2 ± 0.10 | ND |

TABLE 4

Recovery rates of *M. avium* subsp. *paratuberculosis* ATCC 19698 by the Gp10 functionalized magnetic beads and the Ct values of the different samples. "ND"-not determined

| Serial number | Sample type | Real time PCR (Ct) Target gene IS900 | % Recovery | Real time PCR (Ct) Target gene F57 | % Recovery |
|---|---|---|---|---|---|
| 1. | Mycobacterium avium subsp. paratuberculosis ATCC 19698 Preconcentrated from PBS | 13.9 ± 0.044 | 93.53% | 18.9 ± 0.33 | 84.64% |
| 2. | Mycobacterium avium subsp. paratuberculosis ATCC 19698 Preconcentrated from 1% milk | 13.7 ± 0.18 | 94.8% | 18.6 ± 0.31 | 86.02% |
| 3. | Mycobacterium avium subsp. paratuberculosis ATCC 19698 Preconcentrated from 2% milk | 13.8 ± 0.14 | 98.2% | 38.6 ± 0.30 | 86.9% |
| 4. | Mycobacterium avium subsp. paratuberculosis ATCC 19698 Preconcentrated from 3% milk | 13.9 ± 0.035 | 93.5% | 18.8 ± 0.25 | 85.1% |
| 5. | Mixture of E.Coli and Mycobacterium avium subsp. paratuberculosis ATCC 19698 Preconcentrated from 3% milk | 13.6 ± 0.37 | 95.5% | 17.1 ± 0.2 | 93.5% |
| 6. | Mycobacterium avium subsp. paratuberculosis ATCC 19698 to from 3% milk (not concentrated) | 22.08 ± 0.30 | 58.87% | 29.8 ± 0.4 | 53.69% |
| 7. | Mycobacterium ATCC 927 | 30.6 ± 0.22 | ND | 35.8 ± 0.25 | ND |

TABLE 4-continued

Recovery rates of *M. avium* subsp. *paratuberculosis* ATCC 19698 by the Gp10 functionalized magnetic beads and the Ct values of the different samples. "ND"-not determined

| Serial number | Sample type | Real time PCR (Ct) Target gene IS900 | % Recovery | Real time PCR (Ct) Target gene F57 | % Recovery |
|---|---|---|---|---|---|
| 8. | *Mycobacterium smegmatis* m$^c$2155 ATCC 19698 Preconcentrated from Complex media | 33.9 ± 0.195 | 93.5% | 17.1 ± 0.02 | 93.5% |

Example 6: Bacteriophage Cell Binding Proteins for the Detection of Mycobacteria This study represents an attempt to develop rapid diagnostic probes for mycobacteria using mycobacteriophage L5 host envelope binding proteins. Phage L5 of the Siphoviridae family is one of the best studied mycobacterial phages. Its genome sequence was the first obtained for a temperate non-*Escherichia coli* phage. L5 virions have a long non-contractile tail and contain 52 297 bp of double-stranded linear DNA. Luciferase-expressing L5 phage was also proposed to be useful for the detection of live mycobacteria. L5 phage was initially described as having a broad host range, including *M. avium*, although it is much more effective in infecting fast growing *Mycobacterium smegmatis* and requires special conditions to infect slow growing mycobacteria. We found that the minor tail protein Gp6 and lysin Gp10 may tightly bind to the host cell surface Immobilized Gp10 was able to bind both MAP and *M. smegmatis* cells whereas Gp6 was *M. smegmatis* specific. Neither of the two proteins was able to capture *M. marinum* cells. Magnetic beads covered with the recombinant Gp10 were used as a tool to specifically pre-concentrate MAP cells. The latter approach demonstrates the successful use of mycobacteriophage proteins at the pathogen capturing step, which can potentially be used to improve the effectiveness of existing MAP diagnostic platforms.

Materials and Methods

Bacteria and Phage Strains Used.

Mycobacteria phage L5 (HER-386) was obtained from the Felix D'Herelle Reference Centre for Bacterial Viruses (Laval University, Quebec, Canada). *Mycobacterium marinum* ATCC number 927, *M. smegmatis* mc$^2$ 155 and *M. avium* subsp. *paratuberculosis* ATCC 19851 were used in the binding studies along with *Campylobacter jejuni* NCTC 11168H, *Salmonella enterica* subsp. *enterica* sv. *Typhimurium* ATCC 19585 and *E. coli* K-12. *E. coli* DH5α (Invitrogen) and *E. coli* BL21(DE3) (Invitrogen) were used for cloning and recombinant protein expression procedures, respectively. All mycobacterial strains were grown in ambient atmosphere. Middlebrook 7H9 (BD Biosciences) broth supplemented with oleic acid-albumin-dextrose catalase (BD Biosciences) and mycobactin J (Allied Monitor Inc.) was used to propagate *M. smegmatis* at 37° C. for 48 hrs as well as MAP cells at 37° C. for 10 days. *M. marinum* was grown for 10 days at 37° C. using Middlebrook 7H9 (BD Biosciences) broth supplemented with oleic acid-albumin-dextrose catalase (BD Biosciences). *C. jejuni* cells were grown for 18 h under microaerobic conditions (10% $CO_2$, 5% $O_2$, 85% $N_2$) at 37° C. on agar plates with Mueller-Hinton medium (BD Biosciences). LB medium (BD Biosciences) was used to propagate *S. Typhimurium* and *E. coli* strains overnight at 37° C. unless stated otherwise. LB medium containing 25 µg/ml of kanamycin (BioShop Canada Inc.) was used for cloning and protein production procedures.

Bioinformatic Analysis.

The mycobacterial phage L5 genome that is deposited in the National Center for Biotechnology Information (NCBI, USA) database was used as a source of entry data (NCBI reference sequence NC_001335.1). Standard Basic Local Alignment Search Tool (BLAST) analysis was performed using the web service offered by NCBI. Protein Homology/analogY Recognition Engine (PHYRE), version 2.0 software was also used to analyze the amino acid sequence of the L5 mycobacteriophage proteins to choose the RBP candidates.

Gene Manipulations.

The genes of putative mycobacteriophage L5 RBPs were cloned between the EcoRI and HindIII sites in the pET-30a (+) plasmid (Novagen) as follows. The corresponding genes were amplified by PCR directly from the phage L5 suspension. Taq DNA polymerase (Fermentas) was used for the PCR that was performed using 3 µl of phage lysate per 50 µl of reaction mix in the presence of 0.1 mg/ml of BSA (Fermentas). EcoRI and HindIII restriction sites were introduced during the PCR at the 5' and 3' ends. Primers GGCATCGAATTCATGGCCGACCTCGGCAAC-CCACTCG (SEQ ID NO: 13) and GATGCTAAGCTTT-TACCTCGGCTGTCGGTAAACGCGGC (SEQ ID NO: 14) were used for the amplification of gene 6 as forward and reverse primers, respectively. Primers GGCATCGAAT-TCATGACCTTCACAGTCACCCGCGAG (SEQ ID NO: 15) and GATGCTAAGCTTTCATAGGCCACCTCTTTCT-GCGATG (SEQ ID NO: 16) were used for the amplification of gene 10 as forward and reverse primers, respectively. All four primers were procured from Integrated DNA Technologies. The PCR cycling conditions were: 95° C./2 min, followed by 30 cycles of 95° C./30 sec, 55° C./30 sec, 72° C./1 min and a final elongation step of 72° C./10 min PCR amplification resulted in a single product for each gene. The PCR products were purified directly from the reaction mixture using the GeneJet plasmid Miniprep spin column kit (Fermentas). The resulting DNA was digested with EcoRI and HindIII restriction enzymes (Fermentas) and re-purified with the spin column kit. pET-30a(+) plasmid (Novagen) was digested with the same restriction enzymes and the linear plasmid was purified by the same way as described above. Finally, the restrictase-treated DNA of genes 6 and 10 was ligated with the linearized pET-30a(+) plasmid using T4 DNA ligase (Fermentas). *E. coli* DH5α strain was transformed with the ligation product. The resulting plasmid was then purified using GeneJet plasmid Miniprep spin column kit (Fermentas). Product integrity was confirmed by sequencing of the insert performed by the Molecular Biology Service Unit, Department of Biological Sciences, University of Alberta.

Protein Production.

His6-tagged Gp6 ('His6' disclosed as SEQ ID NO: 17) and Gp10 proteins were expressed in E. coli BL21 cells transformed with the pET-30a(+) plasmid containing either gene 6 or gene 10. Cells were grown at 30° C. to an $OD_{600}$ of 0.5, induced with 0.2 mM IPTG and incubated overnight at room temperature with shaking. Cells were harvested, disrupted by sonication and the soluble fraction was subjected to the standard immobilized metal affinity chromatography (IMAC) procedure. Briefly, cells were resuspended in IMAC buffer A (50 mM sodium phosphate, pH 8.2, 1 M NaCl, 30 mM imidazole) with the Complete Mini, EDTA-free protease inhibitor cocktail (Roche) and then disrupted by sonication. Cell debris was removed by centrifugation at 27000 g for 30 min. The soluble fraction was filtered through 0.22 μm filter (Millipore) and loaded onto the 1 ml HisTrap HP column (GE Healthcare). The column was washed with 20 column volumes of buffer A and the target protein was eluted with buffer A plus 500 mM imidazole. Both Gp6 and Gp10 proteins were subsequently dialyzed against PBS (phosphate-buffered saline, 1.8 mM $KH_2PO_4$, 10 mM $Na_2HPO_4$, pH 7.4, 2.7 mM KCl, 137 mM NaCl). The protein concentration was determined by measuring the absorbance at 280 nm Extinction coefficients were calculated for the recombinant fusion proteins using ProtParam Tool (www.expasy.org) assuming all cysteine residues to be in the reduced state: 43430 $M^{-1}$ $cm^{-1}$ and $A_{0.1\%}$ of 1.093 for the His-tagged Gp6 and 53400 $M^{-1}$ $cm^{-1}$ and $A_{0.1\%}$ of 1.402 for the His-tagged Gp10. $A_{280}/A_{260}$ ratio was in the range of 1.8-1.9 for both protein preparations.

The insoluble fraction of Gp10 was assessed as follows. A 100 μl sample of cell debris obtained after cell disruption was washed three times with 1 ml of ice-chilled PBS and extracted with 0.5 ml of PBS/8 M urea for 2 hrs at 4° C. with gentle mixing. Then the insoluble debris was removed by centrifugation (20 min at 18 000 g at 4° C.) and an aliquot of the supernatant was diluted 20 times by the SDS-PAGE sample buffer (50 mM Tris-HCl, pH 6.8, 2% SDS, 10% glycerol, 0.02% bromphenol blue), heated for 2 min at 95° C. and analyzed by SDS-PAGE.

The solubilization and refolding of recombinant Gp10 was done as follows. Approximately 3 ml of cell debris was washed three times with 30 ml of ice-chilled PBS containing the protease inhibitor cocktail. Then the debris was extracted with 10 ml of PBS/8 M urea for 2 hrs at 4° C. with gentle mixing. The insoluble fraction was removed by centrifugation (20 min at 18 000 g at 4° C.) and the supernatant was diluted 20 times by ice-chilled'/2 IMAC A buffer containing 30% glycerol followed by the overnight incubation at 4° C. The solution was cleared from the precipitated protein by centrifugation (20 min at 18 000 g at 4° C.) and the supernatant was subjected to IMAC as described above.

Protein Immobilization.

Proteins were immobilized onto cysteamine covered gold surfaces that were activated with glutaraldehyde according to the previously described protocol where RBP samples were used instead of whole phage particles. Briefly, the gold substrates were fabricated using piranha cleaned silicon substrates by sputtering a 25 nm thick gold layer. The gold substrates were sonicated in acetone, isopropanol, ethanol and MilliQ (Millipore) water for 5 min each prior to their use (Branson Ultrasonics 1510, 40 kHz frequency). The gold substrates were incubated overnight at 40° C. in a 50 mM solution of cysteamine hydrochloride (Sigma-Aldrich). The cysteamine self assembled monolayer (SAM) substrates were modified by 2% glutaraldehyde (Sigma-Aldrich) for 1 hr at room temperature and washed twice in PBS. These modified substrates were incubated in a 20 μg/ml solution of Gp10 (or Gp6) in PBS overnight at 60° C. The negative control substrate was incubated in PBS only. To block nonspecific binding of bacteria, the substrates were incubated in 1 mg/ml of bovine serum albumin (Sigma-Aldrich) and were washed twice in PBS. The protein covered substrates were exposed to $10^9$ cfu/ml of mycobacterial cells in PBS for 1 hr at room temperature. The immobilized surfaces were washed in 0.05 Tween 20 (Sigma-Aldrich) before analysis. For fluorescence microscopy, the bacterial cells were stained with 50 μM resazurin (Sigma-Aldrich) for 20 min before exposure to the substrates covered with the immobilized proteins.

Tosyl-activated Dynabeads (Invitrogen) were used for protein immobilization as described previously with the following modifications. Twenty μl of 100 mg/ml tosyl-activated beads were suspended in 1 ml of PBS and washed twice in sterile PBS. The beads were separated from any liquid suspension by using a magnet. The cleaned beads were incubated with 100 μg/ml Gp 10 and Gp 6 for 1 hr at 37° C. followed by overnight incubation at room temperature. The functionalized beads were further incubated in 1 mg/ml BSA in PBS for 30 min at room temperature to block the free surface and prevent non-specific binding. The beads were washed twice in PBS to remove the unbound BSA.

Cell Binding Assays.

Bacterial cell binding to the gold surface covered with the immobilized protein was assessed as described previously. Scanning electron microscopy (SEM) and fluorescent microscopy (FM) were used to estimate the number of bacterial cells bound to the surfaces. The samples were fixed with 2% glutaraldehyde for 2 hrs at room temperature followed by a gradient of ethanol from 50% to 100% before SEM. Finally the samples were dried by nitrogen gas. SEM imaging was performed using a Hitachi S-4800/LEO 1430 microscope. Cells were prestained using 50 μM of resazurin stain (Sigma-Aldrich) for the FM-based binding assay. An Olympus IX81 microscope equipped with a FITC filter and a Roper Scientific Cool-Snaps HQ CCD Camera were Used to Record the FM Images. ImageJ Software (USA NIH) was used to analyze the microscopy images. Average numbers of cells bound to the surface are indicated on the basis of the assessment of the cell number, fields of view, and using 8 gold covered chips per test.

MAP Cell Capture by Magnetic Beads Covered with Gp10.

Bead-mediated capture of mycobacteria was performed as described previously. Briefly, magnetic beads bearing immobilized Gp10 were washed with PBS and incubated with the suspension of MAP cells for 1 hr at room temperature with gentle shaking. The beads were separated by using a magnet and washed twice with sterile PBS. Beads were subsequently examined by FM to visually confirm the cell binding event.

Mass Spectrometry.

Chemically synthesized fragments of mycobacterial arabinans and phenolic glycolypids were used to test the carbohydrate binding ability of recombinant Gp6. Association constants ($K_a$) for Gp6 binding to carbohydrate ligands were measured using the direct electrospray ionization mass spectrometry (ESI-MS) assay. The assay is based on the direct detection and quantification of the abundance of ligand-bound and unbound protein ions in the gas phase. All binding measurements were carried out at 25° C. and pH 7.2 using a 9.4T ApexQe FTICR mass spectrometer (Bruker, Billerica, Mass.). ESI was performed in aqueous ammonium acetate (100 mM) solutions prepared from stock solutions of protein and oligosaccharide. The single chain variable fragment (scFv) of the monoclonal antibody Se155-4 was used as reference protein to distinguish specific from nonspecific ligand binding with the protein during the ESI-MS measurements.

Peptidoglycan Binding Assay.

Dehydrated peptidoglycan from *Bacillus subtilis* (Sigma-Aldrich) was suspended in water to obtain a 10 mg/ml stock that was stored at −20° C. This stock was diluted further in water to obtain a 1 mg/ml working stock solution that was used in the experiments and was prepared fresh each time. A 0.1 mg/ml sample of Gp10 in PBS was incubated with peptidoglycan at a final concentration of 0.1 mg/ml for 30 min at room temperature with occasional stirring. Then, the peptidoglycan was separated from the protein solution by centrifugation (15 min at 18 000 g at 4° C.), an aliquot of the supernatant was mixed with the SDS-sample buffer and analyzed by SDS-PAGE.

Results

Selection and Identification of Mycobacteriophage Cell Binding Proteins.

It has been shown that phages L5 and D29 infect *M. smegmatis* via mechanism(s) different from that used by the related phages Bxb1 and TM4. Yet, neither the RBP(s) nor the nature of the phage receptor has been described for any of these phages. Proteins described as minor tail proteins of phage L5 were chosen first as RBP candidates. Comparison of the L5 genome sequence with that of the D29, Bxb1 and TM4 phages was performed to reveal the possible RBP genes among the genes encoding tail proteins. Notably, the homolog of the gene encoding the L5 minor tail protein Gp6 (NCBI gene ID 2942962, protein ID NP_039673.1) was found in the genome of phage D29, but not in the genomes of Bxb1 and TM4. Thus, a possible involvement of Gp6 in adsorption of L5 phage to the host cells was predicted although no known functional domains were revealed by BLAST analysis of Gp6 amino acid sequence.

Interestingly, structure prediction done by Phyre2 revealed some similarity with galactose binding domains with a 45% model confidence score. The latter fact can indicate the ability of Gp6 to bind carbohydrates albeit not necessarily galactose-containing sugars. It is reasonable to expect that mycobacteriophage RBP(s) may possess carbohydrate binding properties taking into account the high amount of complex carbohydrates present in mycobacterial cell walls and the fact that many known phage RBPs do indeed target bacterial surface polysaccharides. Indeed, complex surface carbohydrates were shown to be the putative receptors of the mycobacteriophages.

It was predicted recently that gene 10 (NCBI gene ID 2942936, protein ID NP_039674.1) encodes a putative lysin with the N-terminal peptidase domain and C-terminal cell wall binding domain. Indeed, BLAST analysis of L5 Gp10 amino acid sequence annotated it as a putative lysin/peptidoglycan binding protein with the best E values in the range of $10^{-19}$ to $10^{-106}$. More detailed Phyre2 structure prediction searches confirmed this finding with a high model confidence score of 96%. Interestingly, while gene 10 is located apart from the gene cluster encoding most of the minor tail proteins in the L5 phage genome it is close to gene 6; these genes are separated only by the small genes 7-9 encoding tRNA. Thus, Gp6 and Gp10 were chosen as cell binding proteins to be recombinantly produced and tested for use as diagnostics for mycobacteria.

Production of Putative Mycobacteriophage Cell Binding Proteins.

Comparison of the nucleotide sequences of the cloned genes 6 and 10 with that available in the NCBI database revealed the presence of point mutations that resulted in the corresponding amino acid substitutions. Gene 6 had a T44C mutation that led to the L15P amino acid substitution in the recombinant protein. Gene 10 had two point mutations C95T and A670G, which resulted in the amino acid substitutions T32I and I224V. Use of the non-proofreading Taq DNA polymerase was the probable reason for the appearance of these mutations, which were limited to pyrimidine/pyrimidine and purine/purine substitutions. No similar substitutions were found among the sequences of the closely related homologs deposited in the NCBI database.

Figure 10:
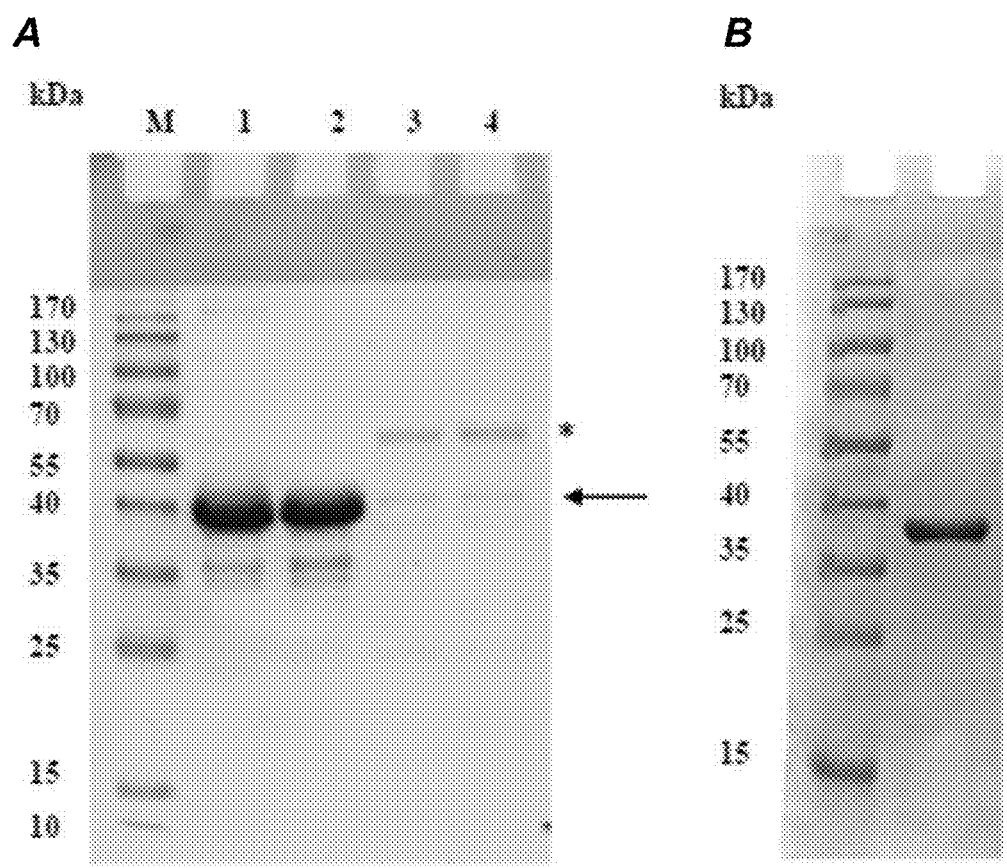
FIG. 10: SDS-PAGE analysis of recombinant Gp6 and Gp10. A) Comparison of the yield and properties of soluble Gp6 and Gp10. Both samples were obtained from the same volumes of expression cultures using the same IMAC protocol. M, molecular weight markers; lane 1, Gp6 sample incubated in SDS-PAGE sample buffer with 2% SDS for 10 min at room temperature; lane 2, same as lane 1, but sample was preheated at 95° C. for 10 min; lanes 3 and 4 are similar to lanes 1 and 2 but Gp10 samples were used. The arrow indicates the expected position of recombinant Gp10; the asterisk labels the ca. 60 kDa contaminant; B) Gp10 protein sample obtained by 8 M urea extraction of the insoluble cell pellet.
Figure 11A:
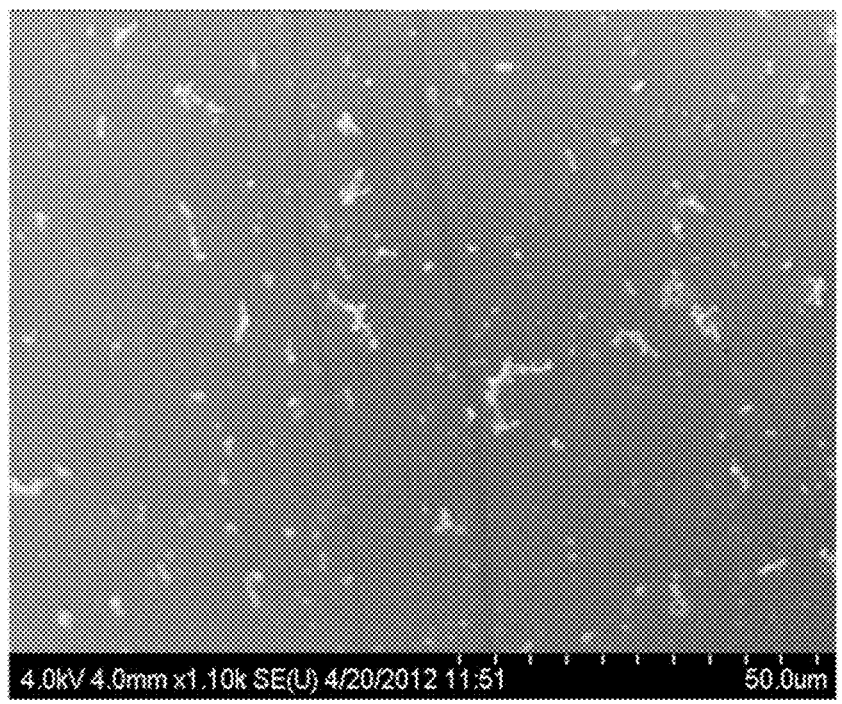
FIG. 11: Images of M. smegmatis, MAP and M. marinum cells captured by the recombinant Gp6 protein immobilized on gold surfaces (both SEM and FM images are shown for the same experiment). A) gold surface treated with 20 µg/ml of Gp6 and incubated with M. smegmatis cells; B) same as A but MAP cells were used; C) same as A but with M. marinum cells; D) the surface was treated in a same way as in A except that it was not exposed to the recombinant protein prior to incubation with M. smegmatis cells.
Figure 11A:
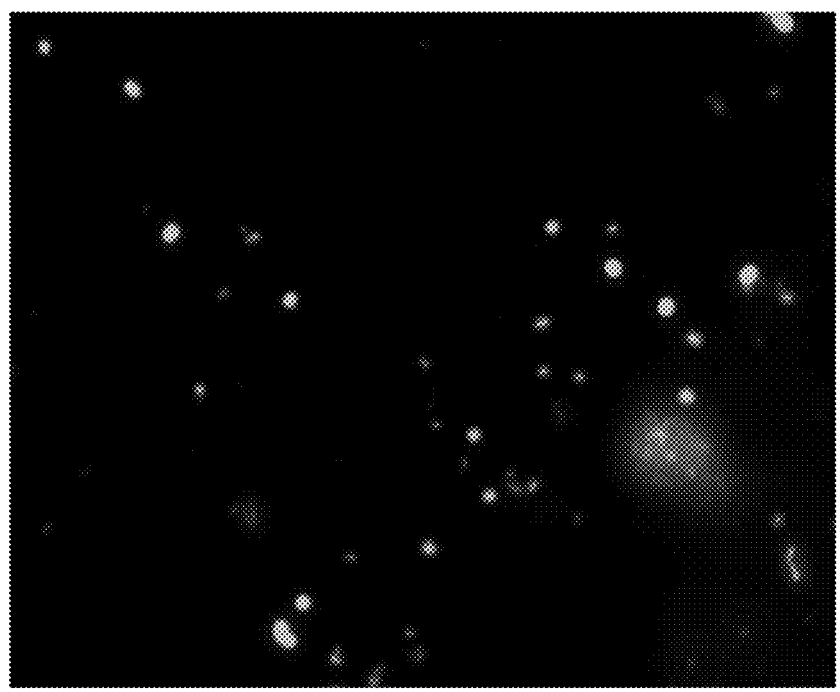
Figure 11B:
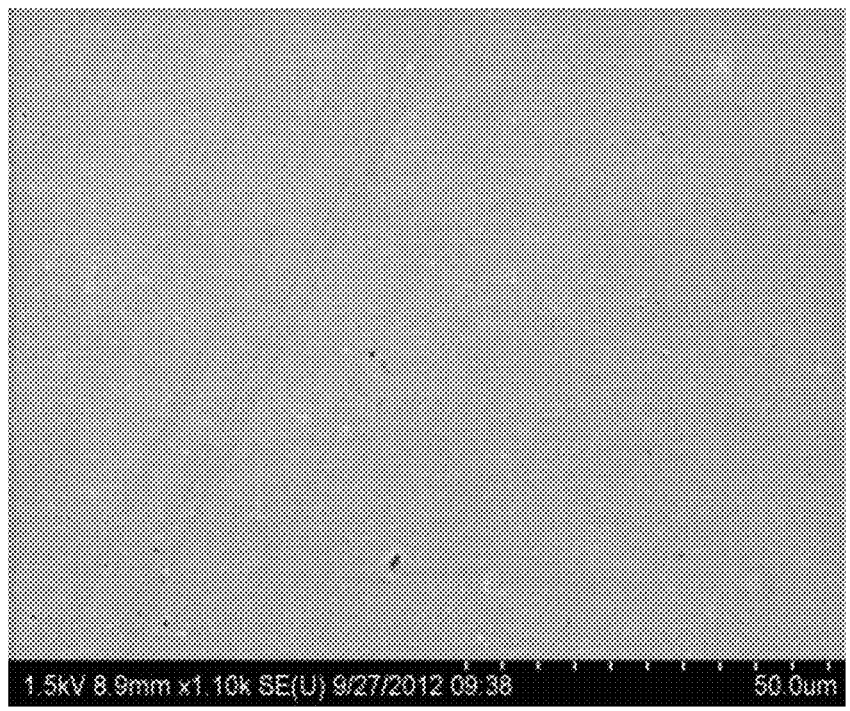
Figure 11B:
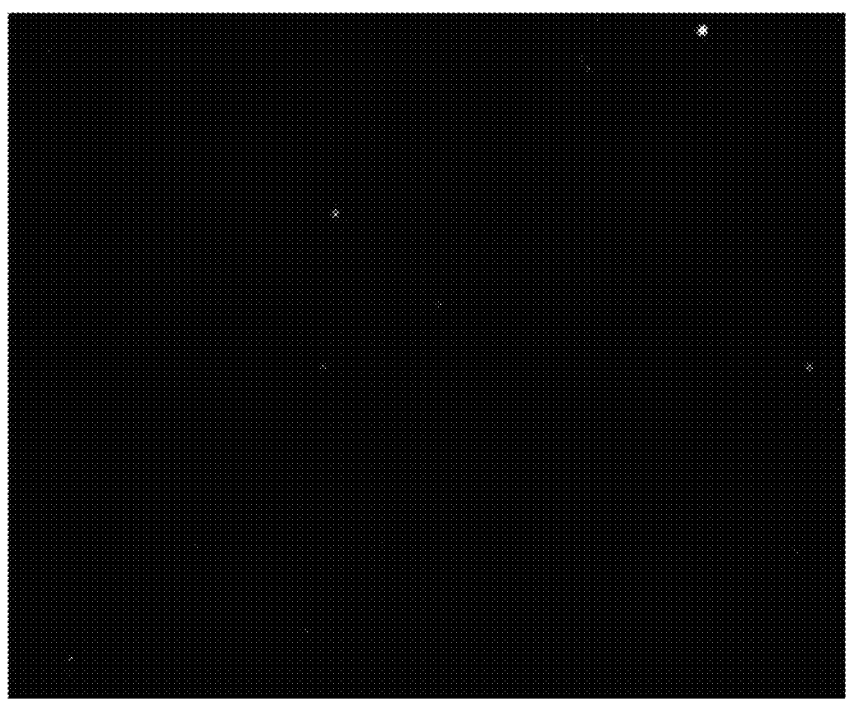
Figure 11C:
Figure 11C:
Figure 11D:
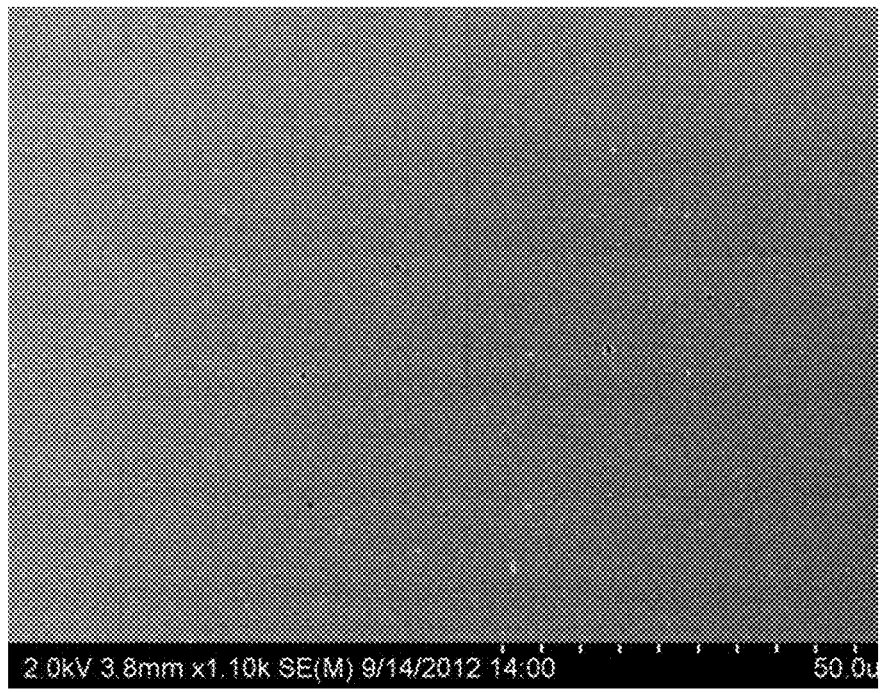
Figure 11D:
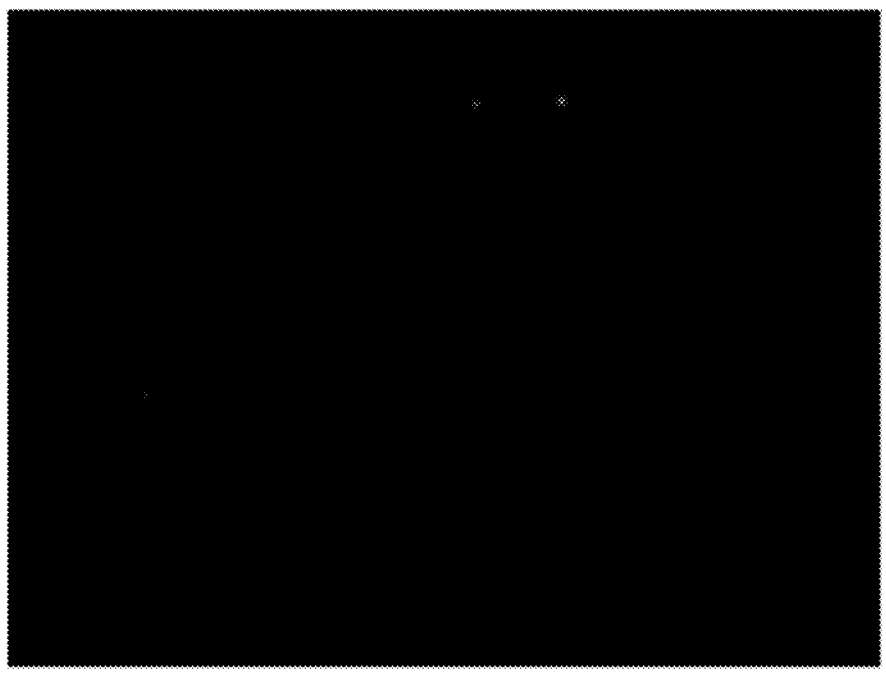
Figure 12A:
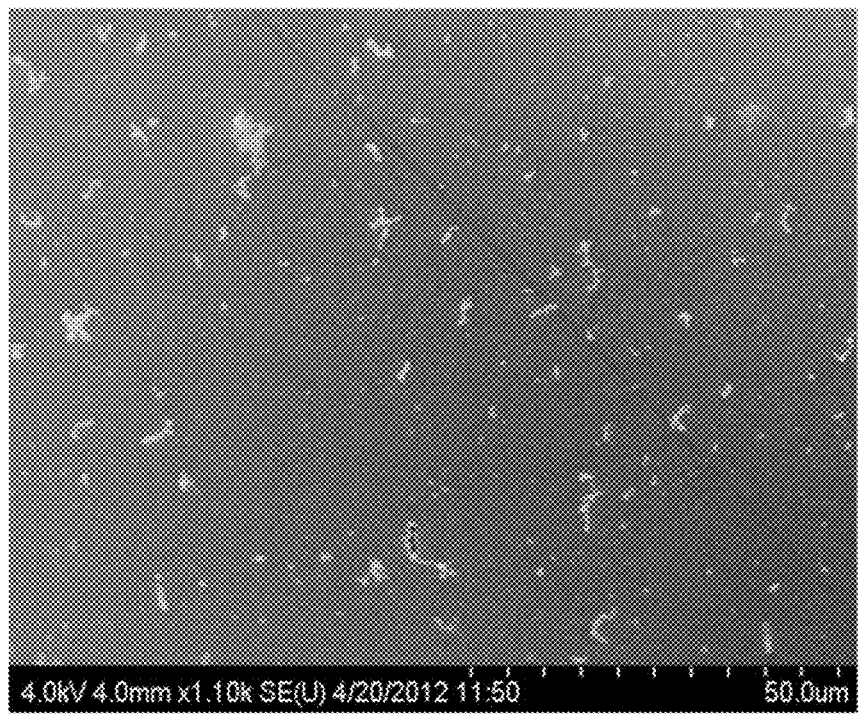
FIG. 12: Images of M. smegmatis, MAP and M. marinum cells captured by the recombinant Gp10 protein immobilized on gold surfaces (both SEM and FM images are shown for the same experiment). A) gold surface treated with 20 µg/ml of recombinant protein Gp10 and incubated with M. smegmatis cells; B) same as A but MAP cells were used; C) same as A but with M. marinum cells; D) the surface was treated in a same way as in A except that it was not exposed to the recombinant protein prior to incubation with M. smegmatis cells
Figure 12A:
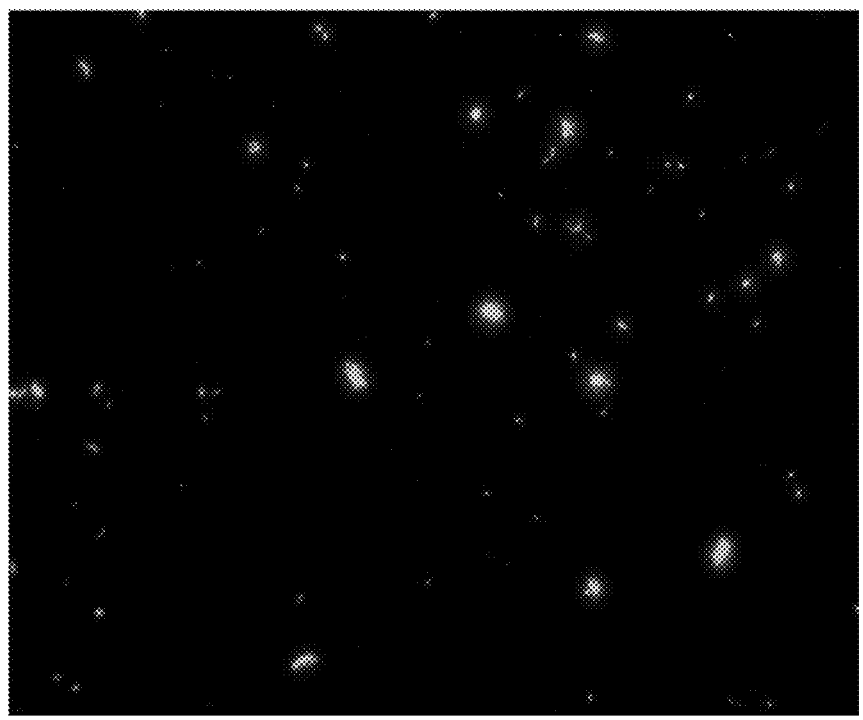
Figure 12B:
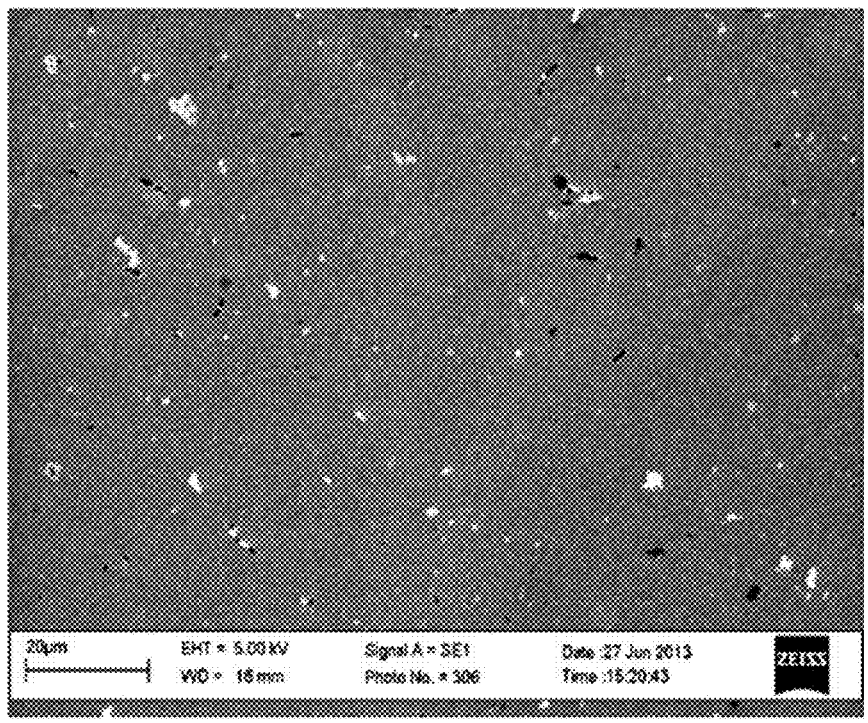
Figure 12B:
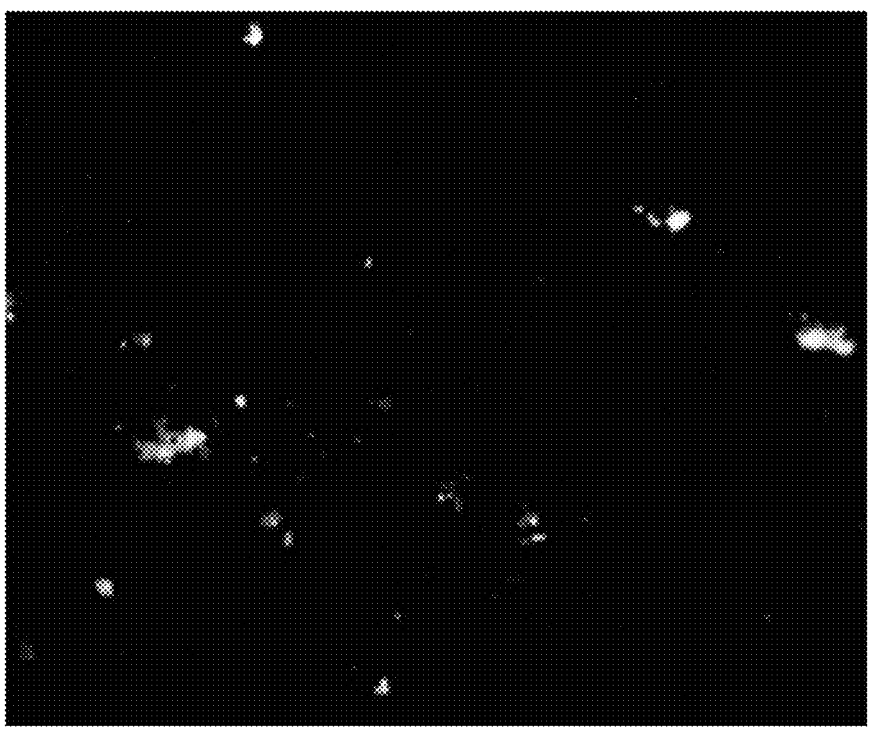
Figure 12C:
Figure 12C:
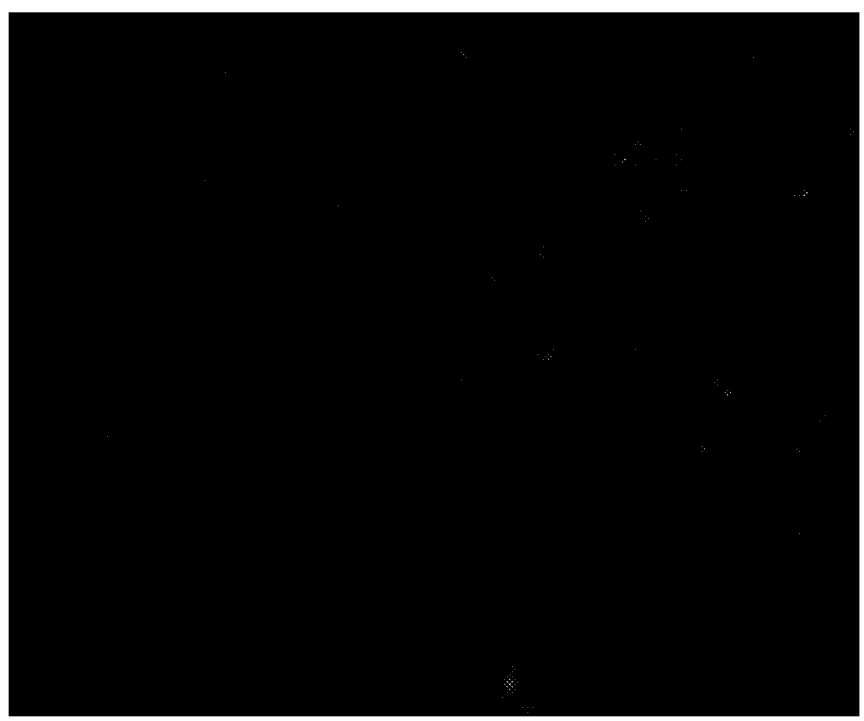
Figure 12D:
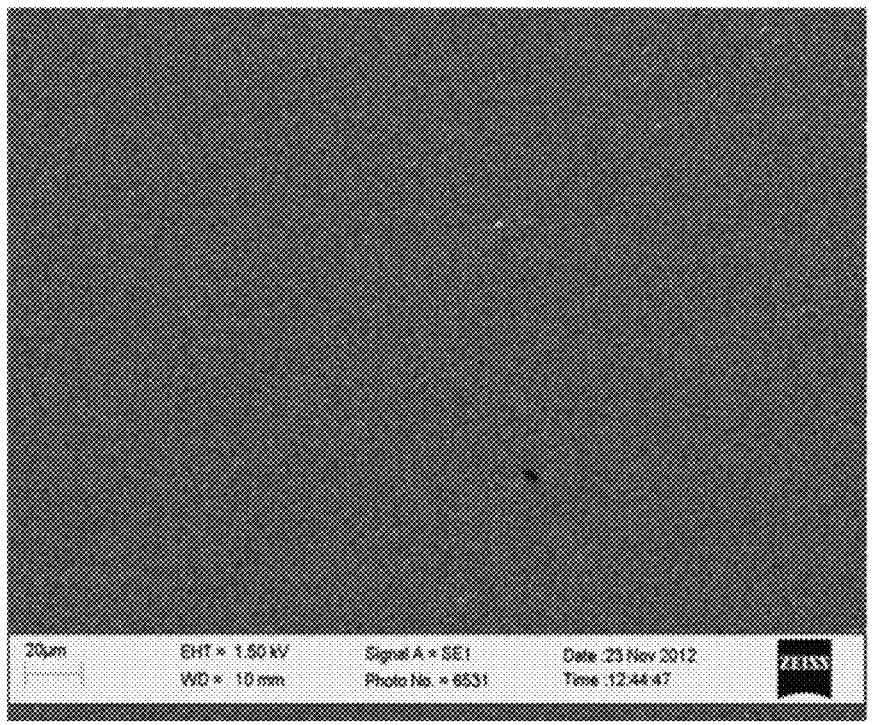
Figure 12D:

*E. coli* cells producing either Gp6 or Gp10 demonstrated similar growth characteristics and no inhibition of growth was revealed after induction of gene 6 or gene 10 expression. Recombinant Gp6 and Gp10 proteins, however, differed greatly in their solubility. While production of Gp6 led to high amounts of pure soluble protein, the yield of Gp10 was markedly lower (FIG. 10 A). Both proteins did not form SDS-resistant oligomers, which were shown to be characteristic of various phage RBPs including ones from *campylobacter* and *salmonella* phages. SDS PAGE analysis of the soluble Gp10 revealed a contaminant band at 60 kDa, i.e. about 20 kDa higher than the 40 kDa band corresponding to the $His_6$-Gp10 polypeptide ("$His_6$" disclosed as SEQ ID NO: 17) that has the predicted molecular weight of 38.1 kDa (FIG. 10 A). A similar band was absent in the preparation of Gp6, which contained, almost exclusively, a 40 kDa protein in agreement with the predicted mass of 39.7 kDa for $His_6$-Gp6 ("$His_6$" disclosed as SEQ ID NO: 17). We did not investigate further the identity of the 60 kDa band, which could represent a subunit of the chaperonin GroEL that is often observed in a complex with recombinant proteins. Recombinant Gp10 was mostly confined to the insoluble pellet as revealed by SDS-PAGE analysis of the urea extract of the insoluble fraction obtained after disruption of the protein producing cells (FIG. 10 B).

Assessment of Immobilized Gp6 and Gp10 as Probes for MAP and *M. smegmatis*.

To assess mycobacteriophage proteins as probes for mycobacteria, Gp6 and Gp10 were immobilized onto activated gold surfaces and these surfaces were used to assess the specificity of bacterial capture. Proteins obtained from the soluble fraction of the cell extract were used in the immobilization experiments. Bacterial capture was monitored by fluorescence microscopy and SEM. A negative control was run in parallel where a similar gold surface was treated with all reagents, but they were not exposed to the recombinant phage proteins. No significant bacterial capture was observed in the absence of phage RBPs.

Figure 3:
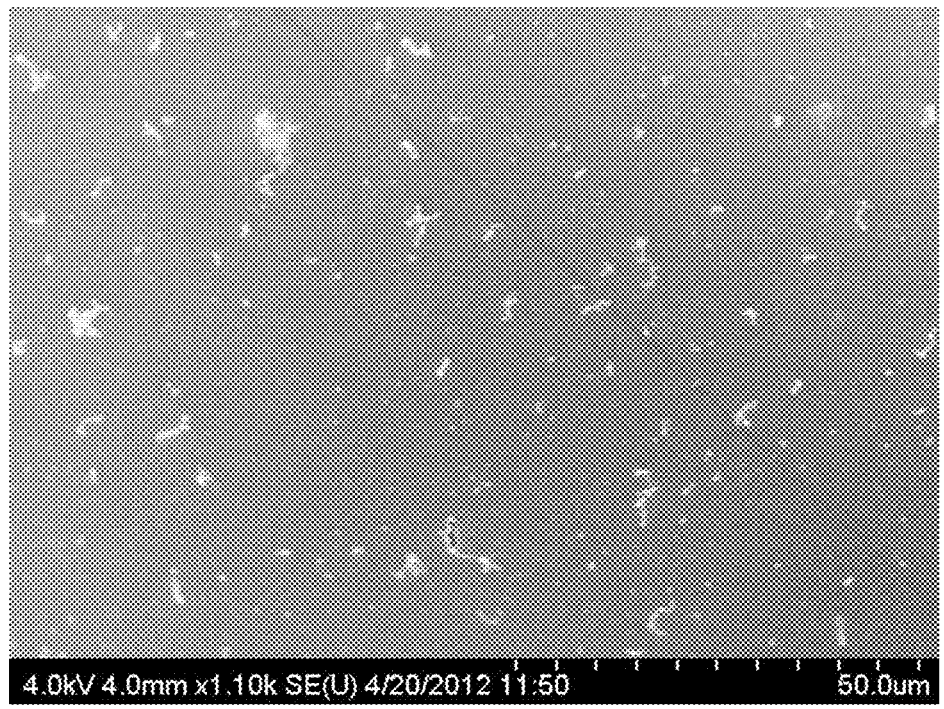
FIG. 3: SEM images of *M. smegmatis* capture by Gp-10 on the gold surface and the corresponding fluorescence microscopy images (labeled i and ii, respectively) A) i,ii—Gold Surface was modified with cysteamine hydrochloride, activated with 2% gluteraldehyde and incubated with 20 g/ml of recombinant protein Gp-10 followed by wash with buffer B) i,ii—The surface was treated in a same way as indicated above except that it was not exposed to the recombinant protein.
Figure 3:
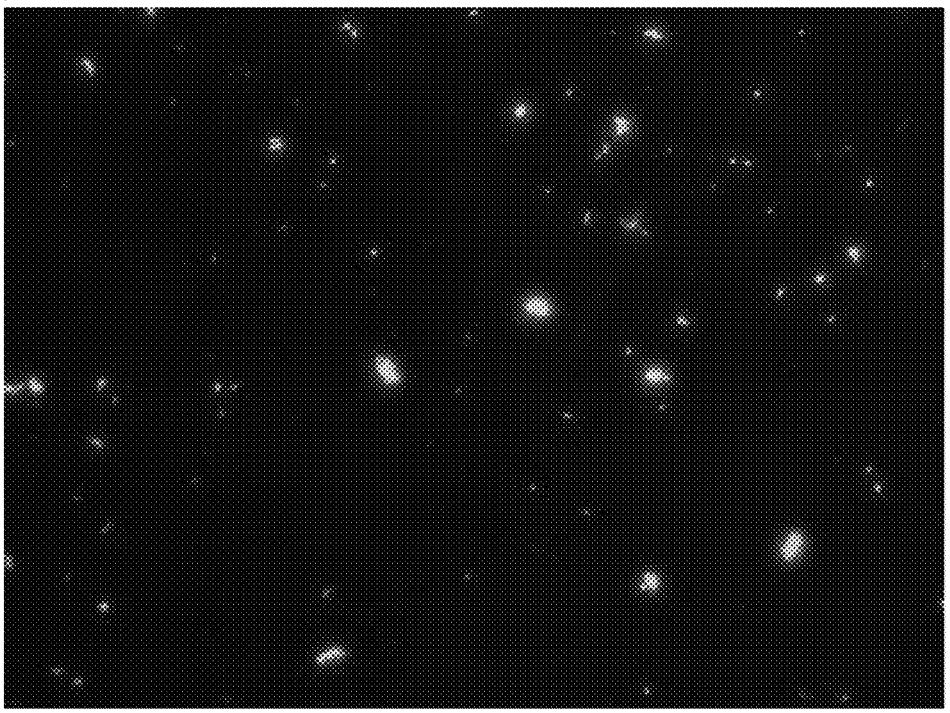
Figure 3:
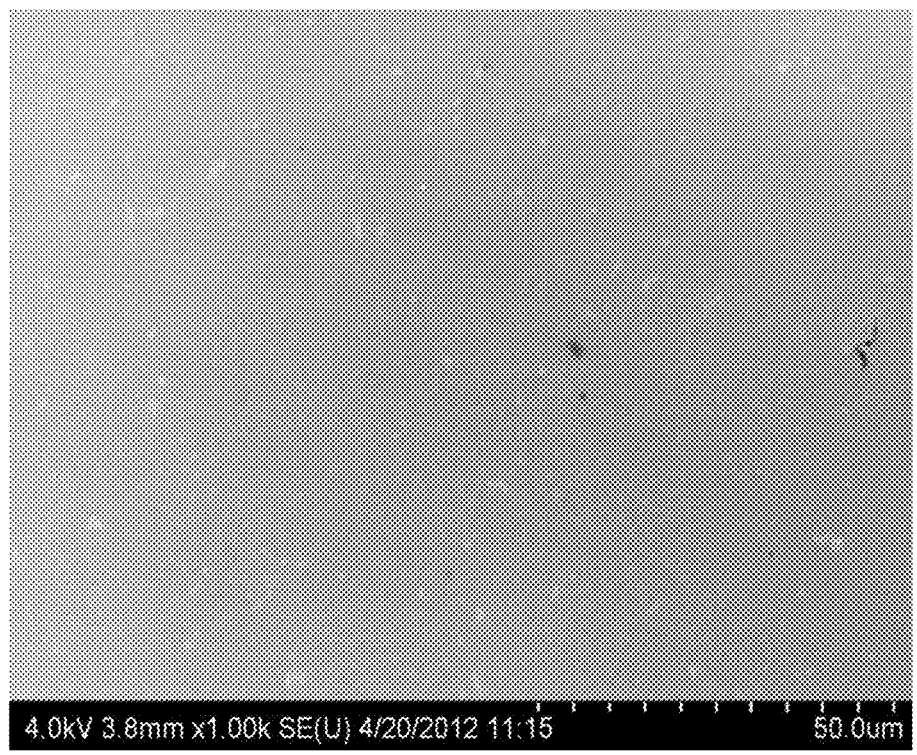
Figure 3:

Capture efficiency of *M. smegmatis* cells was $31.3 \pm 1.5 \times 10^{-3}$ cells/µm² and $28.7 \pm 1.18 \times 10^{-3}$ cells/µm² by Gp6 and Gp10, respectively when a 20 µg/ml solution of either protein was used for immobilization onto the gold chip (FIGS. 11 and 12). Gold chips covered with Gp10 demonstrated a capture efficiency of $12.3 \pm 1.3 \times 10^{-3}$ MAP cells/m² under similar conditions (FIG. 3). Remarkably, the immobilization procedure with either 20 or 40 µg/ml of Gp 6 did not capture any MAP cells (FIG. 11). Neither Gp6 nor Gp10 was able to serve as a capturing agent for *M. marinum* cells (FIGS. 11 and 12). The specificity of recognition was confirmed by exposing Gp6 or Gp10 covered surfaces to *E. coli* K12, *S. Typhimurium* and *C. jejuni* cells (not shown). These negative control experiments showed no bacterial capture. It can be concluded that Gp10 can specifically bind both *M. smegmatis* and MAP cells whereas Gp6 bind only *M. smegmatis* cells under the conditions used. Thus, Gp6 may be applied for the specific detection of *M. smegmatis* whereas Gp10 appears to be a promising candidate for the development of a capturing element for a high throughput MAP diagnostic platform.

Our results with Gp10 are unexpected and contradictory to the recent survey of mycobacterial endolysins where the expression of the L5 gene 10 in *M. smegmatis* caused a dramatic rise in ATP-release three hours after induction and cell lysis appeared to be complete seven hours after the induction of expression. Also, no overproduction of Gp10 could be detected in either soluble or insoluble fractions of *M. smegmatis* cells. We were able to successfully produce a small amount of soluble Gp10 using the conventional *E. coli* expression strain BL21(DE3) and observed most of the recombinant protein in the insoluble fraction in agreement with what was observed for other mycobacterial lysins. Successful heterologous expression of gene 10 in *E. coli* may be easily explained by the lack of toxic effects of Gp10 on the phylogenetically non-related bacterium as well as by the fact that the overproduction was performed at room temperature, not at 37° C. as described in the previous study.

The ability of L5 lysin Gp10 to bind effectively both *M. smegmatis* and MAP cells could be explained. First, the enzymatic activity of Gp10 could be impaired under the conditions used in the cell binding assays. For example, it was shown that the catalytic activities of *M. tuberculosis* peptidoglycan hydrolases RipA and RipB are optimal at acidic pH whereas tight binding to the peptidoglycan is still observed at pH 7 where the hydrolysis is quite slow. Another possible reason of the impaired lysin activity of Gp10 may be the presence of the non-conserved T321 substitution revealed in the cloned gene 10 that was used in a current study. This substitution is located fairly close to the putative catalytic Cys41 of the N-terminal NlpC/p60-like peptidase domain of Gp10. Second, proper orientation of the immobilized RBPs was demonstrated to be an important factor influencing the efficiency of cell capture. The "random", un-oriented immobilization via primary amino groups may leave the N-terminal catalytic domain inaccessible in many Gp10 molecules where only the cell binding C-terminal region would be exposed. This may essentially lead to the situation similar to that described previously where catalytically inactive cell binding domains of listeriaphages were used for the detection of *Listeria* cells. Finally, the lytic effect of exogenous Gp10 will probably be limited because peptidoglycan is often effectively masked by the other components of the thick cell wall except the polar and division septum regions as was shown for the listeriaphage endolysins. In addition, our binding experiment uses shorter exposures of cell suspensions to the immobilized Gp10 (1 hour at room temperature) compared to several hours of endogenous production at 37° C. described earlier. In any case, our study demonstrated the successful application of phage lysins for the rapid detection of mycobacteria.

Tosyl-activated magnetic Dynabeads® M-280 were functionalized with Gp10 to facilitate MAP capture for pre-concentration using an external magnetic field. The Gp10 functionalized beads were blocked with BSA to avoid any unspecific interactions. *Salmonella* cells were used in a control experiment to demonstrate the specificity of capture by the beads. MAP and *salmonella* cells were stained with a fluorescent dye prior to mixing with the beads. After incubation with bacteria, the beads were concentrated using a magnet and the bead surface was analyzed using fluorescence microscopy. The micrograph shows that the MAP cells were captured successfully on the beads surface (FIG. 6). The same result was obtained when the bacteria were pre-concentrated using Gp10 covered beads from 3% fat milk spiked with MAP cells (results not shown). The magnetic beads were moderately auto-fluorescent and were easily detected in the field of view as was previously described. One can see the bright and "clustered" fluorescence areas on the bead surface representing the bound MAP cells. In addition to that, a strong aggregation of the beads was noted after exposure to the MAP cells but not in the control experiment. This effect was similar to what we observed when *C. jejuni* cells were pre-concentrated using beads covered with *C. jejuni* phage RBP and we believe occurs due to several bacterial cells binding simultaneously to more than one bead. Thus, a mycobacteriophage cell binding protein can be successfully exploited to capture MAP cells onto magnetic beads that can be subsequently concentrated using a simple magnet. This allows a rapid and effective pre-concentration of MAP cells from different liquid natural matrices (e.g. milk) and may augment the existing detection platforms as was shown for *C. jejuni* phage RBP.

Identification of Possible Gp6 Carbohydrate Ligands.

ESI mass spectrometry analysis suggests that recombinant $His_6$-Gp6 ("$His_6$" disclosed as SEQ ID NO: 17) exists as a monomer of 39760±10 Da which is close to the predicted mass of 39 729 Da. The bioinformatic analysis did not reveal any conserved domains that could be assigned to Gp6 so the protein was tested for its ability to bind mycobacterial complex carbohydrates using ESI-MS and a set of chemically synthesized fragments of known mycobacterial surface glycans. ESI-MS demonstrated that Gp6 has a modest affinity towards chemically synthesized mycobacterial arabinan fragments (Table 5). Oligosaccharide/Gp6 interaction was sensitive to minor changes in the oligosaccharide structure similarly to the interaction of monoclonal antibody CS-35 with the oligosaccharide fragments of mycobacterial arabinan where Ka values were ranging from $10^2$ to $10^5$ $M^{-1}$.

The presence of α-(1→3) glycosidic bonds between the second and the third arabinose residues enables the binding of tetrasaccharide 7 in contrast to isomeric tetrasaccharide 4 where only β-(1→2) and α-(1→5) bonds are present. The addition of the mannose residue to tetrasaccharide 4 (compound 1), removing the terminal β-arabinose residue (compound 5) or changing the terminal arabinose residue to an α-configuration (compound 8) also promotes binding to Gp6. It should be mentioned that the presence of additional mannose residues (compounds 2 and 9) or the branching structure (compounds 3 and 6) did not increase the Gp6 affinity for the oligosaccharides. Recombinant Gp6 was also able to bind a number of oligosaccharide fragments of phenolic glycolipids (Table 5, compounds 10-15). Again, a small difference in structure, like an absence of a methyl group, may totally abolish the binding (Table 5, compounds 13 and 14).

The affinity of Gp6 towards the oligosaccharide fragments that showed binding was several orders of magnitude lower than the affinity of the *salmonella* phage P22 tailspike protein or the receptor binding protein from the lactococcal phage towards their cognate receptor oligosaccharides. Thus, it seems unlikely that the oligosaccharides tested in the current study represent the actual phage receptor molecules. Indeed, phenolic glycolipids were not found in *M. smegmatis* cells that can bind Gp6. These molecules are rather produced by *M. marinum* cells that could not be captured by the immobilized Gp6. Further studies are needed to find the native oligosaccharide ligand of Gp6. Notably, it was shown that the oligomannose-capped arabinan is present only in slow growing mycobacteria such as *M. avium, M. marinum, M. tuberculosis* or *M. leprae* whereas phosphoinositol-capped arabinan was found in fast-growing *M. smegmatis*. The ability of the immobilized recombinant Gp6 to bind *M. smegmatis* but not MAP or *M. marinum* cells may possibly be explained by the differences in cap structure of the lipoarabinomannan component of the cell wall assuming that Gp6 is indeed recognizing this molecule in vivo.

Taking into account the ease of the one-step affinity purification, the high yield of soluble recombinant Gp6 and its cell and carbohydrate binding properties, one can suggest this protein as a template for the development of the artificial lectins via directed evolution methods.

Figure 13:
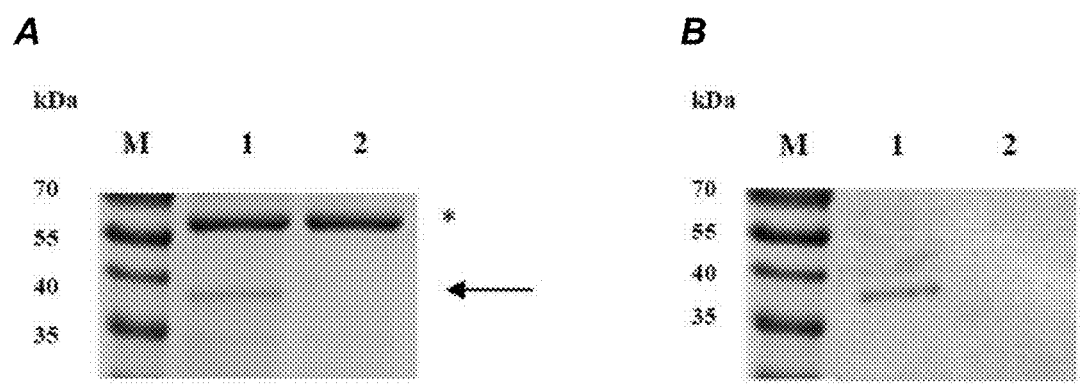
FIG. 13: Peptidoglycan binding assay of recombinant Gp10. A) M, molecular weight markers; lane 1—the gel image obtained after SDS-PAGE followed by Coomassie R-250 staining of Gp10 purified from the soluble fraction of the expression strain. The arrow indicates the expected position of the recombinant Gp10 and the asterisk labels the ca. 60 kDa contaminant; lane 2, same as lane 1, but the Gp10 sample was pre-incubated with the peptidoglycan; B) same experiment was performed as in A but the Gp10 protein sample was obtained by refolding following after 8 M urea extraction of the insoluble cell pellet of the expression strain.

The general peptidoglycan binding properties of recombinant Gp10 were tested using the commercially available peptidoglycan from *B. subtilis* that was shown earlier to bind mycobacterial peptidoglycan hydrolases. It was possible to selectively remove recombinant Gp10 from the solution after incubating with a suspension of peptidoglycan obtained from *B. subtilis* cell walls (FIG. 13 A). Notably, the "60 kDa" contaminant did not show any peptidoglycan binding properties. The refolded sample of Gp10 contained only a single polypeptide species and retained the ability to bind peptidoglycan (FIG. 13 B) indicating that the native protein can be obtained at higher levels of purity using the urea extraction/refolding procedures. These findings pave the way for the future structural and functional studies of this phage lysine that are obviously needed to determine the whole cell and peptidoglycan binding and catalytic specificity of this protein in more detail.

It should be noted that Gp10 obtained from the soluble fraction of the cell extract contained a significant amount of contaminant (FIG. 10 A). Therefore, the actual concentration of Gp10 can be estimated to be several times lower than the values obtained on the basis of the absorbance of the samples at 280 nm and indicated above. Thus, Gp10 can be viewed as a very potent reagent for the development of the novel detection platforms where the minimal amount of the sensing element can be used making the whole system less costly to produce. Indeed, the emerging phage lysin-based technologies look very promising for the detection of staphylococci and *listeria*. This study adds mycobacteria to the list.

Applicants' approach can potentially be applied for the development of a rapid diagnostic tool for the other *M. avium* subspecies where Gp10-based biosensors could possibly be used. It is well known that *M. avium* also causes serious infections in humans that may lead to extensive lung damage Immunocompromised individuals and cystic fibrosis patients are particularly susceptible to such infections that can also be disseminated and damage a number of tissues.

Summary

Slow growing *Mycobacterium avium* subsp. *paratuberculosis* (MAP) causes a deadly condition in cattle known as Johne's disease where asymptomatic carriers are the major source of disease transmission. *M. smegmatis* is a model mycobacterium that can also cause opportunistic infections in a number of human tissues and, rarely, a respiratory disease. Currently, there are no rapid, culture-independent, reliable and inexpensive tests for the diagnostics of MAP or *M. smegmatis* infections.

The effectiveness of techniques based on enzyme-linked immunosorbent assays (ELISA) and polymerase chain reactions (PCR) is limited. ELISA is hindered by antibody degradation whereas PCR is inhibited by many natural agents, e.g. fatty acids and calcium ions. Bacteriophages are viruses producing a number of proteins that effectively and specifically recognize the cell envelopes of their bacterial hosts.

Applicants have demonstrated that the mycobacterial phage L5 minor tail protein Gp6 and lysin Gp10 are useful tools for the rapid detection of mycobacteria Immobilized Gp10 was able to bind both MAP and *M. smegmatis* cells whereas Gp6 was *M. smegmatis* specific. Neither of the two proteins was able to capture *M. marinum* cells. Electrospray ionization mass spectrometry revealed that recombinant Gp6 binds a number of chemically synthesized fragments of mycobacterial surface glycans and that oligosaccharide/Gp6 interaction was sensitive to minor changes in the oligosaccharide structure. Magnetic beads coated with recombinant lysin Gp10 were used to specifically pre-concentrate MAP cells. Applicants' findings demonstrate the successful use of mycobacteriophage proteins as a pathogen capturing platform that can potentially improve the effectiveness of existing diagnostic methods.

TABLE 5

Association constants ($K_a$) for Gp6 and mycobacterial surface oligosaccharides measured at 25° C. and pH 7.2 using the direct ESI-MS assay [1,2].

| # | Bacterial oligosaccharide structures | MW, Da | Ka, $M^{-1} \times 10^3$ |
|---|---|---|---|
| 1 | α-Manp-(1→5)-β-Araf-(1→2)-α-Araf-(1→5)-α-Araf-(1→5)-α-Araf-octyl-NHCOCF$_3$ | 931 | 3.9 ± 1.1 |
| 2 | α-Manp-(1→2)-α-Manp-(1→5)-β-Araf-(1→2)-α-Araf-(1→5)-α-Araf-(1→5)-α-Araf-octyl-NHCOCF$_3$ | 1094 | 4.4 ± 3.9 |
| 3 | β-Araf-(1→2)-α-Araf-(1→5)[β-Araf-(1→2)-α-Araf-(1→3)]-α-Araf-(1→5)-α-Araf-octyl-NHCOCF$_3$ | 1034 | 3.6 ± 0.4 |
| 4 | β-Araf-(1→2)-α-Araf-(1→5)-α-Araf-(1→5)-α-Araf-octyl-NHCOCF$_3$ | 770 | NB[3] |
| 5 | α-Araf-(1→5)-α-Araf-(1→5)-α-Araf-octyl-NHCOCF$_3$ | 638 | 7.6 ± 3.2 |
| 6 | α-Araf-(1→5)-[α-Araf-(1→3)]-α-Araf-(1→5)-α-Araf-octyl-NHCOCF$_3$ | 770 | 2.4 ± 0.7 |
| 7 | β-Araf-(1→2)-α-Araf-(1→3)-α-Araf-(1→5)-α-Araf-octyl-NHCOCF$_3$ | 770 | 1.1 ± 0.2 |
| 8 | α-Araf-(1→5)-α-Araf-(1→5)-α-Araf-(1→5)-a-Araf-octyl-NHCOCF$_3$ | 669 | 6.9 ± 0.8 |
| 9 | α-Manp-(1→2)-α-Manp-(1→2)-α-Manp-(1→5)-β-Araf-(1→2)-α-Araf-(1→5)-α-Araf-(1→5)-α-Araf-octyl-NHCOCF$_3$ | 1256 | 2.6 ± 1.1 |
| 10 | 2,3,4-tri-O-CH$_3$-α-Fucp-(1→3)-α-Rhap(1→3)-2-O-CH$_3$-α-RhapOPMP | 619 | 1.0 ± 0.5 |
| 11 | 2,4-di-O-CH$_3$-α-Fucp-(1→3)-α-Rhap(1→3)-α-Rhap-OPMP | 605 | 3.0 ± 1.8 |
| 12 | 2,3,4-tri-O-CH$_3$-α-Fucp-(1→3)-α-Rhap(1→3)-α-RhapOpPMP | 605 | 3.5 ± 1.7 |

TABLE 5-continued

Association constants ($K_a$) for Gp6 and mycobacterial surface oligosaccharides measured at 25° C. and pH 7.2 using the direct ESI-MS assay [1,2].

| # | Bacterial oligosaccharide structures | MW, Da | Ka, $M^{-1} \times 10^3$ |
|---|---|---|---|
| 13 | 3,6-di-O-CH$_3$-β-Glcp-(1→4)-2,3-di-O-CH$_3$-α-Rhap-(1→2)-3-O-CH$_3$-α-RhapOPMP | 649 | 2.4 ± 1.3 |
| 14 | 6-O-CH$_3$-β-Glcp-(1→4)-2,3-di-O-CH$_3$-α-Rhap-(1→2)-3-O-CH$_3$-α-RhapOPMP | 621 | NB[3] |
| 15 | α-Rhap-(1→3)-2-O-CH$_3$-α-RhapOPMP | 431 | NB[3] |

[1]Fucose (Fuc) and rhamnose (Rha) residues are of the L-configuration; mannose (Man), arabinose (Ara) and glucose (Glc) residues are of the D-configuration.
[2]PMP-p-methoxyphenyl.
[3]NB-no binding detected.

REFERENCES

1. Sweeney R W. 2011. Pathogenesis of *paratuberculosis*. Vet. Clin. North Loftus m. Food Anim Pract. 27:537-546.
2. Lombard J E. 2011. Epidemiology and economics of *paratuberculosis*. Vet. Clin. North Am. Food Anim Pract. 27:525-535.
3. Chiodini R J, Chamberlin W M, Sarosiek J, McCallum R W. 2012. Crohn's disease and the mycobacterioses: a quarter century later. Causation or simple association? Crit. Rev. Microbiol. 38:52-93.
4. Brown-Elliott B A, Wallace R J, Jr. 2002. Clinical and taxonomic status of pathogenic nonpigmented or late-pigmenting rapidly growing mycobacteria. Clin. Microbiol. Rev. 15:716-746.
5. Singh A, Poshtiban S, Evoy S. 2013. Recent advances in bacteriophage based biosensors for food-borne pathogen detection. Sensors (Basel) 13:1763-1786.
6. Tawil N, Sacher E, Mandeville R, Meunier M. 2014. Bacteriophages: biosensing tools for multi-drug resistant pathogens. Analyst 139:1224-1236.
7. Casjens S R, Molineux I J. 2012. Short noncontractile tail machines: adsorption and DNA delivery by podoviruses. Adv. Exp. Med. Biol. 726:143-179.
8. Davidson A R, Cardarelli L, Pell L G, Radford D R, Maxwell K L. 2012. Long noncontractile tail machines of bacteriophages. Adv. Exp. Med. Biol. 726:115-142.
9. Leiman P G, Shneider M M. 2012. Contractile tail machines of bacteriophages. Adv. Exp. Med. Biol. 726: 93-114.
10. Garcia-Doval C, van Raaij M J. 2013. Bacteriophage receptor recognition and nucleic acid transfer. Subcell. Biochem. 68:489-518.
11. Singh A, Arutyunov D, Szymanski C M, Evoy S. 2012. Bacteriophage based probes for pathogen detection. Analyst 137:3405-3421.
12. Singh A, Arya S K, Glass N, Hanifi-Moghaddam P, Naidoo R, Szymanski C M, Tanha J, Evoy S. 2010. Bacteriophage tailspike proteins as molecular probes for sensitive and selective bacterial detection. Biosens. Bioelectron. 26:131-138.
13. Singh A, Arutyunov D, McDermott M T, Szymanski C M, Evoy S. 2011. Specific detection of *Campylobacter jejuni* using the bacteriophage NCTC 12673 receptor binding protein as a probe. Analyst 136:4780-4786.
14. Javed M A, Poshtiban S, Arutyunov D, Evoy S, Szymanski C M. 2013. Bacteriophage receptor binding protein based assays for the simultaneous detection of *Campylobacter jejuni* and *Campylobacter coli*. PLoS One 8:e69770.
15. Poshtiban S, Javed M A, Arutyunov D, Singh A, Banting G, Szymanski C M, Evoy S. 2013. Phage receptor binding protein-based magnetic enrichment method as an aid for real time PCR detection of foodborne bacteria. Analyst 138:5619-5626.
16. Catalao M J, Gil F, Moniz-Pereira J, Sao-Jose C, Pimentel M. 2013. Diversity in bacterial lysis systems: bacteriophages show the way. FEMS Microbiol. Rev. 37:554-571.
17. Fischetti V A. 2011. Exploiting what phage have evolved to control gram-positive pathogens. Bacteriophage 1:188-194.
18. Drulis-Kawa Z, Majkowska-Skrobek G, Maciejewska B, Delattre A S, Lavigne R. 2012. Learning from bacteriophages—advantages and limitations of phage and phage-encoded protein applications. Curr. Protein Pept. Sci. 13:699-722.
19. Pastagia M, Schuch R, Fischetti V A, Huang D B. 2013. Lysins: the arrival of pathogen-directed anti-infectives. J. Med. Microbiol. 62:1506-1516.
20. Kretzer J W, Lehmann R, Schmelcher M, Banz M, Kim K P, Korn C, Loessner M J. 2007. Use of high-affinity cell wall-binding domains of bacteriophage endolysins for immobilization and separation of bacterial cells. Appl. Environ. Microbiol. 73:1992-2000.
21. Schmelcher M, Shabarova T, Eugster M R, Eichenseher F, Tchang V S, Banz M, Loessner M J. 2010. Rapid multiplex detection and differentiation of *Listeria* cells by use of fluorescent phage endolysin cell wall binding domains. Appl. Environ. Microbiol. 76:5745-5756.
22. Hatfull G F, Sarkis G J. 1993. DNA sequence, structure and gene expression of mycobacteriophage L5: a phage system for mycobacterial genetics. Mol. Microbiol. 7:395-405.
23. Sarkis G J, Jacobs W R, Jr., Hatfull G F. 1995. L5 luciferase reporter mycobacteriophages: a sensitive tool for the detection and assay of live mycobacteria. Mol. Microbiol. 15:1055-1067.
24. Fullner K J, Hatfull G F. 1997. Mycobacteriophage L5 infection of *Mycobacterium bovis* BCG: implications for phage genetics in the slow-growing mycobacteria. Mol. Microbiol. 26:755-766.
25. Altschul S F, Gish W, Miller W, Myers E W, Lipman D J. 1990. Basic local alignment search tool. J. Mol. Biol. 215:403-410.
26. Altschul S F, Madden T L, Schaffer A A, Zhang J, Zhang Z, Miller W, Lipman D J. 1997. Gapped BLAST and PSI-BLAST: a new generation of protein database search programs. Nucleic Acids Res. 25:3389-3402.

27. Kelley L A, Sternberg M I 2009. Protein structure prediction on the Web: a case study using the Phyre server. Nat. Protoc. 4:363-371.
28. Singh A, Glass N, Tolba M, Brovko L, Griffiths M, Evoy S. 2009 Immobilization of bacteriophages on gold surfaces for the specific capture of pathogens. Biosens. Bioelectron. 24:3645-3651.
29. Rademacher C, Shoemaker G K, Kim H S, Zheng R B, Taha H, Liu C, Nacario R C, Schriemer D C, Klassen J S, Peters T, Lowary T L. 2007. Ligand specificity of CS-35, a monoclonal antibody that recognizes mycobacterial lipoarabinomannan: a model system for oligofuranoside-protein recognition. J. Am. Chem. Soc. 129:10489-10502.
30. Elsaidi H R, Barreda D R, Cairo C W, Lowary T L. 2013. Mycobacterial phenolic glycolipids with a simplified lipid aglycone modulate cytokine levels through Toll-like receptor 2. Chembiochem. 14:2153-2159.
31. Sun J, Kitova E N, Wang W, Klassen J S. 2006. Method for distinguishing specific from nonspecific protein-ligand complexes in nanoelectrospray ionization mass spectrometry. Anal. Chem. 78:3010-3018.
32. Wang W, Kitova E N, Klassen J S. 2003. Influence of solution and gas phase processes on protein-carbohydrate binding affinities determined by nanoelectrospray Fourier transform ion cyclotron resonance mass spectrometry. Anal. Chem. 75:4945-4955.
33. El-Hawiet A, Kitova E N, Klassen J S. 2012. Quantifying carbohydrate-protein interactions by electrospray ionization mass spectrometry analysis. Biochemistry 51:4244-4253.
34. El-Hawiet A, Kitova E N, Arutyunov D, Simpson D J, Szymanski C M, Klassen J S.
2012. Quantifying ligand binding to large protein complexes using electrospray ionization mass spectrometry. Anal. Chem. 84:3867-3870.
35. Barsom E K, Hatfull G F. 1996. Characterization of *Mycobacterium smegmatis* gene that confers resistance to phages L5 and D29 when overexpressed. Mol. Microbiol. 21:159-170.
36. Mediavilla J, Jain S, Kriakov J, Ford M E, Duda R L, Jacobs W R, Jr., Hendrix R W, Hatfull G F. 2000. Genome organization and characterization of mycobacteriophage Bxb1. Mol. Microbiol. 38:955-970.
37. Besra G S, Khoo K H, Belisle J T, McNeil M R, Morris H R, Dell A, Brennan P J. 1994. New pyruvylated, glycosylated acyltrehaloses from *Mycobacterium smegmatis* strains, and their implications for phage resistance in mycobacteria. Carbohydr. Res. 251:99-114.
38. Khoo K H, Suzuki R, Dell A, Morris H R, McNeil M R, Brennan P J, Besra G S. 1996. Chemistry of the lyxose-containing mycobacteriophage receptors of *Mycobacterium phlei/Mycobacterium smegmatis*. Biochemistry 35:11812-11819.
39. Payne K M, Hatfull G F. 2012. Mycobacteriophage endolysins: diverse and modular enzymes with multiple catalytic activities. PLoS One 7:e34052.
40. Kropinski A M, Arutyunov D, Foss M, Cunningham A, Ding W, Singh A, Pavlov A R, Henry M, Evoy S, Kelly J, Szymanski C M. 2011. Genome and proteome of *Campylobacter jejuni* bacteriophage NCTC 12673. Appl. Environ. Microbiol. 77:8265-8271.
41. Rohman M, Harrison-Lavoie K J. 2000. Separation of copurifying GroEL from glutathione-S-transferase fusion proteins. Protein Expr. Purif. 20:45-47.
42. Both D, Schneider G, Schnell R. 2011. Peptidoglycan remodeling in *Mycobacterium tuberculosis*: comparison of structures and catalytic activities of RipA and RipB. J. Mol. Biol. 413:247-260.
43. Eugster M R, Loessner M J. 2012. Wall teichoic acids restrict access of bacteriophage endolysin Ply118, Ply511, and PlyP40 cell wall binding domains to the *Listeria monocytogenes* peptidoglycan. J. Bacteriol. 194:6498-6506.
44. Bebeacua C, Tremblay D, Farenc C, Chapot-Chartier M P, Sadovskaya I, van Heel M, Veesler D, Moineau S, Cambillau C. 2013. Structure, adsorption to host, and infection mechanism of virulent lactococcal phage p2. J. Virol. 87:12302-12312.
45. Dobson G, Minnikin D E, Besra G S, Mallet A I, Magnusson M. 1990. Characterisation of phenolic glycolipids from *Mycobacterium marinum*. Biochim. Biophys. Acta 1042:176-181.
46. Yu J, Tran V, Li M, Huang X, Niu C, Wang D, Zhu J, Wang J, Gao Q, Liu J. 2012. Both phthiocerol dimycocerosates and phenolic glycolipids are required for virulence of *Mycobacterium marinum*. Infect. Immun. 80:1381-1389.
47. Nigou J, Gilleron M, Puzo G. 2003. Lipoarabinomannans: from structure to biosynthesis. Biochimie 85:153-166.
48. Pitarque S, Herrmann J L, Duteyrat J L, Jackson M, Stewart G R, Lecointe F, Payre B, Schwartz O, Young D B, Marchal G, Lagrange P H, Puzo G, Gicquel B, Nigou J, Neyrolles O. 2005. Deciphering the molecular bases of *Mycobacterium tuberculosis* binding to the lectin D C-SIGN reveals an underestimated complexity. Biochem. J. 392:615-624.
49. Mishra A K, Driessen N N, Appelmelk B J, Besra G S. 2011. Lipoarabinomannan and related glycoconjugates: structure, biogenesis and role in *Mycobacterium tuberculosis* physiology and host-pathogen interaction. FEMS Microbiol. Rev. 35:1126-1157.
50. Chibli H, Ghali H, Park S, Peter Y A, Nadeau J L. 2014 Immobilized phage proteins for specific detection of staphylococci. Analyst 139:179-186.
51. Schmelcher M, Loessner M J. 2014. Application of bacteriophages for detection of foodborne pathogens. Bacteriophage 4:e28137.
52. Weiss C H, Glassroth J. 2012. Pulmonary disease caused by nontuberculous mycobacteria. Expert. Rev. Respir. Med. 6:597-612; quiz 613.
53. Griffith D E. 2007. Therapy of nontuberculous mycobacterial disease. Curr. Opin. Infect. Dis. 20:198-203.
54. Griffith D E, Aksamit T, Brown-Elliott B A, Catanzaro A, Daley C, Gordin F, Holland S M, Horsburgh R, Huitt G, Iademarco M F, Iseman M, Olivier K, Ruoss S, von Reyn C F, Wallace R J, Jr., Winthrop K. 2007. An official ATS/IDSA statement: diagnosis, treatment, and prevention of nontuberculous mycobacterial diseases. Am. J. Respir. Crit. Care Med. 175:367-416.
55. S. Pedley, J. Bartram, G. Rees, A. Dufour and J. Cotruvo, World Health Organization. Pathogenic Mycobacteria in Water: A Guide to Public Health. 2004, Consequences, Monitoring and Management, ISBN: 1 84339 059 0.
56. Hermon-Taylor, J., T. J. Bull, J. M. Sheridan, J. Cheng, M. L. Stellakis, and N. Sumar Causation of Crohn's disease by *Mycobacterium avium* subspecies *paratuberculosis*. 2000, Can. J. Gastroenterol. 14:521-539.
57. http://www.johnesdisease.org/58.
58. Biljana Mihajlovic, Mark Klassen, Susan Springthorpe, Helene Couture and Jeff Farber Assessment of Sources of Exposure for *Mycobacterium avium* subsp. *paratuberculosis* in Food and Water. International Food Risk Analysis Journal 2011, Vol. 1, No. 2, 1-22
59. I. Slana, I P. Kralik, A. Kralova, V. Babak, and I. Pavlik Examination of milk filters by real-time PCR as a herd-level indicator of the presence of *Mycobacterium avium* subspecies *paratuberculosis* in dairy herds 2012 J. Dairy Sci. 95:1162-1165
60. V. Loftus, J. R., P. Schoenfeld, and W. J. Sandborn. The epidemiology and natural history of Crohn's disease in population-based patient cohorts from North America: a systematic review, Aliment Pharmacol Ther 2002; 16: 51-60.
61. Sreedhar Subramanian, Carol L. Roberts, C. Anthony Hart, Helen M. Martin, Steve W. Edwards, Jonathan M. Rhodes and Barry J. Campbell, Replication of Colonic Crohn's Disease Mucosal *Escherichia coli* Isolates within Macrophages and Their Susceptibility to Antibiotics. Antimicrobial Agents and Chemotherapy, February 2008, p. 427-434 Vol. 52, No. 2, 0066-4804/08/$08.00_0 doi: 10.1128/AAC.00375-07.
62. Chiedzo M. Mpofu, Barry J. Campbell, Sreedhar Subramanian, Stuart Marshall—Clarke, C. Anthony Hart, Andy Cross, Carol L. Roberts, Adrian Mcgoldrick, Steven W. Edwards and Jonathan M. Rhodes, Microbial Mannan Inhibits Bacterial Killing by Macrophages: A Possible-Pathogenic Mechanism for Crohn's Disease. Gastroenterology 2007; 133:1487-1498.
63. Emma C. Stanley, Richard J. Mole, Rebecca J. Smith, Sarah M. Glenn, Michael R. Barer, Michael McGowan, and Catherine E. D. Rees, Development of a New, Combined Rapid Method Using Phage and PCR for Detection and Identification of Viable *Mycobacterium paratuberculosis* Bacteria within 48 Hours. Applied and Environmental Microbiology, March 2007, p. 1851-1857 Vol. 73, No. 60099-2240/07/$08.00_0 doi:10.1128/AEM.01722-06.
64. Sunil K. Arya, Amit Singh, Ravendra Naidoo, Peng Wu, Mark T. McDermott and S. Evoy, Chemically immobilized T4-bacteriophage for specific *Escherichia coli* detection using surface plasmon resonance. Analyst, 2011, 136, 486-492
65. M. Tolba, O. Minikh, L. Y. Brovko, S. Evoy and M. W. Griffiths, Oriented Immobilization of Bacteriophages for Biosensor Applications. Applied and Environmental Microbiology, January 2010, p. 528-535 Vol. 76, No. 2, 0099-2240/10/$12.00 doi:10.1128/AEM.02294-09
66. Vijayarani Kumanan, Sam R. Nugen, Antje J. Baeumner, Yung-Fu Chang. A biosensor assay for the detection of *Mycobacterium avium* subsp. *paratuberculosis* in fecal samples. J. Vet. Sci. (2009), 10(1), 35-42DOI: 10.4142/jvs.2009.10.1.35
67. Ellingson, J. L., C. A. Bolin, and J. R. Stabel. Identification of a gene unique to *Mycobacterium avium* subspecies *paratuberculosis* and application to diagnosis of *paratuberculosis*. 1998 Mol. Cell. Probes 12:133-142.
68. Poupart, P., M. Coene, H. Van Heuverswyn, and C. Cocito. Preparation of a specific RNA probe for detection of *Mycobacterium paratuberculosis* and diagnosis of Johne's disease. 1993 J. Clin. Microbiol. 31:1601-1605.
69. Strommenger, B., K. Stevenson, and G. F. Gerlach. Isolation and diagnostic potential of ISMav2, a novel insertion sequence-like element from *Mycobacterium avium* subspecies *paratuberculosis*. 2001, FEMS Microbiol. Lett. 196:31-37.
70. Lee, M. H.; Pascopella, L.; Jacobs, W. R.; Hatfull, G. F. "Site-specific integration of mycobacteriophageL5:integration-proficient vectors for *Mycobacterium smegmatis, Mycobacterium tuberculosis*, and bacille Calmette-Guerin." 1991, Proceedings of the National Academy of Sciences 88 (8): 3111-3115.
71. Dynabeads® M-280 Tosylactivated, invitrogen by Life technologies, 2012.
72. Paul R. Meyers, William R. Bourn, Lafras M. Steyn, Paul D. Van Helden, Albert D. Beyers, and Gordon D. Brown, Novel Method for Rapid Measurement of Growth of Mycobacteria in Detergent-Free Media. Journal of Clinical Microbiology, September 1998, p. 2752-2754. Vol. 36, No. 9
73. Englund, S., Bolske, G., Johansson, K. E., 2002. An IS900 like sequence found in a *Mycobacterium* sp. other than *Mycobacterium avium* subspecies *paratuberculosis*. FEMS Microbiol. Lett. 209, 267-271.
74. Coetsier, C., P. Vannuffel, N. Blondeel, J. F. Denef, C. Cocito, and J. L. Gala. Duplex PCR for differential identification of *Mycobacterium bovis, M. avium*, and *M. avium* subsp. *paratuberculosis* in formalin-fixed paraffinembedded tissues from cattle. 2000 J. Clin. Microbiol. 38:3048-3054
75. Harris, N. B., and R. G. Barletta. *Mycobacterium avium* subsp. *paratuberculosis* in veterinary medicine. Clin. Microbiol. 2001, Rev. 14:489-512.
76. U.S. Pat. No. 8,163,567

While specific embodiments have been described above with reference to the disclosed embodiments, examples, and techniques, they are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference.

We claim:

1. An isolated, purified recombinant polypeptide, immobilized to a support, comprising an amino acid sequence defined by SEQ ID NO:3 or an amino acid sequence which is at least 90% identical thereto immobilized to a solid support, wherein the polypeptide is a receptor binding protein, wherein the receptor binding protein is from a *mycobacterium* phage, wherein the receptor binding protein comprises Gp-10.

2. The polypeptide immobilized to a support of claim 1, wherein the polypeptide is a receptor binding protein.

3. The immobilized to a support protein of claim 2, wherein the receptor binding protein is from a *mycobacterium* phage.

4. A method for producing a recombinant *mycobacterium* phage receptor binding protein, comprising identifying a gene encoding a receptor binding protein from a *mycobacterium* phage, amplifying said gene, cloning the amplified gene into an expression vector, and inserting the vector into a bacterium, wherein the bacterium expresses the recombinant receptor binding protein, wherein the recombinant receptor binding protein is Gp-10.

5. The method of claim 4, wherein the recombinant receptor binding protein is purified.

6. A method for the capture of mycobacteria cells in a sample, comprising:

1) immobilizing a recombinant receptor binding protein from a *mycobacterium* phage to the surface of a solid support wherein the recombinant receptor binding protein comprises Gp-10; and
2) contacting the solid support with an amount of a sample containing mycobacteria cells and other components, wherein the recombinant receptor binding protein binds mycobacteria cells in the sample and does not bind the other components of the sample.

7. The method of claim 6, wherein the mycobacteria in the sample are *M. avium, M. avium* subspecies *paratuberculosis*, or *M. smegmatis*, or a mixture thereof.

8. The method of claim 6, wherein the sample is a biological sample or an environmental sample.

9. A method of diagnosing a condition caused by mycobacteria, comprising
   a. obtaining a biological sample from an animal suspected of having a condition caused by mycobacteria,
   b. contacting said sample with a recombinant receptor binding protein from a *mycobacterium* phage wherein said recombinant receptor binding protein forms a complex with mycobacteria if present in said sample,
   c. detecting the complex in the sample, and
   d. comparing the detected said formation of a complex in the sample relative to a control sample, wherein the formation of the complex in the sample relative to the control sample is indicative of the animal having a condition caused by *mycobacterium*, wherein the recombinant receptor binding protein is Gp-10.

10. The method of claim 9, wherein the mycobacteria in the sample are *M. avium* or *M. avium* subspecies *paratuberculosis*.

11. The method of claim 9, wherein the animal is a mammal.

12. The method of claim 11, wherein the animal is a ruminant.

13. The method of claim 9, wherein the condition is Johne's disease.

14. A method of enhancing the sensitivity of a diagnostic assay for mycobacteria, comprising a. obtaining a sample containing mycobacteria, b. performing the method of claim 6 on the sample, and removing at least a portion of said other components from said sample to produce a concentrated sample of mycobacteria; and then c. performing a diagnostic assay on the concentrated sample, wherein the sensitivity of the diagnostic assay is increased using the concentrated sample, as compared to the sensitivity of the diagnostic assay when using a corresponding unconcentrated sample.

15. The method of claim 14, wherein the subject is an animal.

16. The method of claim 15, wherein the subject is a human.

17. The polypeptide immobilized to a support of claim 1, wherein said support comprises a bead, a particle, a fiber, a tube, a wafer, a chip, a filter, or a membrane.

18. The polypeptide immobilized to a support of claim 1, wherein said support comprises a metal, a polymer, a dielectric semiconductor, or cellulose.

* * * * *

UNITED STATES PATENT AND TRADEMARK OFFICE
CERTIFICATE OF CORRECTION

PATENT NO. : 9,885,713 B2
APPLICATION NO. : 14/909430
DATED : February 6, 2018
INVENTOR(S) : Stephane Evoy et al.

It is certified that error appears in the above-identified patent and that said Letters Patent is hereby corrected as shown below:

In the Specification

Column 4, Line 44, after "Mycobacterium" insert --smegmatis sample isolated from 3 percent milk, using Gp-10 functionalized beads.--

Signed and Sealed this
Twenty-fourth Day of July, 2018

Andrei Iancu
*Director of the United States Patent and Trademark Office*

SEQUENCE LISTING

```
<160> NUMBER OF SEQ ID NOS: 17

<210> SEQ ID NO 1
<211> LENGTH: 365
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1
```

```
Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Ala Asp Ile
            35                  40                  45

Gly Ser Glu Phe Met Ala Asp Leu Gly Asn Pro Leu Asp Leu Glu Met
50                  55                  60

Leu Cys Leu Val Thr Gly Arg Asp Phe Arg Trp Thr Ile Asp Tyr Pro
65                  70                  75                  80

Trp Gly Pro Gly Glu Leu Phe Leu Glu Leu Glu Thr Gly Gly Glu His
                85                  90                  95

Asn Ala Leu His Gln Val Tyr Val Thr Gly Ala Thr Gly Gly Thr Tyr
            100                 105                 110

Thr Leu Asn Val Asn Gly Thr Asn Thr Pro Ala Ile Asp Tyr Asn Asp
            115                 120                 125

Val Ser Glu Asn Pro Gln Gly Leu Ala Gly Asp Ile Gln Asp Ala Leu
        130                 135                 140

Asp Ala Ala Val Gly Ala Gly Asn Ala Val Val His Pro Val Ser Leu
145                 150                 155                 160

Phe Pro Ala Trp Thr Leu Asn Phe Asn Leu Asn Ala Ser Lys Pro Leu
                165                 170                 175

Thr Glu Gln Leu Val Asn Thr Ile Asn Lys Ala Ala Asn Asp Phe Phe
            180                 185                 190

Asp Thr Phe Asp Gln Leu Leu Gly Val Asp Val Glu Met Thr Val Thr
            195                 200                 205

Asp Thr Leu Asn Phe Lys Leu Lys Val Thr Ser Arg Arg Ser Phe Asp
210                 215                 220

Glu Val Gly Val Val Thr Phe Ala Val Asp Val Thr Ser Gln Ala Val
225                 230                 235                 240

Ile Asn Phe Phe Asn Ser Val Ala Glu Leu Thr Gly Ala Val Asn Thr
                245                 250                 255

Val Asn Val Asp Phe Tyr Trp Asn Arg Thr Tyr Asp Ile Glu Phe Thr
            260                 265                 270

Gly Ser Leu Gly Leu Gln Pro Ile Pro Ala Thr Thr Ala Asp Ile Thr
            275                 280                 285

Asn Leu Ala Gly Thr Ser Lys Ala Val Ser Val Thr Val Val Glu Pro
        290                 295                 300

Gly Lys Lys Arg Leu Thr Ile Trp Pro Phe Thr Val Asn Gly Glu Thr
305                 310                 315                 320

Ala Thr Ile Lys Val Glu Ser Glu Glu Ala Asp Lys Ile Pro Asn Arg
                325                 330                 335

Cys Arg Trp Gln Leu Val His Met Pro Thr Gly Glu Ala Ala Gly Gly
            340                 345                 350

Asp Ala Lys Gln Leu Gly Arg Val Tyr Arg Gln Pro Arg
            355                 360                 365

<210> SEQ ID NO 2
<211> LENGTH: 1098
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
```

<400> SEQUENCE: 2

```
atgcaccatc atcatcatca ttcttctggt ctggtgccac gcggttctgg tatgaaagaa      60
accgctgctg ctaaattcga acgccagcac atggacagcc agatctggg taccgacgac      120
gacgacaagg ccatggctga tatcggatcc gaattcatgg ccgacctcgg caacccactc     180
gacctcgaga tgctctgcct ggtcacaggc cgggacttcc gctggaccat cgattacccg     240
tggggtccgg gagagctgtt cctcgaactc gagaccggcg cgaacacaa cgcgctgcat      300
caggtctatg tcaccggggc gaccggaggc acgtacacgc tgaacgtcaa cggcaccaac     360
accccggcca tcgactacaa cgacgtgtcg gagaatccgc aggggctggc aggcgacatc     420
caagacgctc tggacgcagc cgtcggagcc ggaaacgctg tcgtgcatcc ggtctcgctg     480
ttccctgcgt ggacactgaa cttcaacctc aacgccagca agccgctcac cgagcagttg     540
gtcaacacga tcaacaaggc cgcgaacgac ttcttcgaca cgttcgacca actacttggg     600
gtcgacgtgg agatgacggt caccgacacc ctgaacttca gctcaaggt gacctcgcgg      660
cgctcgttcg atgaggtcgg tgtcgtcacg ttcgcggtcg acgtgaccag ccaggcagtc     720
atcaacttct tcaactccgt cgccgaactc accggagcgg tgaacaccgt caacgtcgac     780
ttctactgga accggacgta tgacatcgag ttcaccggat cccttgggct gcagccgatt     840
ccggctacta cagccgacat caccaacctg gcgggtacca gcaaggccgt ctcagtcacg     900
gtggtcgagc aggaaagaa gaggctgacc atctggccgt tcacggtcaa cggtgaaacc      960
gcaaccatca aggtcgagtc cgaagaggcc gacaagatcc ccaaccgctg ccgctggcag    1020
ttggttcaca tgccgaccgg cgaggcagcc ggcggcgatg caaagcagct cggccgcgtt    1080
taccgacagc cgaggtaa                                                  1098
```

<210> SEQ ID NO 3
<211> LENGTH: 344
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

```
Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Ala Asp Ile
        35                  40                  45

Gly Ser Glu Phe Met Thr Phe Thr Val Thr Arg Glu Arg Ala Gln Trp
50                  55                  60

Val His Asp Met Ala Arg Ala Arg Asp Gly Leu Pro Tyr Ala Tyr Gly
65                  70                  75                  80

Gly Ala Phe Thr Asn Asn Pro Arg Val Ser Thr Asp Cys Ser Gly Leu
                85                  90                  95

Val Leu Gln Thr Gly Ala Trp Tyr Gly Gly Arg Thr Asp Trp Val Gly
            100                 105                 110

Asn Arg Tyr Gly Ser Thr Glu Ser Phe Arg Leu Asp His Lys Ile Val
        115                 120                 125

Tyr Asp Leu Gly Phe Lys Arg Met Pro Arg Gly Gly Pro Ala Ala Leu
    130                 135                 140
```

```
Pro Ile Lys Pro Val Met Leu Val Gly Leu Gln His Gly Gly Gly
145                 150                 155                 160

Val Tyr Ser His Thr Ala Cys Thr Leu Met Thr Met Asp His Pro Gly
                165                 170                 175

Gly Pro Val Lys Met Ser Asp Arg Gly Val Asp Trp Glu Ser His Gly
            180                 185                 190

Asn Arg Asn Gly Val Gly Val Glu Leu Tyr Glu Gly Ala Arg Ala Trp
        195                 200                 205

Asn Asp Pro Leu Phe His Asp Phe Trp Tyr Leu Asp Ala Val Leu Glu
            210                 215                 220

Asp Glu Gly Asp Asp Glu Leu Ala Asp Pro Val Leu Gly Lys Met
225                 230                 235                 240

Ile Arg Glu Ile His Ala Cys Leu Phe Asn Gln Thr Ala Ser Thr Ser
                245                 250                 255

Asp Leu Ala Thr Pro Gly Glu Gly Ala Ile Trp Gln Leu His Gln Lys
            260                 265                 270

Ile His Ser Ile Asp Gly Met Leu His Pro Ile His Ala Glu Arg Arg
        275                 280                 285

Ala Arg Ala Gly Asp Leu Gly Glu Leu His Arg Ile Val Leu Ala Ala
290                 295                 300

Lys Gly Leu Gly Val Lys Arg Asp Glu Val Thr Lys Arg Val Tyr Gln
305                 310                 315                 320

Ser Ile Leu Ala Asp Ile Glu Arg Asp Asn Pro Glu Val Leu Gln Arg
                325                 330                 335

Tyr Ile Ala Glu Arg Gly Gly Leu
            340

<210> SEQ ID NO 4
<211> LENGTH: 1035
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
atgcaccatc atcatcatca ttcttctggt ctggtgccac gcggttctgg tatgaaagaa      60
accgctgctg ctaaattcga acgccagcac atggacagcc agatctggga taccgacgac     120
gacgacaagg ccatggctga tatcggatcc gaattcatga ccttcacagt cacccgcgag     180
agagcgcagt gggtccacga catggcccgc gctcgcgacg tctccccta cgcgtacggc     240 ggggcgttca ccaacaaccc gagggtgtcg actgactgct ctggcctggt gctgcagacc     300
ggggcttggt atggaggtcg caccgactgg gtcggaaacc gttacggctc aaccgaatcg     360
ttccggctcg accacaagat cgtctacgac ctagggttca gcggatgcc ccgaggcggg      420 ccagcggcct tgccgatcaa gccggtgatg ctcgtcgggc tccagcacgg aggcggcggg     480
gtctactcgc acaccgcttg cacgttgatg acgatggacc accccggtgg cccggtcaag     540
atgtccgacc gaggcgtcga ctgggagtcc cacggcaacc gcaacggcgt aggcgtcgaa     600
ctttacgagg gcgcacgggc atggaacgac cctctgttcc atgactttg gtacctggac      660 gcagtcctcg aagacgaagg agacgatgac gaattggctg acccagttct agggaagatg     720
atccgcgaga tccacgcgtg cctgttcaat cagaccgcgt cgaccagcga tctggcgacc     780
cctggtgaag gcgctatctg gcagctacac cagaagatcc actcgattga cggcatgctc     840
```

```
cacccgatcc acgctgagcg gcgcgctcgc gcaggcgatc tcggtgagct gcaccgaatc    900
gtgttggccg cgaagggctt gggcgtgaag cgcgacgagg tgaccaagcg ggtctaccag    960
agcatcctcg ccgacatcga gcgggacaac cccgaagtac ttcagcgata catcgcagaa   1020
agaggtggcc tatga                                                    1035
```

<210> SEQ ID NO 5
<211> LENGTH: 600
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

```
Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala Asp Ile
        35                  40                  45

Gly Ser Glu Phe Val Thr Tyr Pro Thr Asn Pro Leu Glu Ala Ile Gly
    50                  55                  60

Ala Asp Gly Ala Phe Glu Ile Gly Gly Asp Trp Ser Phe Gly Gln
65                  70                  75                  80

Asp Tyr Thr Glu Gln Ala Ile Arg Ala Leu Phe Thr Met Pro Ala Val
                85                  90                  95

Thr Met Glu Asn Ala Leu Gly Leu Leu Glu His Leu Leu Lys Leu
            100                 105                 110

Pro Leu Glu Ala Leu Gln Gly Phe Lys Asp Met Ile Pro Asp Trp Val
        115                 120                 125

Glu Gly Ala Phe Asp Thr Val Thr Gly Ala Val Gln Ala Ile Met Asn
    130                 135                 140

Ala Leu Gln Asp Gly Pro Leu Phe Leu Lys Phe Ala Glu Phe Gln Leu
145                 150                 155                 160

Phe Leu Gln Arg Leu Leu Asn Asn Pro Ala Glu Val Ile Gly Glu Ile
                165                 170                 175

Pro Gln Thr Leu Ile Asp Gly Leu Gln Asp Ala Leu Asn Thr Val Asn
            180                 185                 190

Asn Thr Ile Gln Thr Ile Val Asp Met Leu Leu Gln Ala Leu Gly Ile
        195                 200                 205

Thr Pro Glu Gly Glu Leu Ile Asp Arg Ile Phe Asp Leu Ser Asp Glu
    210                 215                 220

Met Glu Trp Leu Gln Thr Ala Ala Ser Asn Ala Thr Gly Ile Gln
225                 230                 235                 240

Asp Thr Trp Asn Lys Phe Trp Gly Ala Leu Thr Gly Arg Val Pro Asp
                245                 250                 255

Gln Asp Gln Thr Val Ala Glu Pro Ala Glu Arg Ile Gly Glu Leu Ala
            260                 265                 270

Gly Thr Thr Ser Ala Asn Ser Ser Ala Ile Ala Glu Leu Gln Arg Arg
        275                 280                 285

Leu Asp Asn Gln Gln Asn Ala Gly Gly Val Ala Gly Asp Asp Phe
    290                 295                 300

Glu Arg Leu Asn Ile Ser Gly Trp Asp Ile Arg Tyr Ser Asn Gly Ser
305                 310                 315                 320
```

Ser Gly Arg Gly Tyr Tyr Arg Ala Asp Gly His Gln Leu Val Trp Met
            325                 330                 335

Asp Glu Gly Asn Gln Gln Asn Thr Ala Thr Phe Val Arg Thr Asn Pro
            340                 345                 350

Ala Asp Glu Lys Thr Ala Thr Asp Tyr Gln Lys Met Thr Leu Val Val
            355                 360                 365

Gly Thr Ile Ser Gly Glu Val Gln Thr Val Phe Pro Pro Gln Gly Gly
            370                 375                 380

Ser His Thr Arg Leu Trp Val Arg Val Asn Asp Asn Ala Pro Thr Val
385                 390                 395                 400

Gly Ile Thr Asp Gly Val Phe Val Glu Ile Gly Gly Val Ser Lys Ala
            405                 410                 415

Gln Ile Gly Tyr Arg Arg Asn Gly Asn Asp Thr Phe Val Gly Ser Met
            420                 425                 430

Val Asp Cys Thr Trp Gly Ala Gly Ser Ile Phe Ala Leu Thr Ala Gly
            435                 440                 445

Thr Ala Asn Gly Ala Glu Lys Phe Glu Val Ser Lys Asn Gly Pro Val
450                 455                 460

Leu Ala Thr Trp Ser Asp Asp Gly Val Val Ser Ala Met Gly Ala Asn
465                 470                 475                 480

Tyr Arg Arg Trp Gly Trp Glu Gly Gln Ala Arg Asn Arg Asn Leu Gly
            485                 490                 495

Gln Gly Thr Pro Asn Ser Val Thr Arg Val Thr Ile Thr Asp Asn Asp
            500                 505                 510

Pro Thr Gly Ala Gly Gly Ala Val Asn Val Gly Asp Val Val
            515                 520                 525

Gly Val Leu Pro Ile Glu Asn Gly Gly Thr Gly Ala Ser Thr Ala Ser
            530                 535                 540

Ala Ala Arg Thr Ala Leu Gly Ile Asp Asp Leu Val Glu Asp Met Ser
545                 550                 555                 560

Asp Val Val Arg Gly Ser Val Glu Gly Leu Pro Leu Ile Pro Lys Ile
            565                 570                 575

Trp Val Gly Thr Glu Ala Gln Tyr Thr Ala Leu Ala Thr Lys Asp Gln
            580                 585                 590

Ser Thr Leu Tyr Phe Arg Thr Ala
            595                 600

<210> SEQ ID NO 6
<211> LENGTH: 1803
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
atgcaccatc atcatcatca ttcttctggt ctggtgccac gcggttctgg tatgaaagaa    60
accgctgctg ctaaattcga acgccagcac atggacagcc agatctggg taccgacgac    120 gacgacaagg ccatggctga tatcggatcc gaattcgtga cctaccccac caacccacta   180
gaggccatcg cgctgacgg cgcattcgag atcggtgggg cgactggag cttcggccag    240 gactacaccg aacaggccat ccgggctctg ttcacgatgc cagcggtcac gatggagaac    300
gctctcggcc tgctcgaaga gcacctgctg aagctgcctc tggaggcgct gcagggcttc    360

-continued

```
aaagacatga tcccggactg ggtcgaagga gcattcgaca cggtcaccgg cgctgtgcag    420
gcgatcatga acgcgctcca agacggcccg ctgttcctga agttcgccga gttccagctc    480
ttcctgcagc gtctgctgaa caacccggcc gaggtcatcg gcgagatccc ccagacgttg    540
atcgacggcc tacaggacgc gctcaacacc gtcaacaaca ccatccagac catcgtggac    600
atgctcctgc aggcgctggg catcaccccg gaggggagc tgatcgaccg gatcttcgac     660
ctgagcgatg agatggagtg gctgcagacc gcagcctcga atgcagctac cggcatccag    720
gacacctgga acaagttctg gggagccctc accgggcgcg tcccagacca ggaccagacc    780
gtcgctgagc ccgccgagcg tatcggcgag ctggccggca ccacgtctgc taactcgtct    840
gccatcgcgg agctgcagcg tcgactggac aaccagcaga acgctggcgg cgtggccggc    900
ggtgacgact cgagcgact  gaacatatcc ggttgggaca tcaggtattc caacggatcc    960
agcggccgag ggtactaccg tgccgacggc caccaactgg tctggatgga cgaaggcaac   1020
cagcagaaca ccgcgacgtt cgtccgcacc aaccccgcag acgagaagac agccaccgac   1080
taccagaaga tgacgttggt cgtcgggact atctccggtg aggtacagac cgtgttcccg   1140
ccgcagggag gttcgcacac ccggctatgg gtccgcgtca acgacaacgc tccgaccgtc   1200
ggcatcaccg acgcgtgtt  cgtagagatc ggcggcgtat cgaaggccca gatcggctac   1260
cgccgcaacg gcaatgacac gttcgtcgga tctatggtcg actgcacctg gggtgctgga   1320
tcgatcttcg ctctgaccgc cggcacggcc aacggtgctg agaagttcga ggtctcgaag   1380
aacggccccg tgctggccac atggtcggac gacggcgtcg tctccgcgat gggtgcgaac   1440
taccgccgct ggggctggga aggccaggct cgtaaccgca acctcggcca gggcactccg   1500
aactcggtca cccgagtgac gatcaccgac aacgatccta ccggcgcagg cggtggagct   1560
gtcaacgtcg gaggagatgt cgtaggtgta ctccccatag agaacggagg caccggagct   1620
tcgacagctt cggcagcccg taccgctctc ggaatcgatg acctggtcga agatatgtcc   1680
gacgtagttc gtggatccgt cgaaggactc ccgttgatac cgaagatctg ggtaggaaca   1740
gaagctcagt acacggctct cgccaccaag gatcagtcca cgctatactt caggaccgct   1800
taa                                                                 1803
```

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
tgacggttac ggaggtggtt                                                 20

<210> SEQ ID NO 8
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
cggtccagtt cgctgtcat                                                  19

<210> SEQ ID NO 9
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
atgcagtaat ggtcggcctt a                                            21

<210> SEQ ID NO 10
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
cacgcaggca ttccaagtc                                               19

<210> SEQ ID NO 11
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 11
tggcacaacc tgtctg                                                  16

<210> SEQ ID NO 12
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 12
acgggaaggg tggtc                                                   15

<210> SEQ ID NO 13
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
ggcatcgaat tcatggccga cctcggcaac ccactcg                           37

<210> SEQ ID NO 14
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

-continued

```
<400> SEQUENCE: 14
gatgctaagc ttttacctcg gctgtcggta aacgcggc                              38

<210> SEQ ID NO 15
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
ggcatcgaat tcatgacctt cacagtcacc cgcgag                                36

<210> SEQ ID NO 16
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
gatgctaagc tttcataggc cacctctttc tgcgatg                               37

<210> SEQ ID NO 17
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 17

His His His His His His
1               5
```